United States Patent

Mueller et al.

[11] Patent Number: 5,962,489
[45] Date of Patent: Oct. 5, 1999

[54] HETEROAROMATIC COMPOUNDS AND CROP PROTECTION AGENTS CONTAINING THEM

[75] Inventors: Bernd Mueller, Frankenthal; Hubert Sauter; Horst Wingert, both of Mannheim; Hartmann Koenig, Limburgerhof; Franz Roehl, Schifferstadt; Eberhard Ammermann, Heppenheim; Gisela Lorenz, Neustadt, all of Germany

[73] Assignee: BASF Aktiengesellschaft, Ludwigshafen, Germany

[21] Appl. No.: 09/141,331

[22] Filed: Aug. 27, 1998

Related U.S. Application Data

[62] Division of application No. 08/949,761, Oct. 14, 1997, Pat. No. 5,817,682, which is a division of application No. 08/888,899, Jul. 7, 1997, Pat. No. 5,736,566, which is a continuation of application No. 08/500,138, Jul. 10, 1995, abandoned, which is a continuation of application No. 08/091,265, Jul. 15, 1993, abandoned.

Foreign Application Priority Data

Jul. 16, 1992 [DE] Germany .............................. 42 23 357

[51] Int. Cl.⁶ .......................... A01N 43/80; A01N 43/56; C07D 261/02; C07D 231/10
[52] U.S. Cl. ......................... 514/378; 514/406; 548/240; 548/375.1
[58] Field of Search ................. 548/240, 375.1; 514/378, 406

[56] References Cited

U.S. PATENT DOCUMENTS

| | | |
|---|---|---|
| 4,152,432 | 5/1979 | Heymes et al. |
| 4,416,880 | 11/1983 | Boberg et al. |
| 4,497,745 | 2/1985 | Martin |
| 4,863,503 | 9/1989 | Anthony et al. |
| 5,502,070 | 3/1996 | Fuchs et al. |
| 5,506,254 | 4/1996 | Kirstgen et al. |
| 5,523,280 | 6/1996 | Chene et al. |
| 5,672,616 | 9/1997 | Mueller et al. |
| 5,675,017 | 10/1997 | Hamper et al. |
| 5,739,153 | 4/1998 | Peignier et al. |

FOREIGN PATENT DOCUMENTS

| | | |
|---|---|---|
| 0 178 826 | 4/1986 | European Pat. Off. |
| 0 206 253 | 12/1986 | European Pat. Off. |
| 0 243 014 | 10/1987 | European Pat. Off. |
| 0 331 966 | 9/1989 | European Pat. Off. |
| 0 384 211 | 8/1990 | European Pat. Off. |
| 0 389 901 | 10/1990 | European Pat. Off. |
| 0 402 246 | 12/1990 | European Pat. Off. |
| 0 433 899 | 6/1991 | European Pat. Off. |
| 0 471 262 | 2/1992 | European Pat. Off. |
| 0 483 851 | 5/1992 | European Pat. Off. |
| 0 489 660 | 6/1992 | European Pat. Off. |
| 0 508 901 | 10/1992 | European Pat. Off. |
| 0 509 857 | 10/1992 | European Pat. Off. |
| 196008 | 11/1983 | New Zealand |
| 2 172 595 | 9/1986 | United Kingdom |

Primary Examiner—Deborah C. Lambkin
Attorney, Agent, or Firm—Oblon, Spivak, McClelland, Maier & Neustadt, P.C.

[57] ABSTRACT

Heteroaromatic compounds of the formulae IA and IB

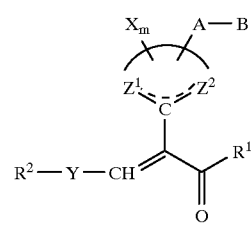

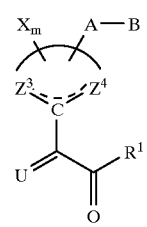

where the dashed line is a double bond between the carbon atom and a Z atom, and the index and the substituents have the following meanings:

$R^1$
alkyl, alkoxy, alkylamino
$R^2$
alkyl;
A
a direct bond; alkylene, alkenylene, alkynylene;
O, S, S-oxides, N and alkylene derivatives or oxime radicals thereof
B
hydrogen, halogen,
alkyl, alkenyl, alkynyl;
cycloalkyl, cycloalkenyl, cycloalkynyl, heterocyclyl, aryl, hetaryl
U
$CH_2$, CHCl, $CHR^2$ or $NOR^2$;
X
hydrogen, cyano, nitro, halogen,
alkyl, alkenyl, alkynyl, cycloalkyl, cycloalkenyl, heterocyclyl, aryl, hetaryl; oxi- and thio derivatives thereof, carbonyl derivatives thereof, carbonyloxy derivatives thereof, amino derivatives thereof, oxime derivatives thereof,
amino which may bear one or two of the abovementioned groups;
m
1 or 2,
Y
oxygen or sulfur;
$Z^1$-$Z^2$, $Z^3$-$Z^4$,
together with the carbon atom to which they are bonded, are the radical of a heteroaromatic, and fungicides containing these compounds.

10 Claims, No Drawings

HETEROAROMATIC COMPOUNDS AND CROP PROTECTION AGENTS CONTAINING THEM

This application is a Division of application Ser. No. 08/949,761 filed Oct. 14, 1997 U.S. Pat. No. 5,817,682, which is a division of application Ser. No. 08/858,889 filed Jul. 7, 1997 U.S. Pat. No. 5,736,566, which is a continuation of application Ser. No. 08/500,138 filed Jul. 10, 1995 now abandoned which is a continuation of application Ser. No. 08/091,265, filed Jul. 15, 1993 now abandoned.

The present invention relates to heteroaromatic compounds and their use as crop protection agents, in particular for controlling fungi, insects, nematodes and spider mites.

It is known that phenylacrylates, for example methyl 2-(2-methylphenyl)-3-methoxyacrylate (EP 178826), can be used as fungicides. However, their fungicidal action is unsatisfactory.

We have found, surprisingly, that heteroaromatic compounds of the formula I where the dashed line is a double bond between the carbon atom and $Z^1$ or $Z^3$ or between the carbon atom and $Z^2$ or $Z^4$, $R^1$ is $C_1$–$C_6$-alkyl, $C_1$–$C_6$-alkoxy, $C_1$–$C_6$-alkylamino or di-$C_1$–$C_6$-alkylamino;

$R^2$ is $C_1$–$C_6$-alkyl;

A is a direct bond; unsubstituted or substituted alkylene, alkenylene or alkynylene;

—$(CHR^4)_n$—O—, —$(CHR^4)_n$—S—, —$(CHR^4)_n$—NH—, —$(CHR^4)_n$—$NR^5$—, —$(CHR^4)_n$—S(=O)—, —$(CHR^4)_n$—S(=O)$_2$—, —$(CHR^4)_n$—O—S(=O)—, —$(CHR^4)_n$—S(=O)—O—, —$(CHR^4)_n$—O—S(=O)$_2$—, —$(CHR^4)_n$—S(=O)$_2$—O—, —$(CHR^4)_n$—C(=O)—, —$(CHR^4)_n$—C(=O)O—, —$(CHR^4)_n$—O—C(=O)—, —$(CHR^4)_n$—$CR^5$=N—O—, —$(CHR^4)_n$—$CR^5$=N—N=$CR^6$—, —$(CHR^4)_n$—O—N=$CR^7$—, n is 0, 1, 2, 3 or 4, and the radicals $R^4$ may be different when n is greater than 1;

$R^4$, $R^5$ and $R^6$ independently of one another are each hydrogen or unsubstituted or substituted $C_1$–$C_6$-alkyl, $C_2$–$C_6$-alkenyl, $C_2$–$C_6$-alkynyl or aryl;

$R^7$ is hydrogen, cyano; unsubstituted or substituted alkyl, alkenyl, alkynyl, cycloalkyl, cycloalkenyl, cycloalkynyl, heterocyclyl, aryl, hetaryl;

unsubstituted or substituted alkoxy, alkenyloxy, alkynyloxy, cycloalkoxy, cycloalkenyloxy, cycloalkynyloxy, heterocyclyloxy, aryloxy, hetaryloxy;

or $R^7$ and B, together with the carbon atom to which they are bonded, form an unsubstituted or substituted, saturated or partially unsaturated alicyclic or heterocyclic system;

B is hydrogen, halogen, unsubstituted or substituted alkyl, alkenyl, alkynyl;

cycloalkyl, cycloalkenyl, cycloalkynyl, heterocyclyl, aryl, hetaryl, —$(CHR^4)_p$—cycloalkyl, —$(CHR^4)_p$—cycloalkenyl, —$(CHR^4)_p$—cycloalkynyl, —$(CHR^4)_p$—heterocyclyl, —$(CHR^4)_p$—aryl, —$(CHR^4)_p$—hetaryl, —$(CHR^4)_p$—O-cycloalkyl, $(CHR^4)_p$—O-cycloalkenyl, —$(CHR^4)_p$—O-cycloalkynyl, —$(CHR^4)_p$—O-heterocyclyl, —$(CHR^4)_p$—O-aryl, —$(CHR^4)_p$—O-hetaryl, —$(CHR^4)_p$—S-cycloalkyl, —$(CHR^4)_p$—S-cycloalkenyl, —$(CHR^4)_p$—S-cycloalkynyl, —$(CHR^4)_p$—S-heterocyclyl, —$(CHR^4)_p$—S-aryl, —$(CHR^4)_p$—S-hetaryl, —$(CHR^4)_p$—NH-cycloalkyl, —$(CHR^4)_p$—NH-cycloalkenyl, —$(CHR^4)_p$—NH-cycloalkynyl, —$(CHR^4)_p$—NH-heterocyclyl, —$(CHR^4)_p$—NH-aryl, —$(CHR^4)_p$—NH-hetaryl, —$(CHR^4)_p$—$NR^5$-cycloalkyl, —$(CHR^4)_p$—$NR^5$-cycloalkenyl, —$(CHR^4)_p$—$NR^5$-cycloalkynyl, —$(CHR^4)_p$—$NR^5$-heterocyclyl, —$(CHR^4)_p$—$NR^5$-aryl, —$(CHR^4)_p$—$NR^5$-hetaryl, where the abovementioned cyclic radicals may in turn carry substituents;

p is 1, 2, 3 or 4, and the radicals $R^4$ may be different when n is greater than 1;

U is $CH_2$, CHCl, $CHR^2$ or $NOR^2$;

X is hydrogen, c-yano, nitro, halogen, haloalkyl, haloalkoxy, unsubstituted or substituted alkyl, alkenyl, alkynyl, cycloalkyl, cycloalkenyl, heterocyclyl, aryl, hetaryl; unsubstituted or substituted alkoxy, alkenyloxy, alkynyloxy, cycloalkoxy, cycloalkenyloxy, heterocyclyloxy, aryloxy, hetaryloxy;

unsubstituted or substituted alkylthio, alkenylthio, alkynylthio, cycloalkylthio, cycloalkenylthio, heterocyclylthio, arylthio, hetarylthio;

amino which may carry one or two of the following groups: unsubstituted or substituted alkyl, alkenyl, alkynyl, cycloalkyl, cycloalkenyl, heterocyclyl, aryl and/or hetaryl;

unsubstituted or substituted alkylcarbonyl, alkenylcarbonyl, alkynylcarbonyl, cycloalkylcarbonyl, cycloalkeriylcarbonyl, heterocyclylcarbonyl, arylcarbonyl, hetarylcarbonyl;

unsubstituted or substituted alkylcarbonyloxy, alkenylcarbonyloxy, alkynylc arbonyloxy, cycloalkyic arbonyloxy, cycloalkenylcarbonyloxy, heterocyclylcarbonyioxy, arylcarbonyloxy, hetarylcarbonyloxy;

unsubstituted or substituted alkoxycarbonyl, alkenyloxycarbonyl, alkynyloxycarbonyl, cycloalkoxycarbonyl, cycloalkenyloxycarbonyl, heterocyclyloxycarbonyl, arloxycarbodnyl, hetarloxycarbonyl;

unsubstituted or substituted alkylcarbonylamino, alkenylcarbonylamino, alkynylcarbonylamino, cycloalkylcarbonylamino, cycloalkenylcarbonylamino, heterocyclylcarbonylamino, arylcarbonylamino or hetarylcarbonyjamino, where these radicals may additionally carry one of the following groups on the amino groups: unsubstituted or substituted alkyl, alkenyl, alkynyl, cycloalkyl, cycloalkenyl, heterocyclyl, aryl and/or hetaryl;

aminocarbonyl which may carry one or two of the following groups on the amino group: unsubstituted or substituted alkyl, alkenyl, alkynyl, cycloalkyl, cycloalkenyl, heterocyclyl, aryl and/or hetaryl;

unsubstituted or substituted alkyl-S (=O)—, alkenyl-S(=O)—, alkynyl-S(=O)—, cycloalkyl-S(=O)—, cycloalkenyl-S(=O)—, heterocyclyl-S(=O)—, aryl-S(=O)—, hetaryl-S(=O)—; unsubstituted or substituted alkyl-S (=O)—O—, alkenyl-S(=O)—O—, alkynyl-S(=O)—O—, cycloalkyl-S(=O)—O—, cycloalkenyl-S(=O)—O—, heterocyclyl-S(=O)—O—, aryl-S(=O)—O—, hetaryl-S(=O)—O—; unsubstituted or substituted alkyl-O—S(=O)—, alkenyl-O—S(=O)—, alkynyl-O—S(=O)—, cycloalkyl-O—S(=O)—, cycloalkenyl-O—S(=O)—, heterocyclyl-O—S(=O)—, aryl-O—S(=O)—, hetaryl-O—S(=O)—;

unsubstituted or substituted alkyl-S(=O)$_2$—, alkenyl-S(=O)$_2$—, alkynyl-S(=O)$_2$—, cycloalkyl-S(=O)$_2$—, cycloalkenyl-S(=O)$_2$—, heterocyclyl-S(=O)$_2$—, aryl-S(=O)$_2$—, hetaryl-S(=O)$_2$—;

unsubstituted or substituted alkyl-S(=O)$_2$—O—, alkenyl-S(=O)$_2$—O—, alkynyl-S(=O)$_2$—O—, cycloalkyl-S(=O)$_2$—O—, cycloalkenyl-S(=O)$_2$—O—, heterocyclyl-S(=O)$_2$—O—, aryl-S(=O)$_2$—O—, hetaryl-S(=O)$_2$—O—;

unsubstituted or :substituted alkyl-O—S(=O)$_2$—, alkenyl-O—S(=O)$_2$—, alkynyl-O—S(=O)$_2$—, cycloalkyl-O—S(=O)$_2$—, cycloalkenyl-O—S(=O)$_2$—, heterocyclyl-O—S(=O)$_2$—, aryl-O—S(=O)$_2$—, hetaryl-O—S(=O)$_2$—;

unsubstituted or substituted alkyl-ON=CR$^8$—, alkenyl-ON=CR$^8$—, alkynyl-ON=CR$^8$—, cycloalkyl-ON=CR$^8$—, cycloalkenyl-ON=CR$^8$—, heterocyclyl-ON=CR$^8$—, aryl-ON=CR$^8$—, hetaryl-ON=CR$^8$—;

R$^8$ is hydrogen, cyano;

unsubstituted or substituted alkyl, alkenyl, alkynyl, cycloalkyl, cycloalkenyl, cycloalkynyl, heterocyclyl, unsubstituted or substituted alkoxy, alkenyloxy, alkynyloxy, cycloalkoxy, cycloalkenyloxy, cycloalkynyloxy, heterocyclyloxy, aryloxy or hetaryloxy;

m is 1 or 2, and the radicals X may be different when m is 2;

Y is oxygen or sulfur;

Z$^1$ and Z$^2$, together with the carbon atom to which they are bonded, form either a 6-membered heteroaromatic structure containing two or three nitrogen atoms in addition to carbon ring members or a 5-membered heteroaromatic structure containing two or three nitrogen atoms or one or two nitrogen atoms and one oxygen or one sulfur atom in addition to carbon ring members, and Z$^3$ and Z$^4$, together with the carbon atom to which they are bonded, form either a 6-membered heteroaromatic structure containing one, two or three nitrogen atoms in addition to carbon ring members or a 5-membered heteroaromatic structure containing one, two or three nitrogen atoms or one oxygen or one sulfur atom or one or two nitrogen atoms and one oxygen or one sulfur atom in addition to carbon ring members, and their plant-tolerated acid addition products and base addition products, with the exception of compounds in which the ring C—Z$^1$—Z$^2$ is a pyrazole ring, —Y—R$^2$ is —O—CH$_3$ and —A—B is in the 4-position on the pyrazole ring, —A— is —O—CH$_2$—, B is unsubstituted or substituted phenyl or unsubstituted or substituted thiazolyl, or the ring C—Z$^1$—Z$^2$ is a pyrazole ring, —Y—R$^2$ is —O—CH$_3$ and —A—B is in the 4-position on the pyrazole ring, —A— is O—CO— and B has the meanings stated in claim 1, or the ring C—Z$^1$—Z$^2$ is a thiazole ring, Y is oxygen and R$^1$ is OCH$_3$, or the ring C—Z$^3$—Z$^4$ is a thiazole ring, X is bonded to an N atom of the thiazole ring and U is NOR$^2$, not only have a high fungitoxic, insecticidal, nematicidal and acaricidal activity but are also very well tolerated by plants.

Acids for acid addition products are, for exampler, mineral acids, such as hydrochloric acid, hydrobromric acid, phosphoric acid, sulfuric acid or nitric acid, or carboxylic acids, such as formic acid, acetic acid, oxalic acid, malonic acid, lactic acid, malic acid, succinic acid, tartaric acid, citric acid, salicylic acid, p-toluenesulfonic acid or dodecylbenzenesulfonic acid, or proton-acidic compounds generally, eg. saccharin.

Bases for base addition products are, for example, potassium hydroxide, sodium hydroxide, potassium carbonate, sodium carbonate and ammonium hydroxide.

The novel compounds of the formula I may be obtained in the preparation as mixtures of stereoisomers (E/Z isomers, diastereomers, enantiomers), which may be separated into the individual components in a conventional manner, for example by crystallization or chromatography. Both the individual isomers and mixtures thereof can be used as fungicides, acaricides, nematicides or insecticides and form subjects of the present invention.

The abovementioned alkyl radicals may be freely substituted, for example by 1–4 identical or different substituents R$^{11}$, are preferably of 1 to 8 carbon atoms and are each, for example, methyl, ethyl, propyl, n-propyl, isopropyl., butyl, n-butyl, isobutyl, tert-butyl, sec-butyl, pentyl, 1-pentyl, 2-pentyl, 3-pentyl, 2-methylbutyl-1, 2-methylbutyl-2, 2-methylbutyl-3, 3-methylbutyl-1, 2,2-dimethylpropyl-1, hexyl, 1-hexyl, 2-hexyl, 3-hexyl, 1-methylpentyl, 2-methylpentyl, 3-methyl-pentyl, 4-methylpentyl, 1,1-dimethylbutyl, 1,2-dimethyl-butyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-heptyl, 2-heptyl, 3-heptyl, 4-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propyl-butyl, 1-isopropylbutyl, octyl, 1-octyl, 2-octyl, 3-octyl, 4-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-propylpentyl or 2-propylpentyl.

The stated alkenyl radicals may be freely substituted, for example by 1–4 identical or different substitutents R$^{11}$, are preferably of 2 to 8 carbon atoms and are each, for example, ethenyl, 1-propenyl, 2-propenyl, butenyl, 1-butenyl, 2-butenyl, 3-butenyl, 1-methyl-2-propenyl, 2-methyl-2-propenyl, pentenyl, 1-pentenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, hexenyl, 1-hexenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2- butenyl, 1,1-dimethyl-3-butenyl, 1,2-dimethyl-2-butenyl, 1,2-dimethyl-3-butenyl, 1,3-dimethyl-2-butenyl 1,3-dimethyl-3-butenyl, 2,3-dimethyl-2-butenyl, 2,2-dimethyl-3-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenol or 1-ethyl-1-methyl-2-propenyl.

The stated alkynyl radicals may be freely substituted, for example by 1–4 identical or different substitutents $R^{11}$, are preferably of 2 to 8 carbon atoms and are each, for example, ethynyl, 1-propynyl, 2-propynyl, butynyl, 1-butynyl, 2-butynyl, 3-butynyl, 1-methyl-2-propynyl, pentynyl, 1-pentynyl, 2-pentynyl, 3-pentynyl, 4-pentynyl, 1-methyl-2-butynyl, 1-methyl-3-butynyl, 2-methyl-3-butynyl, 1,1-dimethyl-2-methyl-2-pentynyl, hexynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-2-methyl-2-propynyl.

The stated halogens are each fluorine, chlorine, bromine or iodine.

The stated cycloalkyl radicals may be freely substituted, for example by 1–4 identical or different substituents $R^{11}$, are preferably of 3 to 10 carbon atoms and are each, for example, cyclopropyl, cyclobutyl, cyclopentyl, cyclohexyl, cylcoheptyl, cyclooctyl, cyclononyl, cyclodecyl, bornanyl, norbornanyl, dicyclohexyl, bicyclo[3.3.0]octyl, bicyclo[3.2.1]octyl, bicyclo[2.2.2]-octyl or bicylco[3.3.1]nonyl.

The stated cycloalkynyl radicals may be freely substituted, for example by 1–4 identical or different substitutents $R^{11}$, are preferably of 6 to 12 carbon atoms and are each, for example, cyclohexyne, cycloheptyne, cyclooctyne, cyclononyne, cyclodecyne, cycloundecyne or cyclododecyne.

The stated haloalkyl radicals may be freely substituted, for example by 1–4 identical or different substituents $R^{11}$, are preferably of 1 to 8 carbon atoms and are each, for example, bromomethyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The stated haloalkoxy radicals may be freely substituted, for example by 1 to 4 identical or different substituents $R^{11}$, are preferably from 1 to 8 carbon atoms and are each, for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethory, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy.

The stated alkoxy or alkylthio radicals may be freely substituted, for example by 1 to 4 identical or different radicals $R^{11}$, and are preferably of 1 to 8 carbon atoms, and the alkyl groups of the alkoxy or alkylthio radicals have, for example, the same meanings as the alkyl groups stated above.

The stated aryl radicals may be freely substituted, for example by 1 to 4 identical or different substituents $R^{11}$, are preferably of 6, 10 or 14 carbon atoms and are each, for example, phenyl, 1-naphthyl, 2-naptithyl, 1-anthracenyl, 2-anthracenyl or 9-anthracenyl.

The stated hetaiyl radicals may be freely substituted, for example by 1 to 4 identical or different substitutents $R^{11}$, and are each, for example, furyl, 2-furyl, 3-furyl, thienyl, 2-thienyl, 3-thienyl, pyrrolyl, 1-pyrrolyl, 2-pyrrolyl, 3-pyrrolyl, isoxazolyl, 3-isoxazolyl, 4-isoxazolyl, 5-isoxazolyl, isothiazolyl, 3-isothiazolyl, 4-isothiazolyl, 5-isothiazolyl, pyrazolyl, 1-pyzrazolyl, 3-pyrazolyl, 4-pyrazolyl, 5-pyrazolyl, oxazolyl, 2-oxazolyl, 4-oxazolyl, 5-oxazolyl, thiazolyl, 2-thiazolyl, 4-thiazolyl, 5-thiazolyl, imidazolyl, 1-imidazolyl, 2-imidazolyl, 4-imidazolyl, 5-imidazolyl, 1,2,3-thiadiazolyl, 1,2,4-thiadiazolyl, 1,2,5-thiazolyl, 1,3,4-thiadiazolyl, tetrazolyl, 1,2,3,4-thiatriazolyl, 1,2,3,4-oxatriazolyl, pyridyl, 2-pyridyl, 3-pyridyl, 4-pyridyl, pyridazinyl, 3-pyridazinyl, 4-pyridazinyl, pyrimidinyl, 2-pyrimidinyl, 3-pyrimidinyl, 4-pyrimidinyl, 5-pyrimidinyl, pyrazinyl, 2-pyrazinyl, 3-pyrazinyl, 1,2,4-triazinyl, 1,3,5-triazinyl or 1,2,4,5-tetrazinyl.

Adjacent substituents of the heteroaromatic structures may be condensed to form an aromatic or heteroaromatic, saturated or partially unsaturated carbocyclic or heterocyclic ring which in turn may be substituted by 1 to 4 identical or different substituents $R^{11}$, so that hetaryl also includes fused ring systems, for example benzofuranyl, isobenzofuranyl, 1-benzothienyl, 2-benzothienyl, indolyl, isoindolyl, benzisoxazolyl, benzoxazolyl, benzisothiazolyl, benzithiazolyl, 2-benzothiazolyl, 4-benzthiazolyl, 5-benzthiazoly, 6-benzthiazolyl, 7-benzthiazolyl, inidazolyl, benzimidazolyl, benzthiazolyl, benzofurazanyl, dibenzofuranyl, dibenzothienyl, acridinyl, phenanthridinyl, carbazolyl, quinolyl, isoquinolyl, phthalazinyl, quinazolinyl, quinoxalinyl, cinnolyl, 1,5-naphthyridinyl, 1,6-naphthyridinyl, 1,7-naphthyridinyl, 1,8-naphthyridinyl, pteridinyl, pyrrolopyridinyl, pyrrolopyridazinyl, pyrrolopyrimidinyl, pyrrolopyrazinyl, pyrrolotriazinyl, furopyridinyl, furopyridazinyl, furopyrimidinyl, furopyrazinyl, furotriazinyl, thienopyridinyl, thienopyridazinyl, thienopyrimidinyl, thienopyrazinyl, thienotriazinyl, imidazopyridinyl, imidazopyridazinyl, imidazopyrimidinyl, imidazopyrazinyl, pyrazolopyridinyl, pyrazolopyridazinyl, pyrazolopyrimidinyl, pyrazolopyrazinyl, isoxazolopyridinyl, isoxazolopyridazinyl, isoxazolopyrimidinyl, isoxazolopyrazinyl, oxazolopyridinyl, oxazolopyridazinyl, oxazolopyrimidinyl, oxazolopyrazinyl, thiazolopyridinyl, thiazolopyridazinyl, thiazolopyrimidinyl, thiazolopyrazinyl, isothiazolopyridinyl, isothiazolopyridazinyl, isothiazolopyrimidinyl, isothiazolopyrazinyl, triazolopyridinyl, triazolopyridazinyl, triazolopyrimidinyl or triazolopyrazinyl.

The heteroaromatic ring

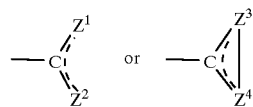

is, for example, furyl, thienyl, pyrrolyl, isoxazolyl, isothiazolyl, pyrazolyl, oxazolyl, thiazolyl, imidazolyl, 1,2,3-thiadiazolyl, 1,2,4-thiadiazolyl, 1,2,5-thiazolyl, 1,3,4-thiadiazolyl, 1,3,4-oxadiazolyl, pyridyl, pyridazinyl, pyrimidinyl, pyrazinyl, 1,2,4-triazinyl or 1,3,5-triazinyl, where the radicals having the group

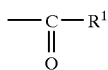

may, be present at any ring carbon atom of the heteroaromatic ring D.

2 adjacent substituents X or $R^{11}$ may be condensed to form an aromatic or heteroaromatic, saturated or partially unsaturated carbocyclic or heterocyclic ring which in turn may be substituted by 1 to 4 identical or different substituents $R^{11}$, so that the abovementioned heteroaromatic ring also includes fused ring systems, for example benzofuranyl, isobenzofuranyl, benzothienyl, indolyl, isoindolylt benzisoxazolyl, benzoxazolyl, benzisothiazolyl, indazolyl, benzimidazolyl, benzthiazolyl, benzofurazanyl, dibenzofuranyl, dibenzothienyl, acridinyl, phenanthridinyl, carbazolyl, quinolyl, isoquirolyl, phthalazinyl, quinazolyl, quinoxalinyl, cinnolyl, naphthridinyl, pteridinyl, pyrrolopyridinyl, pyrrolopyridazinyl, pyrrolpyrimidinyl, pyrrolopyrazinyl, pyrrolotriazinyl, furopyridinyl, furopyridazinyl, furopyrimidinyl, furopyrazinyl, furotriazinyl, thienopyridinyl, thienopyridazinyl, thienopyrimidinyl, thienopyrazinyl, thienotriazinyl, imidazopyridinyl, imidazopyridazinyl, imidazopyrimidinyl, imidazopyrazinyl, pyrazolopyridinyl, pyrazolopyridazinyl, pyrazolopyriaidinyl, pyrazolopyrazinyl, isoxazolopyridinyl, isoxaizolopyridazinyl, isoxazolopyrimidinyl, isoxazolopyrazinyl, oxazolopyridinyl, oxazolopyridazinyl, oxazolopyrimidinyl, oxazoiopyrazinyl, thiazolopyridinyl, thiazolopyridazinyl, thiazolopyrpyrazinyl, thiazolopyrazinyl isothiazolopyridinyl, isothiazolopyridazinyl, isothiazolopyrimidinyl, isothiazolopyrazinyl, triazolopyridinyl, triazolopyridazinyl, triazolopyrimidinyl or triazolopyrazinyl.

The stated heterocyclyl radicals are saturated or partially unsaturated, may be freely substituted, for example by 1 to 4 identical or different substituents $R^{11}$, and are each, for example, 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,2,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrothien-2-yl, 2,3-dihydrothien-3-yl, 2,5-dihydrothien-2-yl, 2,5-dihydrothien-3-yl, 2,4-pyrrolin-2-yl, 2,3-pyrrolin-3-yl, 2,5-pyrrolin-2-yl, 2,5-pyrrolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-3-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-2-yl, 3,4-dihydropyrazol-4-yl, 3,4-dihydropyrazol-5-yl, 4,5-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 3-tetrahydropyridazinyl, 4-tetrahydropyridazinyl, 2-tetrahydropyrimiidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, N-morpholinyl or dihydroquinazclinyl.

$R^{11}$ is freely substituted, for example by 1 to 4 identical or different substituents $R^{12}$, and is, for example, hydrogen, halogen, cyano, nitro, haloalkyl, alkyl, haloalkoxy, alkenyl, alkynyl, cycloalkyl, aryl, hetaryl, heterocyclyl, cycloalkenyl, alkoxy, alkenyloxy, alkynyloxy, cycloalkoxy, aryloxy, hetaryloxy, heterocyclyloxy, cycloalkenyloxy, alkoximino, alkenyloximino, alkynyloximino, cycloalkyloximino, cycloalkenyloximino, aryloxirmino, hetaryloximino, heterocyclyloximino, alkoxycarbconyl, alkenyloxycarbonyl, alkynyloxycarbonyl, cycloalkoxycarbonyl, aryloxycarbonyl, hetaryloxycarbonyl, heterocyclyloxycarbonyl, cycloalkenyloxycarbonyl, alkylaminocarbonyl, dialkylaminocarbonyl, alkenylaminocarbconyl, dialkenylaminocarbonyl, alkylthio, alkenylthio, alkynylthio, cycloalkylthio, arylthio, hetarylthio, heterocyclylthio, cycloalkenylthio, alkylamino, alkenylamino, alkynylamino, cycloalkylamino, arylamino, hetarylamino, heterocyclylamino, cycloalkenylamino, alkylcarbonyl, alkenylcarbonyl, alkynylcarbonyl, cycloalkylcarbonyl, arylcarbonyl, hetarylcarbonyl, heterocyclylcarbonyl, cycloalkenylcarbonyl, alkylsulfoxyl, alkenylsulfoxyl, alkynylsulfoxyl, cycloalkylsulfoxyl, arylsulfoxyl, hetarylsulfoxyl, heterocyclylsulfoxyl, cycloalkenylsulfoxyl, alkylsulfonyl, alkenylsulfonyl, alkynylsulfonyl, cycloalkylsulfonyl, arylsulfonyl, hetarylsulfonyl, heterocyclylsulfonyl, cycloalkenylsulfonyl, alkylsulfinyl, alkenylfinyl, alkynylsulfinyl, cycloalkylsulfinyl, arylsulfinyl, hetarylsulfinyl, heterocyclylsulfinyl, cycloalkenylsulfinyl, alkylcarbonylamino, alkenylcarbonylamino, alkynylcarbonylamino, amino, cycloalkylcarbonylamino, arylamino, hetarylamino or heterocyclylamino.

$R^{12}$ is freely substituted, and is, for example, hydrogen, halogen, cyano, nitro, haloalkyl, alkyl, haloalkoxy, alkenyl, alkynyl, cycloalkyl, aryl, hetaryl, heterocyclyl, cycloalkenyl, alkoxy, alkenyloxy, alkynyloxy, cycloalkoxy, aryloxy, hetaryloxy, heterocyclyloxy, cycloalkenyloxy, alkoximino, alkenyloximino, alkynyloximino, cycloalkyloximino, cycloalkenyloximino, aryloximino, hetaryloximino, heterocyclyloximino, alkoxycarbonyl, alkenyloxycarbonyl, alkynyloxycarbonyl, cycloalkoxycarbonyl, aryloxycarbonyl, hetaryloxycarbonyl, heterocyclyloxycarbonyl, cycloalkenyloxycarbonyl, alkylaminocarbonyl, dialkylaminocarbonyl, alkenylaminocarbonyl, dialkenylaminocarbonyl, alkylthio, alkenylthio, alkycnylthio, cycloalkylthio, arylthio, hetarylthio, heterocyclylthio, cycloalkenylthio, alkylamino, alkenylamino, alkynylamino, cycloalkylamino, arylamino, hetarylamino, heterocyclylamino, cycloalkenylamino, alkylcarbonyl, alkenylcarbonyl, alkynylcarbonyl, cycloalkylcarbonyl, arylcarbonyl, hetarylcarbonyl, heterocyclylcarbonyl, cycloalkenylcarbonyl, alkylsulfoxyl, alkenylsulfoxyl, alkynylsulfoxyl, cycloalkyleulfoxyl, arylsulfoxyl, hetarylsulfoxyl, heterocyclylsulfoxyl, cycloalkenylsulfoxyl, alkylsulfonyl, alkenylsulfonyl, alkynylsulfonyl, cycloalkylsulfonyl, arylsulfonyl, hetarylsulfonyl, heterocyclylsulfonyl, cycloalkenylsulfonyl, alkylsulfinyl, alkenylsulfinyl, alkynylsulfinyl, cycloalkylsulfinyl, arylsulfinyl, hetarylsulfinyl, heterocyclylsulfinyl, cycloalkenylsulfinyl, alkylcarbonylamino, alkenylcarbonylamino, alkynylcarbonylamino, amino, cycloalkylcarbonylamino, arylamino, hetarylamino or heterocyclylamino.

The novel compounds may be prepared, for example, by the following processes: The ketoesters 1 may be converted into the active ingredients 2 by a Wittig reaction with $(C_6H_5)_3P^+$—$CH_2$—O—$CH_3Cl^-$, $(C_6H_5)_3P^+$—$CH_3Hal^-$, $(C_6H_5)_3P^+$—$CH_2$—$R_5Hal$— (Hal=halogen (Cl, br or I)) or $(C_6H_5)_3P^+$—$CH_2$—$ClCl$— or by reaction with methoxyamine (Scheme 1).

$T^1$ is the substituted heteroaromatic ring

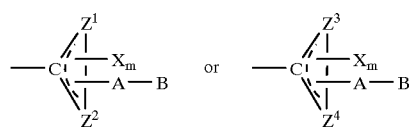

Scheme 1

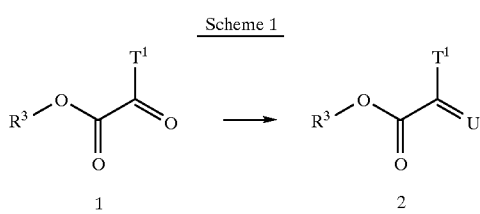

U=CH—$OR^2$, $CH_2$, CH—$R^2$, CH—CL or $NOR^2$ and $R^3$=alkyl

The thioenol ethers 4 are obtainable by reacting chlorovinyl derivatives 3 with thiols $R^1$-SH under alkaline conditions (Scheme 2).

Scheme 2

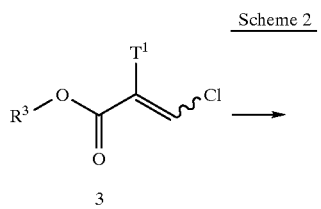

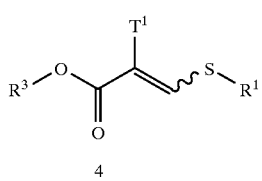

The amides 6 are obtainable from the esters 5 by reacting with amines $HNR^3R^4$. The esters 5 can also be reacted with carboxylic ester enolates (cf. for example E. Tao et al., Org. Prep. Proc. Int. Briefs 17 (1985), 235) to give the β-ketoesters 7 which, after decarboxylation with lithium chloride in dimethyl sulfoxide (cf. for example S. Takai et al., Tetrahedron Lett. 49 (1975), 43899, give the ketones 8 (Scheme 3).

Scheme 3

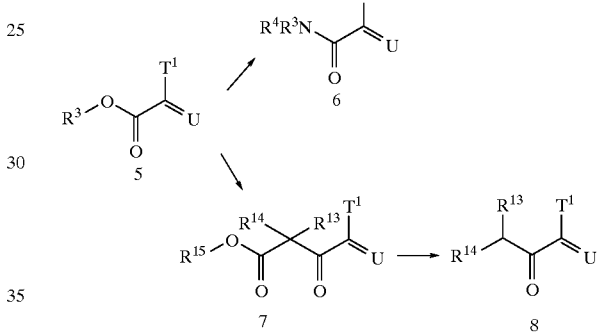

$R^{13}$ and $R^{14}$=H or $C_1$–$C_5$-alkyl $R^{15}$=$C_1$–$C_5$-alkyl

The α-ketoesters 2 can be prepared, for example, by the literature methods shown in Scheme 4 or further literature methods (cf. for example L. Weinstock et al., Synthetic Communications 11 (1981), 943–946; J. March, Advanced Organic Chemistry, 3rd Edition 1985, J. Wiley & Sons; R. Larock, Comprehensive Organic Transformations, 1st Edition 1989, VCH Publishers; M. Fieser, Reagents for Organic Synthesis, J. Wiley & Sons; S. Patai, The Chemistry of Acid Derivatives, J. Wiley & Sons).

Scheme 4

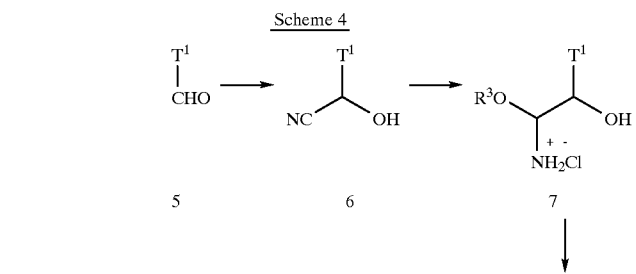

-continued

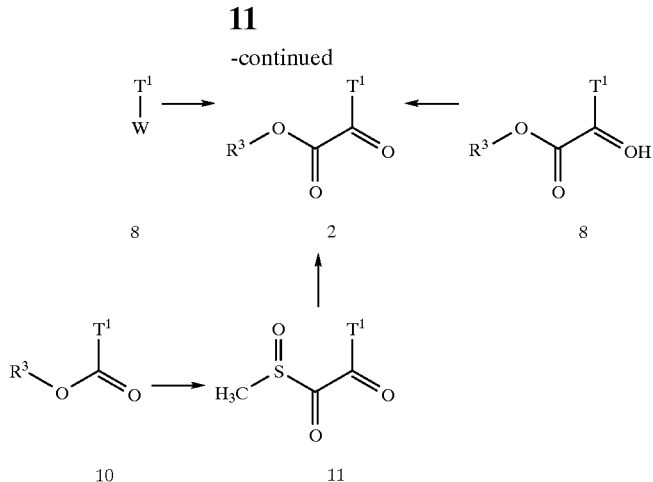

For example, the α-ketoesters 2 can be prepared by reacting the corresponding heteroaromatics 9 (W=hydrogen) with oxalates or oxalic ester halides or imidazolides in the presence of acidic (eg. AlCl$_3$, TiCl$_4$, SnCl$_4$, ZnCl$_2$ or FeCl$_3$, similarly to EP 385357) or basic (eg. pyridine, triethylamine, ethyldiisopropylamine, lithium diisopropylamide or butyllithium) catalysts. Furthermore, the heteroaromatics 9 (W=hydrogen or halogen) can be reacted with Mg, Li, butyllithium, lithium diisopropylamide or lithium tetramethylpiperidide (similarly to EP 253213) to give the corresponding metallized heteroaromatics, which can then be converted into the α-ketoesters 2 with oxalates, oxalic ester halides or oxalic ester imidazolides. Moreover, the cyanohydrins 6 can be obtained by subjecting HCN to an addition reaction with the aldehydes 5. The cyanohydrins 6 can then be converted with HCl and methanol into the imictoester hydrochlorides 7, which can then be hydrolyzed to the α-hydroxyesters 8. The α-ketoesters 2 are then obtained by oxidation of the α-hydroxyesters 8 (similarly to EP 422597).

Furthermore, the esters 10 can be reacted with dimethyl sulfoxide under alkaline conditions to give the β-ketosulfoxides 11. The β-ketosulfoxides 11 are then converted into the α-ketoesters 2 by reaction with bromine and subsequently with hydrochloric acid in the presence of an alcohol R$^3$—OH in a Pummerer reaction (cf. for example J. Amer. Chem. Soc. (1966), 5498; Synthesis (1982), 41).

The enol ethers 12 can be prepared, for example, by reacting the corresponding heteroaromatically substituted acetic ester derivatives 13 under alkaline conditions with formates (similarly to Organikum, 15th Edition 1976, page 548, VEB) and subsequently alkylating the resulting enolate. The enol ethers 12 can also be prepared by eliminating R$^2$—OH (similarly to T. Yamada et al., J. Chem. Soc. Chem. Commun. (1980), 838 and the literature cited there) from the acetals 14 (similarly to T. Mukaiyama et al. Chem. Lett. (1976), 769).

Alternatively, the acrylates 15 may further be converted into the acrylates 12 by successive reaction with bromine, an alcoholate R$^2$—O—M (M=Na, K, Li or Mg) and a protic acid, eg. NAHSO$_4$ (similarly to G. Shaw et al., J. Chem. Soc. (1958), 153 and the literature cited there) (Scheme 5).

Scheme 4

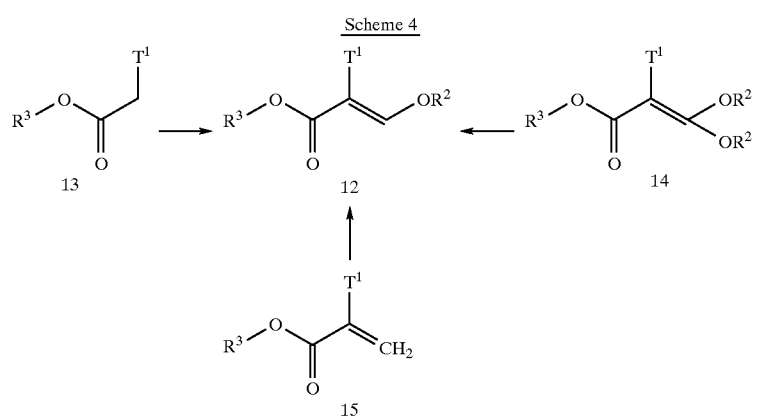

Important intermediates for synthesis of the heteroaromatic compounds as claimed in claim 1 are oxime ethers 19 and 20, which can be prepared by nitrosation/alkylation of the β-ketoesters 16 to give the oxime ethers 18 and subsequent reaction of 18 with halogen (Hal, Cl$_2$ or Br$_2$) or dimethylformamide dimethyl acetal (DMF-DMA) (Scheme 6).

Scheme 6
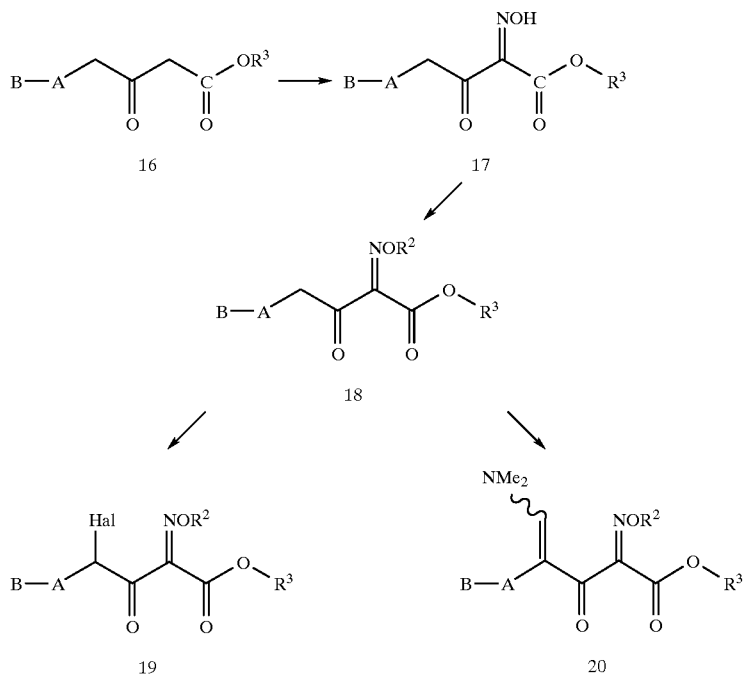
The α-halocarbonyl compounds 19 can then be cyclized to thiazoles 21 (similarly to M. Tomlinsen, J. Chem. Soc. (1935), 1030), imidazoles 22 (similarly to H. Brederck et al., Chem. Ber. 86 (1953), 88 or oxazoles 23 (similarly to Z. Itov et al., Khim.-farm. Zh. 23 (1989), 452; Scheme 7).
Scheme 7
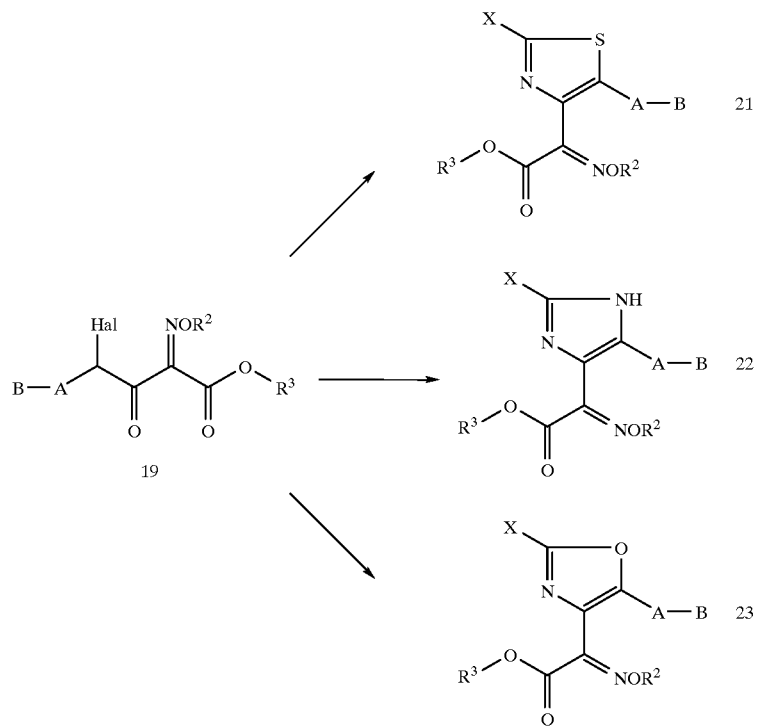

The enamines 20 can be converted into isoxazoles 24 (similarly to P. Schenone, J. Heterocyci. Chem. 20 (1983), 645), pyrazoles 25 (J. Heterocyci. Chem. 14 (1977), 345) or pyrimidines 26 (Scheme 8).

oximation of the α, γ-diketoesters 27 (prepared similarly to Organikum, 15th Edition 1976, page 584) to give the oxime ethers 28 and subsequent halogenation (Hal =Cl or Br) or by reaction of the compounds 28 with dimethylformamide

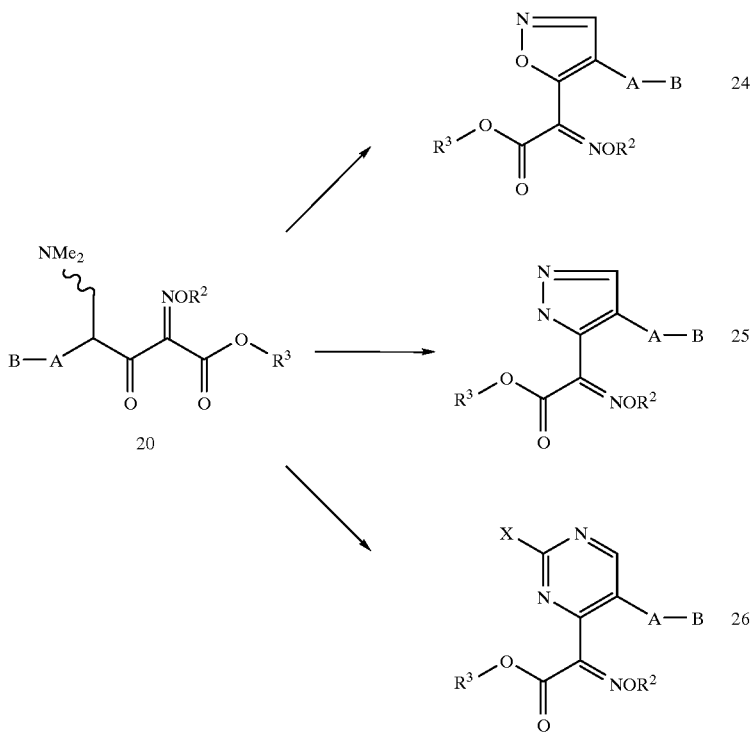

Further important intermediates for the synthesis of the heteroaromatic compounds as claimed in claim 1 are the oxime ethers 29 and 30, which can be prepared by selective dimethyl acetal (DMF-DMA) (Scheme 9).

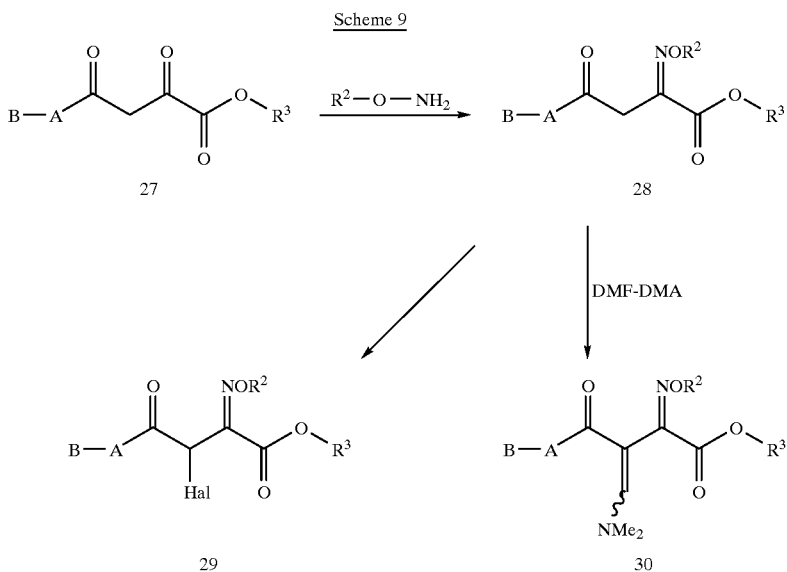

The α-halocarbonyl compound 29 can then be converted into thiazoles 31, imidazoles 32, oxazoles 33 or furans 34 (similarly to Winberg et al., J. Amer. Chem. Soc. 82 (1960), 1428 (Scheme 10, cf. Scheme 7). Scheme 10
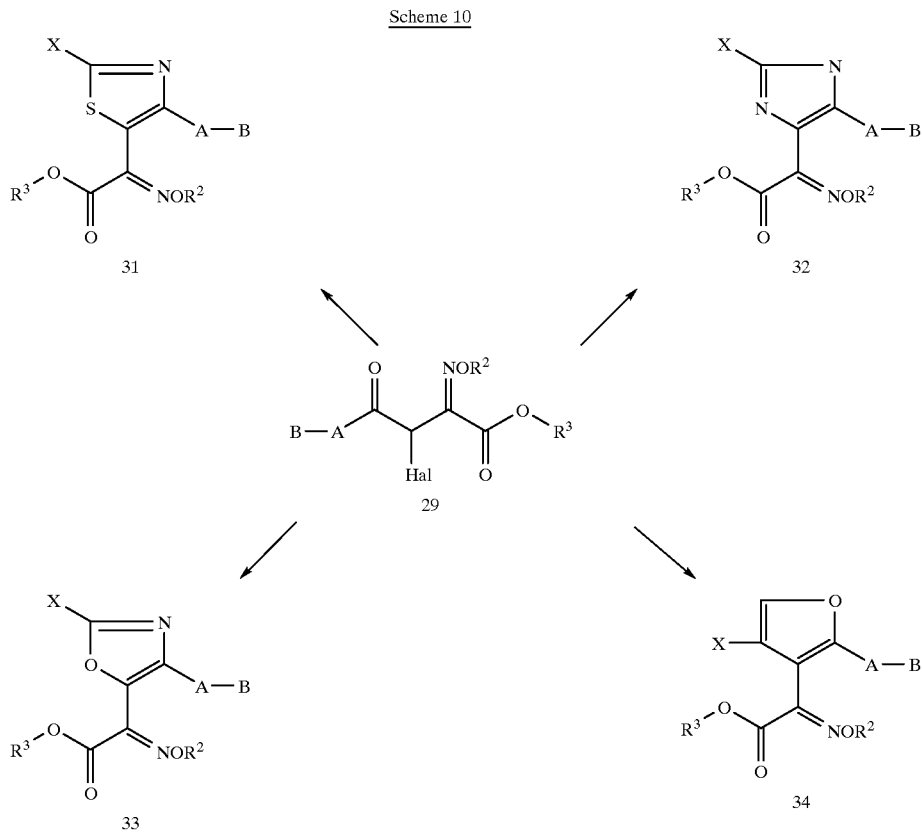
The enamine 30 can then be converted into the isoxazoles 35, pyrazoles 36 or pyrimidines 37 (Scheme 11, cf. Scheme 8).
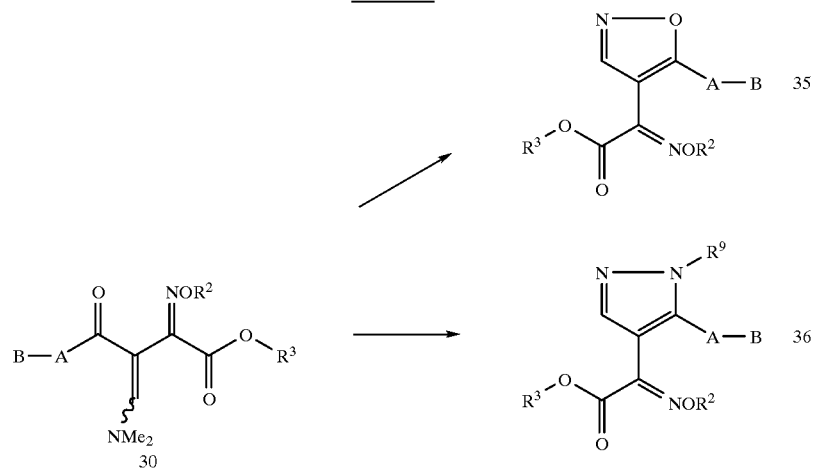

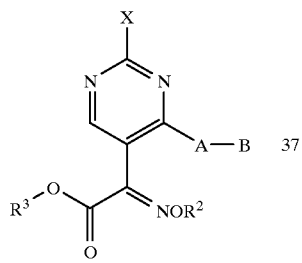

In addition, isoxazoles such as 41 are obtainable from the pyruvic acid derivative 38. 38 is oxildized with N-methylmorpholine N-oxide to the aldehyde 39, which is converted with hydroxylamine into the oxime 40. The latter reacts with acetylenes in the presence of NaOCl to give the isoxazole 41 (Scheme 12).

Scheme 12

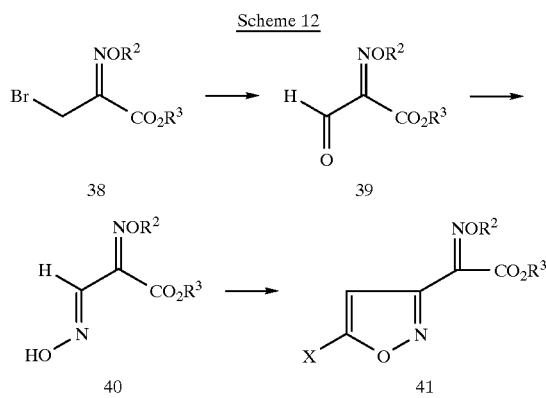

The heteroaromatic compounds 45 can be prepared by reacting the halides 44 (Hal=Cl or Br) with the corresponding nucleophiles. The bromides 44 are obtained by free radical halogenation of the heteroaromatic compounds 42 or by ether cleavage of the methyl ether 43 (Scheme 13).

-continued

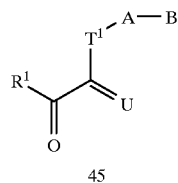

A:  —CH($R^5$)—O—N=C($R^6$)—, —CH($R^5$)—O—N=,
—CH($R^5$)—S—, —CH($R^5$)—O—, —CH($R^5$)—N$R^7$—,
—CH($R^5$)—O—C(=O)—

The heteroaromatic compounds 48 can be prepared by reacting the carbonyl compounds 47 with oxime ethers $H_2N$—O—B or azines $H_2N$—N=B or by a Wittig reaction with the corresponding phosphonium salts, phosphonates or phosphonium oxides. The carbonyl compounds 47 are obtained by oxidizing the halides 42 with N-methylmorpholine N-oxide or by hydrolysis of the dihalides 46 under catalysis by a heavy metal salt (Scheme 14). The dihalides 46 are obtainable by free radical halogenation of the monohalides 44 or by free radical dihalogenation of the heteroaromatic compounds 42.

Scheme 14

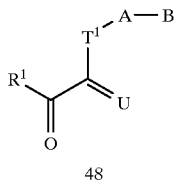
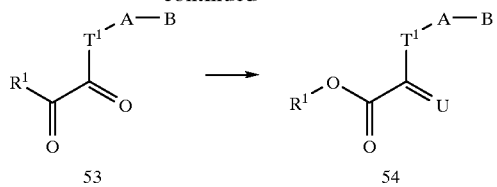

A: —C(R⁵)=N—O—, —C(R⁵)=N—N= or —C(R⁵)=C(R⁷)—

Alternatively, the halides 42 can be converted into the corresponding phosphorus compounds 49 (phosphonium salts, phosphonates or phosphine oxides) and then with carbonyl compounds in a Wittig reaction to the corresponding olefins (Scheme 15).

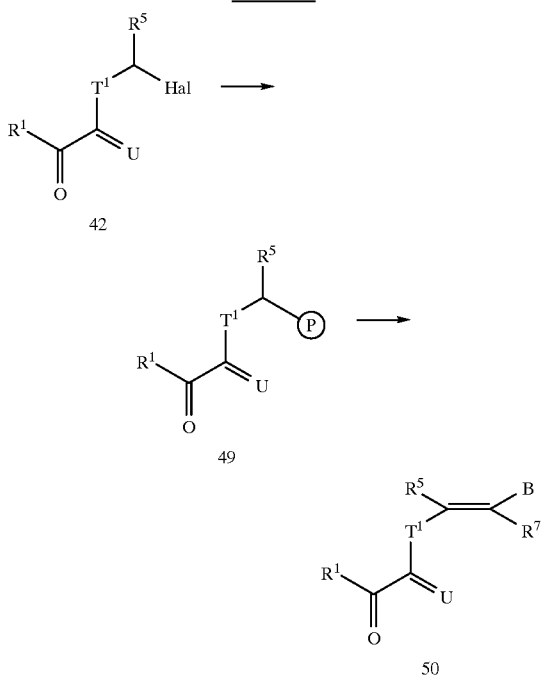

Moreover, the ketoesters 51 can be halogenated in the side chain (Hal=Cl or Br) and then reacted with the corresponding nucleophiles to give the heteroaromatic compounds 53. The novel compounds 54 are then obtainable from the ketoesters 53 similarly to Scheme 1 (Scheme 16).

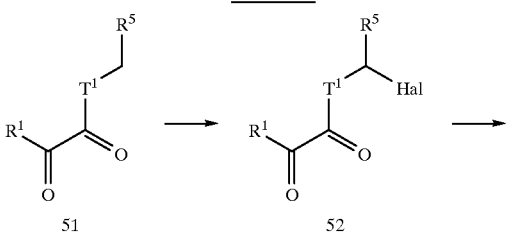

The Examples which follow illustrate the preparation of the novel compounds.

EXAMPLE 1

Methyl β-methoxy-α-(N-phenylpyrazol-4-yl)-acrylate (Table 3, No. 7 and 8)

a) Methyl α-hydroxy-α-(N-phenylpyrazol-4-yl)-acetate

A mixture of 63 g (0.37 mol) of N-phenylpyrazol-4-carbaldehyde in 300 ml of diethyl ether and 58 g (0.9 mol) of KCN and 48 g (0.9 mol) of NH₄Cl in 300 ml of water is stirred overnight at room temperature (20° C.). The phases are separated and the aqueous phase is extracted with diethyl ether. The combined organic phases are dried over MgSO₄ and evaporated down. The residue is purified by column chromatography using 4:1 hexane/ethyl acetate. 50 g of the cyanohydrin having a purity of 70% are obtained, the cyanohydrin being directly reacted further.

The cyanohydrin is dissolved in 200 ml of methanol, 150 ml of 2 N HCl in ether are added and stirring is carried out overnight at room temperature. The reaction mixture is then evaporated down, 200 ml of water are added and stirring is carried out for 1 hour at 80° C. The mixture is cooled to room temperature and is extracted three times with methylene chloride. The combined organic phases are dried over MgSO₄ and evaporated down. The residue is purified by column chromatography using hexane/ethyl acetate mixtures. 16 g (66 ummol, 18%) of the title compound are obtained as a yellow oil.

¹H-NMR (CDCl₃; δ in ppm): 7.95 (s, 1H, pyrazolyl); 7.75 (s, 1H, pyrazolyl); 7.65 (d, 2H, J=8 Hz, phenyl); 7.4 (t, 2H, J=8 Hz, phenyl); 7.3 (t, broad, 1H, phenyl); 5.3 (s, broad, 1H, CH—O); 3.85 (s, 3H, OCH₃); 3.7 (s, broad, 1H, OH)

b) Methyl α-keto-α-(N-phenylpyrazol-4-yl)-acetate 160 g (0.57 mol) of 26% strength NaOCl solution are added dropwise at 20–30° C. to a mixture of 22 g (87 mmol) of the α-hydroxyester from Example 1a) in 50 ml of CH₂Cl₂ and 0.6 g of KBr, 1.2 g of NaH₂PO₄, 1.7 g of Na2HPO₄ and 50 mg of tetramethylpiperidin-N-oxyl in 50 ml of water. Stirring is carried out for 30 minutes at room temperature, the phases are separated off and the aqueous phase is extracted three times with CH₂Cl₂. The combined organic phases are dried over MgSO₄ and evaporated down. The residue is purified by column chromatography using hexane/ethyl acetate mixtures. 15.5 g (62 mmol, 71%) of the title compound are obtained as a colorless solid.

¹H-NMR (CDCl₃; δ in ppm): 8.8 (s, 1H, pyrazolyl); 8.4 (s, 1H, pyrazolyl); 7.75 (d, 1H, J=8 Hz, phenyl); 7.5 (t, 2H, J=8 Hz, phenyl); 7.4 (t, broad, 2H, phenyl); 4.0 (s, 3H, O—CH₃)

c) Methyl α-keto-α-(N-phenylpyrazol-4-yl)-acrylate (Table 3, No. 7 and 8)

2.1 g (19 mmol) of potassium tert-butylate are added a little at a time at 0° C. to 8.5 g (25 mmol) of methoxymethyltriphenylphosphonium chloride in 50 ml of tetrahydrofuran. The red reaction mixture is stirred for 15 minutes at 0° C., 4 g (16 mmol) of the ketoester from Example 1b), dissolved in 10 ml of tetrahydrofuran, are added and stirring is carried out for about 3 hours at room temperature. After the end of the reaction, the reaction mixture is diluted with water and the aqueous phase is extracted three times with diethyl ether. The combined ether phases are dried over MgSO$_4$ and evaporated down. The residue is purified by column chromatography using hexane/ethyl acetate mixtures. 1.3 g (4.7 mmol, 29%) of the trans-isomer and 2.0 g (7.2 mmol, 45%) of the cis-isomer of the title compound are obtained as pale yellow oils.

$^1$H-NMR (CDCl$_3$; δ in ppm): trans-Isomers: 8.4 (s, 1H, pyrazolyl); 8.2 (s, 1H, pyrazolyl); 7.7 (d, broad, 2H, pnenyl); 7.5 (s, 1H, vinyl); 7.4 (t, 1H, J=8 Hz, phenyl); 7.25 (t, broad, 1H, phenyl); 4.0 (s, 3H, O—CH$_3$); 3.8 (s, 3H, O—CH$_3$) cis-Isomers: 8.05 (s, 1H, pyrazolyl); 7.65 (m, 3H, pyrazolyl, 2 x phenyl); 7.45 (t, 2H, J=8 Hz, phenyl); 7.25 (t, broad, 1H, phenyl); 6.9 (s 1H, vinyl); 3.95 (s, 3H, O—CH$_3$); 3.8 (s, 3H, O—CH$_3$)

EXAMPLE 2

α-(N-Phenylpyrazol-4-yl)-crotonate (Table 3, No. 9)

2 g (18 mmol) of potassium tert-butylate are added a little at a time to 12.5 g (30 mmol) of ethyltripheniylphosphonium iodide in 50 ml of tetrahydrofuran at room temperature. The orange reaction mixture is stirred for 30 minutes, after which 3.7 g (15 mmol) of the ketoesters from Example 1b) and 0.5 ml of methanol are added. After 1 hour, NH$_4$Cl solution is added and the aqueous phase is extracted three times with diethyl ether. The combined organic phases are dried over MgSO$_4$ and evaporated down. The residue is purified by column chromatography using hexane/ethyl acetate mixtures. 1.3 g (5 mmol, 33%) of the title compound (cis/trans= 1:1) are obtained as a pale yellow oil.

$^1$H-NMR (CDCl$_3$; δ in ppm): 8.05, 8.02 (2 s, 1H, pyrazolyl); 7.6–7.8 (m, 3H, pyrazolyl), 2 x phenyl); 7.45 (m, 2H, phenyl); 7.3 (m, 1H, phenyl); 7.15 (q, 1H of the trans-isomer, J=9 Hz; vinyl); 6.5 (q, 1H of the cis-isomer, J=9 Hz, vinyl); 3.85, 3.8 (2 s, 3H, O—CH$_3$); 2.1, 2.0 (2 d, 3H, J=9 Hz, CH$_3$)

EXAMPLE 3

Methyl α-keto-α-(5-methylthiazol-4-yl)-acetate O-methyloxime (Table 3, No. 146 and 147)

a) Methyl β-keto-α-methoximinovalerate 300 g (5 mol) of acetic acid is added at 10° C. in the course of 1 hour to 500 g (3.84 mol) of methyl β-ketovalerate and 310 g (4.5 mol) of NaNO$_2$ in 2 l of water. The cooling bath is then removed, the reaction temperature increasing to about 40° C. The reaction mixture is allowed to cool to room temperature and is extracted three times with methylene chloride. The combined organic phases are extracted with NAHCO$_3$ solution, dried over MgSO$_4$ and evaporated down. The residue thus obtained is dissolved in 2 l of acetone, 600 g (4.3 mol) of K$_2$CO$_3$ are added a little at a time and 600 g (4.6 mol) of methyl iodide are then added dropwise. Stirring is carried out overnight at room temperature, the insoluble solid is filtered off under suction and the filtrate is evaporated down. The residue is distilled under reduced pressure, and 390 g (2.25 mol, 59%) of the title compound is obtained as a pale yellow liquid (bp. (25 mbar) =100–104° C.).

$^1$H-NMR (CDCl$_3$; δ in ppm): 4.1 (s, 3H, O—CH$_3$); 3.9 (s, 3H, O—CH$_3$); 2.8 (q, 2H, J=8 Hz, CH$_2$); 1.1 (t, 3H, CH$_3$)

b) Methyl γ-bromo-β-keto-α-methoximinovalerate 380 g (2.38 mol) of bromine are added dropwise at about 25° C. to 400 g (2.3 mol) of the ketone from Example 3 a) in 1 l of acetic acid. Stirring is carried out for 30 minutes, the reaction mixture is diluted with water and the aqueous phase is extracted three times with methylene chloride. The combined organic phases are washed neutral with NaHCO$_3$ solution, dried over MgSO$_4$ and evaporated down. 560 g (2.22 mol, 97%) of the title compound in the form of a yellow oil are obtained as the residue.

$^1$H-NER (CDCl$_3$; δ in ppm): 5.25 (q, 1H, J=7 Hz, CHBr); 4.15 (s, 1H, O—CH$_3$); 3.9 (s, 3H, O—CH$_3$); 1.8 (d, 3H, CH$_3$)

c) Methyl α-keto-α-(5-methylthiazol-4-yl)-acetate O-methyloxime (Table 3, No. 146 and 147)

200 g of thioformamide (purity about 70%, about 2.3 mol) are added a little at a time to 560 g (2.2 mol) of the α-bromoketone from Example 3b) in 2 l of methanol, the reaction temperature being kept at about 30° C. with a cooling bath. Stirring is carried out overnight at room temperature, a further 30 g of thioformamide are added and stirring is continued for 5 hours at 40° C. The reaction mixture is then evaporated down and the residue is taken up in methylene chloride. The organic phase is washed neutral with NaHCO$_3$ solution, dried over MgSO$_4$ and evaporated down. The residue is purified by column chromatography using hexane/ethyl acetate mixtures. 233 g of the cis-isomer and 190 g of the trans-isomer (polar isomer) of the title compound, each highly impure, are obtained. Distillation under greatly reduced pressure gives 106 g (0.49 mol, 23%) of the cis-isomer as a pale yellow oil. Crystallization with methyl tert-butyl ether and hexane gives 71 g (0.33 mol, 15%) of the trans-isomer (colorless crystal; mp.=65° C.) of the title compound.

$^1$H-NMR (CDCl$_3$; δ in ppm): cis-Isomer: 8.6 (s, 1H, thiazolyl); 4.05 (s, 3H, O—CH$_3$); 3.95 (s, 3H, O—CH$_3$); 2.7 (s, 3H, CH$_3$) trans-isomer; 8.65 (s, 1H, thiazolyl); 4.1 (s, 3H, O—CH$_3$); 3.9 (s, 3H, O—CH$_3$); 2.4 (s, 3H, CH$_3$)

EXAMPLE 4

Methyl α-keto-α-(5-bromomethylthiazol-4-yl)-acetate O-methyloxime (Table 3, No. 148 and 149)

A mixture of 106 g (0.5 mol) of the methylthiazol (cis-isomer from Example 3c), 100 g (0.56 mol) of N-bromosuccinimide and 1 g of azobisisobutyronitrile in 1 l of carbon tetrachloride is refluxed for 3 hours. 20 g (0.11 mol) of N-bromosuccinimide are also added and heating is carried out for a further 2 hours. The reaction mixture is cooled to room temperature and the precipitated succinimide is filtered off under suction. The filtrate is extracted with water, dried over MgSO$_4$ and evaporated down. The residue is purified by column chromatography using hexane/ethyl acetate mixtures. The products brominated in the nucleus and polybrominated products are obtained in the first fraction, followed by 58 g of the cis-isomer (about 90% purity; 0.18 mol, 36%) and 11 g of the trans-isomer (about 90% purity, 34 mmol, 7%) of the title compound as yellow oils.

$^1$H-NMR (CLCl$_3$; δ in ppm) : cis-Isomer: 7.75 (s, 1H, thiazolyl); 5.0 (s, 2H, CH$_2$Br); 4.1 (s, 3H, O—CH$_3$) trans-isomer: 8.85 (s, 1H, thiazolyl); 4.55 (s, 2H, CH$_2$Br); 4.1 (s, 3H, O—CH$_3$); 3.9 (s, 3H, O—CH$_3$)

EXAMPLE 5

Methyl α-keto-α-(5-(4'-(acetyl-O-isopropyloxime)-2'-methylphenoxymethyl)-thiazol-4-yl)-acetate O-methyloxime (Table 3, No. 150 and 151)

0.9g (40 mmol) of sodium hydride is added a little at a time to 7 g (30 mmol) of 4-acetyl-2-methylphenol O-isopropyloxime in 25 ml of dimethylformamide. After the evolution of gas has ceased, 10 g (30 mmol) of the bromomethylthiazol from Example 4 are added a little at a time, and stirring is carried out for 2 hours at room temperature. Thereafter, the reaction mixture is diluted with water and the aqueous phase is extracted three times with methyl tert-butyl ether. The combined organic phases are dried over $MgSO_4$ and evaporated down. 10.6 g of the cis-methyloxime isomer of the title compound are obtained as the residue. The residue is dissolved in 120 ml of methylene chloride and 20 ml of 2 N HCl in ether are added. Stirring is carried out for 2 days at room temperature, and the organic phase is washed neutral with $NaHCO_3$ solution, dried over $MgSO_4$ and evaporated down. The residue is purified by column chromatography using hexane/ethyl acetate mixtures. 2.2 g (5.2 mmol, 18%) of the cis-isomer (mp.=107° C.) and 5.8 g (14 mmol, 46%) of the trans-isomer (mp.=87° C.) of the title compound are obtained as colorless solids.

$^1$H-NMR ($CDCl_3$; δ in ppm): cis-Isomer: 8.75 (s, 1H, thiazolyl); 7.55 (s, broad, 1H, phenyl); 7.45 (d, broad, 1H, phenyl); 6.8 (d, 1H, J=8 Hz, phenyl); 5.5 (s, 2H, O—$CH_2$); 4.45 (m, 1H, O—CH($Me_2$)); 4.05 (s, 3H, O—$CH_3$); 4.0 (s, 3H, $OCH_3$); 2.3 (s, 3H, $CH_3$); 2.2 (s, 3H, $CH_3$); 1.3 (d, 6H, J=7 Hz, CH($CH_3$)$_2$) trans-isomer: 8.8 (s, 1H, thiazolyl); 7.5 (s, broad, 1H, phenyl); 7.4 (d, broad, 1H, phenyl); 6.25 (d, 1H, J=8 Hz, phenyl); 5.15 (s, 2H, O—$CH_2$); 4.45 (m, 1H, O—CH($Me_2$); 4.1 (s, 3H, O—$CH_3$); 3.9 (s, 3H, O—$CH_3$); 2.25 (s, 3H, $CH_3$); 2.2 (s, 3H, $CH_3$); 1.3 (d, 6H, J=7 Hz, CH($CH_3$)$_2$)

EXAMPLE 6

N-Methyl-α-keto-α-(5-(4'-(acetyl-O-isopropyloxime)-2'-methylphenoxymethyl)-thiazol-4-yl)-acetamide trans-O-methyloxime (Table 3, No. 152)

A suspension of 2 g (4.8 mmol) of the transmethyloxime from Example 5 in 10 ml of 40% strength methylamine solution is stirred for 2 hours at 50° C. The insoluble solid is filtered off under suction and the residue is washed with acetone. Recrystallization of the solid from ethyl acetate/hexane gives 1 g (2.4 mmol, 50%) of the title compound as a colorless solid (mp.=147° C.).

$^1$H-NMR ($CDCl_3$; δ in ppm): 8.85 (s, 1H, thiazolyl); 7.5 (s, broad, 1H, phenyl); 7.4 (d, broad, 1H, phenyl); 7.95 (s, broad, 1H, NH); 6.75 (d, 1H, J=8 Hz, phenyl); 5.2 (s, 2H, O—$CH_2$); 4.45 (m, 1H, O—CH($Me_2$)); 4.05 (s, 3H, O—$CH_3$); 2.95 (d, 3H, J=5 Hz, N—$CH_3$); 2.25 (s, 3H, $CH_3$); 2.2 (s, 3H, $CH_3$); 1.3 (d, 6H, J=6 Hz, O—C($CH_3$)$_2$)

EXAMPLE 7

Methyl α-keto-α-(4-methylisoxazol-5-yl)-acetate O-methyloxime (Table 3, No. 153 and 154)
a) Methyl δ-dimethylamino-β-keto-α-methoximino-γ-methylpent-4-enoate 70 g (0.69 mol) of acetic anhydride are added dropwise to a mixture of 100 g (0.578 mol) of the ketone from Example 3a and 75 g (0.91 mol) of sodium acetate in 200 ml of dimethylformamide dimethyl acetal. The temperature of the reaction mixture was allowed to increase to about 65° C. After a short time, the reaction temperature decreases, after which the content of the flask is heated to about 75° C. and stirred for about 2 hours. Thereafter, the volatile components are stripped off, initially at 25 mbar and then under greatly reduced pressure. The residue is taken up in methylene chloride and the organic phase is washed four times with water, dried over $MgSO_4$ and evaporated down. 146 g (containing about 10% of dimethylformamide; quantitative yield) of the title compound in the form of a brown oil are obtained as the residue.

$^1$H-NMR ($CDCl_3$; δ in ppm): 7.5 (s, 1H, vinyl); 4.0 (s, 3H, O—$CH_3$); 3.9 (s, 3H, O—$CH_3$); 3.2 (s, 6H, N($CH_3$)$_2$); 2.05 (s, 3H, =C—$CH_3$)

b) Methyl α-keto-α-(4-methylisoxazol-5-yl)-acetate O-methyloxime (Table 3, No. 153 and 154)

146 g (0.57 mol) of the enaminoketone from Example 7 a and 60 g (0.86 mol) of hydroxylamine hydrochloride in 300 ml of acetic acid are stirred for 5 hours at 60° C. and then overnight at room temperature. The reaction mixture is evaporated down, the residue is taken up in methylene chloride and the undissolved solid is filtered off under suction. The filtrate is washed with $Na_2CO_3$ solution and water, dried over $MgSO_4$ and evaporated down. The residue is stirred thoroughly with a methyl tert-butyl ether/hexane mixture and filtered off under suction. 20 g (0.1 mol, 18%) of the cis-isomer of the title compound are obtained as the residue. The filtrate is evaporated down and purified by column chromatography using hexane/ethyl acetate mixtures. 32 g (0.16 mol, 28%) of the title compound are obtained as a cis/trans mixture (about 2:1).

$^1$H-NMR ($CDCl_3$; δ in ppm); cis-Isomer: 8.18 (s, 1H, isoxazolyl); 4.1 (s, 3H, O—$CH_3$); 3.94 (s, 3H, O—$CH_3$); 2.2 (s, 3H, $CH_3$) transisomer: 8.19 (s, 1H, isoxazolyl); 4.2 (s, 3H, O—$CH_3$); 3.9 (s, 3H, O—$CH_3$); 2.0 (s, 3H, $CH_3$)

EXAMPLE 8

Methyl α-keto-α-(4-bromomethylisoxazol-5-yl)-acetate O-methyloxime (Table 3, No. 155 and 156) and methyl α-keto-α-(4-dibromomethylisoxazol-5-yl)-acetate O-methyloxime (Table 3, No. 157 and 158)

A mixture of 25 g (0.12 mol) of the cis-methoximinomzethylisoxazol from Example 7 b, 25 g (0.14 mol) of N-bromosuccinimide and 0.5 g of azobisisobutyronitrile in 150 ml of methylene chloride is exposed for 5 hours to a 300 W UV lamp, the reaction mixture being refluxed. Thereafter, the reaction mixture is cooled to room temperature and is extracted three times with water. The organic phase is then dried over $MgSO_4$ and evaporated down. The residue is purified by column chromatography using hexane/ethyl acetate mixtures. 3.8 g (10.7 mmol, 9%) of the cis-dibromide, 10 g (29 mmol, 24%) of the cis-bromide (purity about 80%), 4 g (11 mmol, 9%) of the trans-dibromide and 14 g (51 mmol, 42%) of the trans-bromide (mp.=45° C.) of the corresponding title compound are obtained.

$^1$H-NMR ($CDCl_3$; δ in ppm): cis-Dibromide: 8.7 (s, 1H, isoxazolyl); 6.95 (s, 1H, $CHBr_2$); 4.2 (s, 3H, O—$CH_3$); 3.95 (s, 3H, O—$CH_3$); cis-bronmide: 8.4 (s, 1H, isoxazolyl); 4.55 (s, 2H, $CH_2Br$); 4.15 (s, 3H, O—$CH_3$); 4.0 (s, 3H, O—$CH_3$) trans-dibromide: 8.65 (s, 1H, isoxazolyl); 6.45 (s, 1H, $CHBr_2$; 4.25 (s, 3H, O—$CH_3$; 3.95 (s, 3H, O—$CH_3$) trans-bromide; 8.4 (s, 1 H, isoxazolyl; 4.25 (s, 2H, $CH_2Br$); 4.23 (s, 3H, O—$CH_3$); 3.95 (s, 3H, O—$CH_3$)

EXAMPLE 9

Methyl α-keto-β-(4-formylisoxazol-5-yl)-acetate trans-O-methyloxime (Table 3, No. 159)

A solution of 35 g (0.21 mol) of $AgNO_3$ in 200 ml of water is added to 35.5 g (0.1 mol) of the trans-dibromide from Example 8 in 300 ml of methanol. Stirring is carried out for 2 hours at room temperature, the precipitated solid is filtered off under suction and the reaction mixture is evaporated down. The residue is taken up in methyl tert-butyl ether and the solution is extracted with water, NaHCO$_3$ solution and water. The organic phase is dried over MgSO$_4$ and evaporated down. The crysytalline residue is stirred with methyl tert-butyl etherihexane and filtered off under suction. 15.8 g (75 mmol, 75%) of the title compound is obtained as a colorless solid.

$^1$H-NMR (CDCl$_3$; δ in ppm): 9.85 (s, 1H, CHO); 8.7 (s, 1H, isoxazolyl); 4.25 (s, 3H, O—CH$_3$); 3.95 (s, 3H, O—CH$_3$)

EXAMPLE 10

Methyl β-keto-β-(4-(2'-o-methylphenyl-trans-ethen-1'-yl)-isoxazol-5-yl)-acetate trans-O-methyloxime (Table 3, No. 124)

4.5 g (40 mmol) of potassium tert-butylate are added a little at a time at room temperature to 20 g (50 mmol) of o-methylbenzyltriphenylphosphonium chloride in 200 ml of tetrahydrofuran. Stirring is carried out for 30 minutes, the mixture is cooled to −30° C. and 6.3 g (30 mmol) of the trans-O-methyloxime aldehyde from Example 9, dissolved in tetrahydrofuran, are added. The mixture is then allowed to warm up slowly to room temperature and is stirred for a further 4 hours at this temperature. The reaction mixture is then diluted with water and the aqueous phase is extracted three times with methylene chloride. The organic phase is dried over MgSO$_4$ and evaporated down, triphenylphosphine oxide crystallizing out. The residue is stirred thoroughly with methyl tert-butyl ether and the insoluble solid is filtered off under suction. The filtrate is evaporated down, the residue is crystallized and the crystals are stirred thoroughly with methyl tert-butyl ether/hexane and filtered off under suction. 3.1 g (10 mmol, 33%) of the title compound are obtained as a colorless solid (mp.=93° C.)

$^1$H-NMR (CDCl$_3$; δ in ppm): 8.6 (s, 1H, isoxazolyl); 7.45 (m, 1H, phenyl); 7.2 (m, 3H, phenyl); 7.15 (d, 1H, J=18 Hz, =CH); 6.6 (d, 1H, J=18 Hz, =CH); 4.2 (s, 3H, O—CH$_3$); 3.95 (s, 3H, O—CH$_3$); 2.4 (s, 3H, CH$_3$)

EXAMPLE 11

Methyl β-keto-β-(5-methoxymethylpyrimidin-4-yl)-acetate O-methyloxime (Table 3, No. 145)

a) Methyl β-keto-α-methoximinovalerate 14 g (233 mmol) of acetic acid are added, with gentle cooling, to 30 g (185 mmol) of methyl β-keto-δ-methoxyvalerate (Synthesis (1979), 622; Zh. Org. Khim. 23 (1987), 288) and 14 g (200 mmol) of NaNO$_2$ in 60 ml of water. Stirring is carried out for 1 hour at room temperature, the reaction mixture is diluted with water and the aqueous phase is extracted three times with methylene chloride. The combined organic phases are dried over MgSO$_4$ and evaporated down. The residue is dissolved in 300 ml of acetone, and 30 g (220 mmol) of K$_2$CO$_3$ and 40 g (280 mmol) of methyl iodide are added. Stirring is carried out for 2 hours at room temperature, the insoluble solid is filtered off under suction and the reaction mixture is evaporated down.

The residue is taken up in methyl tert-butyl ether and the organic phase is washed with NH$_4$Cl solution, dried over MgSO$_4$ and evaporated down. 35 g (172 imol, 93%) of the title compound in the form of a yellow liquid are obtained as the residue.

$^1$H-NMR (CDCl$_3$; δ in ppm): 4.1 (s, 3H, O—CH$_3$); 3.9 (s, 3H, O—CH$_3$); 3.7 (t, 2H, J=7 Hz, CH$_2$); 3.35 (s, 3H, O—CH$_3$); 3.1 (t, 2H, J=7 Hz, CH$_2$)

b) Methyl δ-dimethylamino-β-keto-α-methoximino-γ-methoxymethylpent-4-enoate

A mixture of 10 g (50 mmol) of the ketone from Example 11a, 7 g (85 mmol) of sodium acetate and 7 g (69 mmol) of acetic anhydride in 20 ml of dimethylformamide dimethyl acetal is stirred for 2 hours at 70° C. The reaction mixture is diluted with methylene chloride and the organic phase is washed once with water. Thereafter, the organic phase is dried over MgSO$_4$ and evaporated down. The residue is purified by column chromatography using hexane/ethyl acetate mixtures and finally ethyl acetate. 11.4 g (44 mmol, 88%) of the title compound are obtained as a yellow oil.

$^1$H-NMR (CDCl$_3$; δ in ppmP: 7.7 (s, 1H, vinyl); 4.3 (s, 2H, CH$_2$); 4.0 (s, 3H, O—CH$_3$); 3.85 (s, 3H, O—CH$_3$); 3.3 (s, 3H, O—CH$_3$); 3.25 (s, 6H, N(CH$_3$)$_2$)

C) Methyl α-keto-α-(5-methoxymethylpyrimidin-4-yl)-acetate O-methyloxime (Table 3, No. 145)

2.6 g (10 mmol) of the enaminoketone from Example 11b, 2 g (14.4 mmol) of K$_2$CO$_3$ and 1.4 g (13.5 mmol) of formamidinium acetate in 20 ml of methanol are stirred for 3 hours at room temperature. The reaction mixture is then diluted with water and the aqueous phase is extracted three times with methyl tert-butyl ether. The combined organic phases are dried over MgSO$_4$ and evaporated down. The residue is purified by column chromatography using hexane/ethyl acetate mixtures. 0.65 g (2.7 mmol, 27%) of the title compound are obtained as a colorless solid (mp.=82° C.).

$^1$H-NMR (CDCl$_3$, δ in ppm): 9.15 (s, 1H, pyrimidinyl); 9.1 (s,, 1H, pyrimidinyl); 4.75 (s, 2H, O—CH$_2$); 4.15 (s, 3H, O—CH$_3$); 3.95 (s, 3H, O—CH$_3$); 3.55 (s, 3H, O—CH$_3$)

EXAMPLE 12

Methyl α-keto-α-(N-phenyl-5-methylpyrazol-4-yl)-acetate O-methyloxime (Table 3, No. 160)

a) Methyl γ-keto-α-methoximinovalerate 117.3 g (about 90% purity; 0.73 mol; prepared similarly to Organikum, 15th Edition 1976, page 584) of methyl α,γ-diketovalerate and 61.8 g (0.74 mol) of O-methylhydroxylamine hydrochloride in 1 l of methanol are stirred for 24 hours at room temperature. Thereafter, the reaction mixture is evaporated down, the residue is taken up in water and the solution is neutralized with Na$_2$CO$_3$ solution. The aqueous phase is then extracted three times with methylene chloride. The combined organic phases are dried over MgSO$_4$ and evaporated down. The residue is purified by column chromatography using hexane/ethyl acetate mixtures. 69.5 g (0.40 mol, 55%) of the title compound in the form of a pale yellow liquid is obtained as the residue.

$^1$H-NMR (CDCl$_3$; δ in ppm): 4.1 (s, 3H, O—CH$_3$); 3.9 (s, 3H, O—CH$_3$); 3.75 (s, 2H, CH$_2$); 2.25 (s, 3H, CH$_3$)

b) Methyl β-acetyl-γ-dimethylamino-β-methoximinobut-3-enoate

A mixture of 40 g (0.23 mol) of the ketone from Example 12a and 33 g (0.28 mol) of dimethylformamide dimethyl acetal is stirred for 5 hours at 70° C. Thereafter, the volatile components are stripped off, initially at 25 mbar and then under greatly reduced pressure. The residue is purified by column chromatography using hexane/ethyl acetate mixtures and ethyl acetate. 40 g (0.175 mol, 76%) of the title compound are obtained as a yellow solid (mp.=122° C.).

$^1$H-NMR (CDCl$_3$; δ in ppm): 7.55 (s, 1H, vinyl); 4.05 (s, 3H, O—CH$_3$); 3.9 (s, 3H, O—CH$_3$); 2.95 (s, broad, 6H, N(CH$_3$)$_2$); 2.1 (s, 3H, CH$_3$)

c) Methyl α-keto-α-(N-phenyl-5-methylpyrazol-4-yl)-acetate O-methyloxime (Table 3, No. 160)

7.1 g (66 mmol) of phenylhydrazine are added a little at a time at 0° C. to 10 g (44 mmol) of the enaminoketone from Example 12b in 20 ml of acetic acid. Stirring is carried out overnight at room temperature, after which the reaction mixture is diluted with water. The aqueous phase is extracted three times with methyl tert-butyl ether, and the combined organic phases are washed with $Na_2CO_3$ solution and water, dried over $MgSO_4$ and evaporated down. The residue is purified by column chromatography using hexane/ethyl acetate mixtures. 10.6 g (39 mmol, 88%) of the title compound in the form of a yellow oil are obtained as the residue.

$^1$H-NMR ($CDCl_3$; δ in ppm): 7.9 (s, 1H, pyrazolyl); 7.3–7.6 (m, 5H, phenyl); 4.15 (s, 3H, O—$CH_3$); 3.9 (s, 3H, O—$CH_3$); 2.2 (s, 3H, $CH_3$)

EXAMPLE 13

Methyl α-keto-γ-(N-phenyl-5-bromomethylpyrazol-4-yl)-acetate O-methyloxime (Table 3, No. 161 and 162)

A mixture of 9.4 g (34.4 mmol) of the methylpyrazole from Example 12c, 7.5 g (42 mmol) of N-bromosuccinimide and 0.1 g of azobisisobutyronitrile in 100 ml of carbon tetrachloride is exposed for 3 hours to a 300 W UV lamp, the reaction mixture warming up to 40–50° C. Thereafter, the insoluble solid is filtered off under suction and the filtrate is washed with water, dried over $MgSO_4$ and evaporated down. The residue is purified by column chromatography using hexane/ethyl acetate mixtures. 3 g (8.5 mmol, 25%) of the cis-oxime ether isomer and 4.8 g (13.6 mmol, 40%) of the trans-oxime ether isomer of the title compound are obtained.

$^1$H-NMR ($CDCl_3$, δ in ppm): cis-Isomer: 7.7 (s, 1H, pyrazolyl); 7.4–7.65 (m, 5H, phenyl); 4.65 (s, 2H, $CH_2Br$); 4.05 (s, 3H, O—$CH_3$); 3.95 (s, 3H, O—$CH_3$) trans-isomer: 7.9 (s, 1H, pyrazole); 7.4–7.6 (m, 5H, phenyl); 4.5 (s, 2, $CH_2Br$); 4.2 (s, 3H, O—$CH_3$); 3.95 (s, 3H, O—$CH_3$)

EXAMPLE 14

Methyl α-keto-α-(N-phenyl-5-(p-bromoacetophenoneiminoxymethyl)-pyrazol-4-yl)-acetate trans-O-methyloxime (Table 3, No. 143)

A mixture of 1.6 g (4.5 mmol) of the trans-methyloxime ether methyl bromide from Example 13, 1.6 g (4.5 mmol) of p-bromoacetophenone oxime and 0.6 g (4.5 mmol) of $K_2CO_3$ in 5 ml of dimethylformamide is stirred overnight at room temperature and then heated for about 5 hours at 50° C. Thereafter, the reaction mixture is diluted with water and extracted three times with methyl tert-butyl ether. The combined organic phases are extracted with water, dried over $MgSO_4$ and evaporated down. The residue is purified by column chromatography using hexane/ethyl acetate mixtures. 1.1 g (2.3 mmol, 50%) of the title compound are obtained as a yellow oil.

$^1$H-NMR ($CDCl_3$; δ in ppm): 8.0 (s, 1H, pyrazolyl); 7.3–7.6 (m, 9H, phenyl); 5.25 (s, 1H, $CH_2$—O; 4.1 (s, 3H, O—$CH_3$); 3.85 (s, 3H, O—$CH_3$); 2.1 (s, 3H, $CH_3$)

EXAMPLE 15

Methyl α-keto-α-(N-benzylimidazol-2-yl)-acetate-O-methyloxime (Table 3, No. 30)
a) Methyl α-keto-α-(N-benzylimidazol-2-yl)-acetate 9.3 g (76 mmol) of methoxyoxalyl chloride are added dropwise at 20–30° C. to a mixture of 10 g (60 mmol) of N-benzylimidazole (Chem. Pharm. Bull. 31 (4) (1983), 1213) and 9 g (90 mmol) of triethylamine in 100 ml of methylene chloride. Stirring is carried out for 3 hours at room temperature, after which the reaction mixture is extracted with $Na_2CO_3$ solution and water. The organic phase is dried over $MgSO_4$ and evaporated down. The residue is purified by column chromatography using 100:1 methylene chloride/methanol. Yield: 10.2 g (44 mmol, 74%).

$^1$H-NMR ($CDCl_3$, δ in ppm): 7.1–7.5 (m, 7H, phenyl, imidazolyl); 5.6 (s, 2H, N—$CH_2$); 3.95 (s, 3H; O—$CH_3$)
b) Methyl α-keto-α-(N-benzylimidazol-2-yl)-acetate O-methyloxime (Table 3, No. 30)

A mixture of 4.7 g (30 mmol) of the ketoester from Example 15a and 5 g (60 mmol) of methoxyamine hydrochloride in 60 ml of methanol is stirred overnight at room temperature. Thereafter, the reaction mixture is diluted with water and the aqueous phase is extracted three times with methylene chloride. The combined organic phases are extracted with water, dried over $MgSO_4$ and evaporated down. The residue is purified by column chromatagraphy with methylene chloride and 100:1 methylene chloride/methanol. 0.8 g (4.3 mmol, 14%) of the nonpolar isomer and 0.4 g (2.1 mmol, 7%) of the polar isomer (mp.=55–58° C.) of the title compound are obtained.

$^1$H-NMR ($CDCl_3$, δ in ppm): Nonpolar isomer: 7.1–7.5 (m, 6H, imidazolyl, phenyl); 6.95 (s, broad, 1H, imidazolyl); 5.5 (s, 2H, N—$CH_2$); 3.95 (s, 3H, O—$CH_3$); 3.93 (s, 3H, O—$CH_3$) Polar isomer: 7.05–7.4 (m, 6H, imidazolyl, phenyl); 6.95 (s, 1H, imidazolyl); 4.95 (s, 2H, N—$CH_2$); 4.05 (s, 3H, O—$CH_3$); 3.8 (s, 3H, O—$CH_3$)

EXAMPLE 16

Methyl 3-(2-chlorophenoxymethyl)-thien-2-ylglyoxylate trans-O-methyloxiune (Table 3, No. 15)
a) Ethyl 3-methylthien-2-ylglyoxylate 200 g (2 mol) of 3-methylthiophene and 368 g (3 mol) of methoxyoxalyl chloride are initially taken at 5° C. 400 g (3 mol) of $AlCl_3$ in 600 ml of nitromethane are added dropwise to this mixture and stirring is carried out for 1 hour at 10° C. and for 1 hour at room temperature. The mixture is poured onto 2 l of ice water and is extracted with ether. The organic phase is washed with saturated sodium carbonate solution, dried and evaporated down. The residue is distilled under reduced pressure. 213.7 g (58%) of the compound are obtained as yellow crystals (bp.: 105–110° C./0.5 mbar).
b) Methyl 3-methylthien-2-ylglyxoylate O-methyloxime (Table 3, No. 163)

A solution of 56.4 g (0.306 mol) of methyl 3-methylthien-2-ylglyoxylate and 25.5 g (0.306 mol) of O-methylhydroxylamine hydrochloride in 500 ml of methanol is refluxed for 15 hours. The mixture is evaporated down, the residue is taken up in ethyl acetate, the solution is washed with water and dried and the solvent is removed under reduced pressure. 51.7 g (79%) of the abovementioned compound are obtained as a 60:40 isomer mixtures $^1$H-NMR ($CDCl_3$; δ in ppm): Isomer A (nonpolar): 7.4 (d, 1H, J=4 Hz thienyl); 6.9 (d, 1H, J=4 Hz, thienyl); 4.1 (s, 3H, O—$CH_3$); 3.9 (s, 3H, O—$CH_3$); 2.15 (s, 1H, $CH_3$) Isomer B (polar): 7.25 (d, 1H, J=4 Hz, thienyl); 6.8 (d, 1H, J=4 Hz, thienyl); 4.0 (s, 3H, O—$CH_3$); 3.9 (s, 3H, O—$CH_3$); 2.3 (s, 1H, $CH_3$)
C) Methyl 3-bromomethylthien-2-ylglyoxylate O-methyloxime (Table 3, No. 164)

A solution of 46 g (0.216 mol) of methyl 3-methylthien-2-ylglyxoylate O-methyloxime and 42.1 g (0.237 mol) of N-bromosuccinimide in 400 ml of carbon tetrachloride is exposed for 3 hours to a UV lamp and is then filtered and evaporated down. 63.7 g of a black oil which contains the abovementioned compound in an amount of 60% are obtained.

¹H-NMR (CDCl₃; δ in ppm): 7.1–7.6 (thienyl protons): Isomer A: 4.3 (s, 2H, CH₂—Br); 4.15 (s, 3H, O—CH₃); 3.9 (s, 3H, O—CH₃) Isomer B: 4.65 (s, 2H, CH₂—Br); 4.05 (s, 3H, O—CH₃); 3.95 (s, 3H, O—CH₃)

d) Methyl 3-(2'-chlorophenoxymethyl)-thien-2-yl-glyoxylate trans-O-methyloxime (Table 3, No. 15)

5.14 g (0.04 mol) of 3-chlorophenyl, 6 g of potassium carbonate and 500 mg of potassium iodide are added to a solution of 11.7 g of the compound described under Example 16c, in 100 ml of acetone. The mixture is refluced for 24 hours, filtered and evaporated down. The residue is taken up in methylene chloride and the solution is washed with water, dried and evaporated down. The residue is chromatographed over silica gel using 1:5 ethyl acetate/hexane. 5.5 g of the abovementioned compound are obtained in the form of its trans-isomer.

¹H-NMR (CDCl₃; δ in ppm): 6.7–7.6 (m, 6H, aromat. protons); 4.95 (s, 3H, O—CH₂); 4.1 (s, 3H, O—CH₃); 3.8 (s, 3H, O—CH₃)

EXAMPLE 17

Methyl 3-(2'-chlorothiophenoxymethyl)-thien-2-yl-glyoxylate O-methyloxime (Table 3, No. 22 and 23)

a) Methyl 3-bromomethylthien-2-ylglyoxylate

A solution of 135.7 g (0.73 mol) of methyl 3-methylthien-2-ylglyoxylate, 131.2 g (0.73 mol) of N-bromosuccinimide and 1.35 g of azobisisobutyronitrile in 1000 ml of carbon tetrachloride is refluxed for 3 hours. Thereafter, the mixture is filtered and the filtrate is evaporated down. The residue is taken up in diethyl ether and the solution is washed with water, dried and evaporated down. 166.4 g of crude product are obtained, which is recrystallized from methanol. 100 g of the abovementioned compound are obtained as a yellow solid.

¹H-NMR (CDCl₃; δ in ppm); 7.75 (d, 1H, J=4 Hz, thienyl); 7.3 (d, 1H, J=4 Hz, thienyl); 4.95 (s, 2H, CH₂—Br); 4.0 (s, 3H, O—CH₃)

b) Methyl 3-(2-chlorothiophenoxymethyl)-thien-2-ylglyoxylate 2.62 g (19 mmol) of potassium carbonate and 2.74 g (19 mmol) of 2-chlorothiophenol are added to a solution of 5 g (19 nmol) of methyl 3-bromomethylthien-2-ylglyoxylate in 50 ml of acetone, the mixture is stirred for 72 hours at room temperature and filtered and the filtrate is evaporated down. The residue is taken up in methylene chloride, and the solution is washed with Na₂CO₃ solution, dried and evaporated down. The crude product is recrystallized from methanol. 4.24 g (68%) of the abovementioned compound are obtained.

¹H-NMR (CDCl₃; δ in ppm): 7.1–7.7 (m, 6H, aromatic); 4.6 (s, 3H, S—CH₂); 3.95 (s, 3H, OCH₃)

c) Methyl 3-(2-chlorothlophenoxymethyl)-thien-2-ylglyoxylate O-methyloxime (Table 3, No. 22 and 23)

4.24 g of the compound described under Example 17b are heated with 1.07 g of O-methylhydroxylamine chloride in 100 ml of methanol for 3 hours at 50° C. The mixture is evaporated down, the residue is taken up in ethyl acetate and the solution is washed with water, dried and evaporated down. The crude product is chromatographed over silica gel using 10:1 hexane/ethyl acetate. 810 mg (cis-isomer) and 1.87 g (trans-isomer) of the abovementioned compound are obtained in succession.

¹H-NMR (CDCl₃; δ in ppm): cis-Isomer: 7–7.4 (m, 6H, aromatic); 4.3 (s, 2H, S—CH₂); 4.0 (s, 3H, O—CH₃); 3.9 (s, 3H, O—CH₃) trans-Isomer: 7.1–7.5 (m, 6H, aromatic); 4.12 (s, 3H, O—CH₃); 4.0 (s, 3H, S—CH₂); 3.91 (s, 3H, O—CH₃)

EXAMPLE 18

Methyl pyrrol-2-ylglyoxylate O-methyloxime (Table 3, No. 165)

97.5 g (1.2 eq) of methoxyamine hydrochloride are added to a solution of 148.8 g (0.97 mol) of methyl pyrrol-2-ylglyoxylate (prepared by a method similar to that described by B. Lindstrbm et al., Acta Chem. Scand. 27 (1973), 7) in 1 l of methanol, and the solution is refluxed for 2.5 hours. After evaporation in a rotary evaporator, the residue is taken up in ethyl acetate and the solution is washed with water, dried and evaporated down. 81 g (46%) of the pyrrole remained in the form of an oil.

¹H-NMR (CDCl₃; δ in ppm): 10.35 (s, broad, 1H, N—H); 7.15 (m, 1H, pyrrolyl); 6.95 (m, 1H, pyrrolyl); 6.3 (m, 1H, pyrrolyl); 4.15 (s, 3H, O—CH₃); 3.9 (s, 3H, O—CH₃)

EXAMPLE 19

Methyl N-(o-methylbenzyl)-pyrrol-2-ylglyoxylate O-methyloxime (Table 3, No. 31)

4 g (35.7 mmol) of potassium tert-butylate are added to a solution of 730 mg (2.7 mmol) of 18-crown-6 in 50 ml of ether, after which a solution of 5 g (27.5 mmol) of the pyrrole from Example 18 in 50 ml of ether are added dropwise and stirring is carried out for 30 minutes at room temperature. Thereafter, a solution of 6.6 g (37.5 mmol) of o-methylbenzyl bromide in 25 ml of ether is addled and stirring is carried out overnight at room temperature. The mixture is poured onto water and extracted with ether, and the organic phase is dried and evaporated down. Chromatography over silica gel using hexane/ethyl acetate gives 4.1 g (52%) of the product as a yellow oil.

IR (ν in cm⁻¹): 1733, 1461, 1438, 1319, 1286, 1221, 1072, 1035, 776, 742

EXAMPLE 20

Methyl N-benzylpyrrol-2-ylglyoxylate O-methyloxime (Table 3, No. 30)

a) Methyl N-benzylpyrrol-2-ylglyoxylate

A suspension of 10 g (65 mmol) of methyl pyrrol-2-ylglyoxylate in 100 ml of ether is added to a solution of 1.7 g (6.5 mol) of 18-crown-6 with 7.3 g (65 mmol) of potassium tert-butylate in 100 ml of ether, stirring is carried out for 30 minutes and 11.1 g (65 mmol) of benzyl bromide in 50 ml of ether are then added dropwise. Stirring is carried out overnight at room temperature, the mixture is poured onto water and extracted with ether and the organic phase is dried and evaporated down. Chromatography over silica gel with hexane/ethyl acetate gives 6.7 g (42%) of the title compound as a reddish brown oi.

¹H-NMR (CDCl₃; δ in ppm): 7–7.4 (m, 7H, phenyl, pyrrolyl), 6.25 (m, 1H, pyrrolyl); 5.6 (s, 2H, N—CH₂); 3.9 (s, 3H, O—CH₃)

b) Methyl N-benzylpyrrol-2-ylglyoxylate O-methyloxime (Table 3, No. 30)

6.6 g (80 mmol) of methoxyamine hydrochloride are added to a solution of 3 g (12.3 mmol) of the ketoester from Example 20a in 100 ml of methanol and refluxing is carried out for 12 hours. The residue is evaporated in a rotary evaporator and then taken up in ethyl acetate, and the solution is washed with water, dried and evaporated down. Chromatography over silica gel with hexane/ethyl acetate gives 2 g (60%) of isomer A and 0.6 g (18%) of isomer B.

¹H-NMR (CDCl₃; δ in ppm): Isomer A (nonpolar): 7–7.3 (m, 5H, phenyl); 6.75 (m, 1H, pyrrolyl); 6.4 (m, 1H, pyrrolyl); 6.25 (m, 1H, pyrrolyl); 4.95 (s, 2H, N—CH₂); 4.0 (s, 3H, O—CH₃); 3.75 (s, 3H, O—CH₃)

EXAMPLE 21

Methyl α-keto-α-(5-phenylisoxazol-3-yl)-acetate O-methyloxime (Table 3, No. 47)

a) Methyl β-hydroximino-α-methoximinopropionate 25.9 g (220 mol) of N-methylmorpholine N-oxide are added at 25–35° C. to a solution of 10 g (48 mmol) of methyl β-bromopyruvate O-methyloxime in 40 ml of dimethyl sulfoxide. After stirring has been carried out for 30 minutes at room temperature, 6.95 g (100 mmol) of hydroxylamine hydrochloride are added and stirring is continued for a further 5 hours at room temperature. Thereafter, the mixture is poured onto saturated NaCl solution and is extracted four times with ether. The organic phase is dried and evaporated down. 4 g (25 mmol, 52%) of the title compound remain.

¹H-NMR (CDCl₃; δ in ppm): 10.15 (s, 1H, N—OH); 8.25 (s, 1H, N=CH); 4.15 (s, 3H, O—CH₃); 3.9 (s, 3H, O—CH₃)

b) Methyl α-keto-α-(5-phenylisoxazol-3-yl)-acetate O-methyloxime (Table 3, No. 47)

50 ml of hypochlorite solution are added dropwise to a solution of 2 g (12.5 mmol) of the aldoxime from Example 21a and 2.55 g (25 mmol) of phenylacetylene 2 in 50 ml of methylene chloride while cooling. After 30 minutes at room temperature, the organic phase is separated off and the aqueous phase is extracted with methylene chloride. The organic phase is dried and evaporated down. Chromatography over silica gel with hexane/ethyl acetate gives 1.1 g (35%) of isoxazole 2 as a yellow oil.

¹H-NMR (CDCl₃; δ in ppm): 7.4–7.9 (m, 5H, phenyl); 6.9 (s, 1H, isoxazolyl); 4.2 (s, 3H, O—CH₃); 3.95 (s, 3H, O—CH₃)

The compounds shown in the Tables below can be prepared in a similar manner. In the Tables below, the individual indices I, II, III, etc. or a, b, etc. are to be understood as follows.

The heteroaromatic ring is indicated by Roman numerals such as I, II, etc. Lower case letters, such as a, b, etc., indicate the side chain. $X_m$ are the substituents on an aromatic structure. A and B are the intermediate chain or the terminal group of the side chain.

For example, selected compounds from the Tables have the following structural formulae.

In Table 1, compound No. 1/I/a has the following formula:

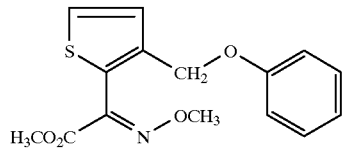

Table I, No. 1/I/a

In Table 1, compound No. 9/II/b has the following formula:

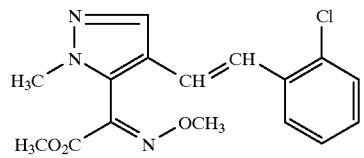

Table 1, No. 9/II/b

In Table 1, compound No. 68/III/c has the following formula:

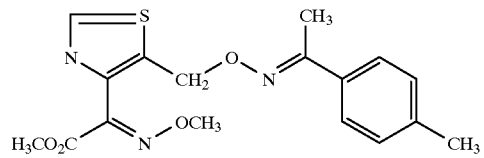

Table 1, No. 68/III/c

In Table 2, compound No. 127/I/a has the following formula:

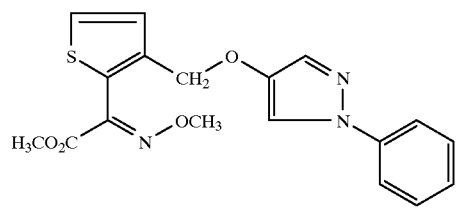

Table 2, No. 127/I/a

In Table 2, compound No. 175/II/b has the following formula:

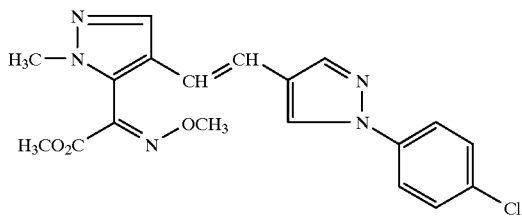

Table 2, No. 175/II/b

In Table 2, compound No. 37/III/c has the following formula:

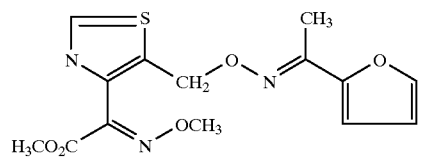

Table 2, No. 37/III/c

TABLE 1

I:

[Structure I: methyl 2-(3-(A-phenyl-X_m)thiophen-2-yl)-2-(methoxyimino)acetate]

II:

[Structure II: methyl 2-(4-(A-phenyl-X_m)-1-methyl-1H-pyrazol-5-yl)-2-(methoxyimino)acetate]

III:

[Structure III: methyl 2-(5-(A-phenyl-X_m)thiazol-4-yl)-2-(methoxyimino)acetate]

a) A = —CH$_2$—O—   b) A = —CH=CH— c) A = —CH$_2$—O—N=C(CH$_3$)—

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-tetramethylbutyl) |

TABLE 1-continued

| | |
|---|---|
| 117 | 4-(2,4,4-trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9$)2, 4-$CH_3$ |
| 121 | 2-$CH_3$, 4-t-$C_4H_9$ |
| 122 | 2-$CH_3$, 4-t-$C_4H_9$ |
| 123 | 2-CH3, 4-i-C3H7 |
| 124 | 2-$CH_3$, 5-i-$C_3H_7$ |
| 125 | 3-CH3, 4-i-C3H7 |
| 126 | 2-i-$C_3H_7$, 5-$CH_3$ |
| 127 | 2,4-(t-$C_4H_9$)2, 6-i-$C_3H_7$ |
| 128 | 2-allyl |
| 129 | 3-allyl |
| 130 | 4-allyl |
| 131 | 1-allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11}$)2, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$-$C_6H_5$ |
| 142 | 2-$C_6H_5$ |
| 143 | 3-$C_6H_5$ |
| 144 | 4-$C_6H_5$ |
| 145 | 4-(1-i-$C_3H_7$—$C_6H_4$) |
| 146 | 4-$C_6H_5$, 2,6-($CH_3$)$_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$CCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—($CH_2$)$_3C_6H_5$ |
| 181 | 3-O—($CH_2$)$_3C_6H_5$ |
| 182 | 4-O—($CH_2$)$_3C_6H_5$ |
| 183 | 2,4-($OCH_3$)$_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-($CH_3$)$_2$ |
| 228 | 2-Br, 4,5-($CH_3$)$_2$ |
| 229 | 2-Cl, 3,5-($CH_3$)$_2$ |
| 230 | 2-Br, 3,5-($CH_3$)$_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-($CH_3$)$_2$, 4-F |
| 238 | 2,6-($CH_3$)$_2$, 4-Cl |
| 239 | 2,6-($CH_3$)$_2$, 4-Br |
| 240 | 3,5-($CH_3$)$_2$, 4-F |
| 241 | 3,5-($CH_3$)$_2$, 4-Cl |
| 242 | 3,5-($CH_3$)$_2$, 4-Br |
| 243 | 2,3,6-($CH_3$)$_3$, 4-F |
| 244 | 2,3,6-($CH_3$)$_3$, 4-Cl |
| 245 | 2,3,6-($CH_3$)$_3$, 4-Br |
| 246 | 2,4-($CH_3$)$_2$, 6-F |
| 247 | 2,4-($CH_3$)$_2$, 6-Cl |
| 248 | 2,4-($CH_3$)$_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-$Cl_2$, 5-$NO_2$ |
| 254 | 2,4-$Cl_2$, 6-$NO_2$ |
| 255 | 2,6-$Cl_2$, 4-$NO_2$ |
| 256 | 2,6-$Br_2$, 4-$NO_2$ |
| 257 | 2,6-$I_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2$($C_2H_5$) |
| 263 | 3-$CO_2$($C_2H_5$) |
| 264 | 4-$CO_2$($C_2H_5$) |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |
| 274 | 2-$CH_2$—$OCH_3$ |

TABLE 1-continued

| | |
|---|---|
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,3-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CHO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOC$_2$H$_5$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-allyl)-CH$_3$ |
| 333 | 3-C(=NO-allyl)-CH$_3$ |
| 334 | 4-C(=NO-allyl)-CH$_3$ |
| 335 | 2-C(=NO-trans-chloroallyl)-CH$_3$ |
| 336 | 3-C(=NO-trans-chloroallyl)-CH$_3$ |
| 337 | 4-C(=NC-trans-chloroallyl)-CH$_3$ |
| 338 | 2-C(=NO-propargyl)-CH$_3$ |
| 339 | 3-C(=NC-propargyl)-CH$_3$ |
| 340 | 4-C(=NO-propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO-CH$_2$—C$_6$H$_5$)—CH$_3$ |
| 345 | 3-C(=NO-CH$_2$—C$_6$H$_5$)—CH$_3$ |
| 346 | 4-C(=NO-CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-allyl |
| 352 | 2-CH$_3$-4-CH=NO-(trans-chloroallyl) |
| 353 | 2-CH$_3$-4-CH=NO-propargyl |
| 354 | 2-CH$_3$-4-CH=NO-n-C$_4$H$_9$ |
| 355 | 2-CH$_3$-4-CH=NO-CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-allyl) |
| 361 | 2-CH$_3$-4-(CH$_3$—C=NO-trans-chloroallyl) |
| 362 | 2-CH$_3$-4-(CH$_3$—C=NO-propargyl) |
| 363 | 2-CH$_3$-4-(CH$_3$—C=NO-n-C$_4$H$_5$) |
| 364 | 2-CH$_3$-4-(CH$_3$—C=NO-CH$_2$-C$_6$H$_5$) |
| 365 | 2-CH$_3$-4-(C$_2$H$_5$—C=NO-CH$_3$) |
| 366 | 2-CH$_3$-4-(C$_2$H$_5$—C=NO-C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-allyl) |
| 370 | 2-CH$_3$-4-(C$_2$H$_5$—C=NO-trans-chloroallyl) |
| 371 | 2-CH$_3$-4-(C$_2$H$_5$—C=NO-propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)2-4-(CH$_3$-C=NOCH$_3$) |
| 375 | 2,5-(CH$_3$)2-4-(CH$_3$-C=NOC$_2$H$_5$) |
| 376 | 2,5-(CH$_3$)2-4-(CH$_3$-C=NO-n-C$_3$H$_7$) |
| 377 | 2,5-(CH$_3$)2-4-(CH$_3$-C=NO-i-C$_3$H$_7$) |
| 378 | 2,5-(CH$_3$)2-4-(CH$_3$-C=NO-allyl) |
| 379 | 2,5-(CH$_3$)2-4-(CH$_3$-C=NO-trans-chloroallyl) |
| 380 | 2,5-(CH$_3$)2-4-(CH$_3$-C=NO-proparyl) |
| 381 | 2,5-(CH$_3$)2-4-(CH$_3$-C=NO-n-C$_4$H$_9$) |
| 382 | 2,5-(CH$_3$)2-4-(CH$_3$-C=NO-CH$_2$-C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 404 | 2-(2'-CH$_3$—C$_6$H$_4$) |
| 405 | 2-(3'-CH$_3$—C$_6$H$_4$) |
| 406 | 2-(4'-CH$_3$—C$_6$H$_4$) |
| 407 | 3-(2'-CH$_3$—C$_6$H$_4$) |
| 408 | 3-(3'-CH$_3$—C$_6$H$_4$) |
| 409 | 3-(4'-CH$_3$—C$_6$H$_4$) |
| 410 | 4-(2'-CH$_3$—C$_6$H$_4$) |
| 411 | 4-(3'-CH$_3$—C$_6$H$_4$) |
| 412 | 4-(4'-CH$_3$—C$_6$H$_4$) |
| 413 | 2-(2'-CH$_3$—CO—C$_6$H$_4$) |
| 414 | 2-(3'-CH$_3$—CO—C$_6$H$_4$) |
| 415 | 2-(4'-CH$_3$—CO—C$_6$H$_4$) |
| 416 | 3-(2'-CH$_3$—CO—C$_6$H$_4$) |
| 417 | 3-(3'-CH$_3$—CO—C$_6$H$_4$) |
| 418 | 3-(4'-CH$_3$—CO—C$_6$H$_4$) |
| 419 | 4-(2'-CH$_3$—CO—C$_6$H$_4$) |
| 420 | 4-(3'-CH$_3$—CO—C$_6$H$_4$) |
| 421 | 4-(4'-CH$_3$—CO—C$_6$H$_4$) |
| 422 | 2-(2'-(CH$_3$—C(=NOallyl))-C$_6$H$_4$) |
| 423 | 2-(3'-(CH$_3$—C(=NOallyl))-C$_6$H$_4$) |
| 424 | 2-(4'-(CH$_3$—C(=NOallyl))-C$_6$H$_4$) |
| 425 | 3-(2'-(CH$_3$—C(=NOallyl))-C$_6$H$_4$) |
| 426 | 3-(3'-(CH$_3$—C(=NOallyl))-C$_6$H$_4$) |
| 427 | 3-(4'-(CH$_3$—C(=NOallyl))-C$_6$H$_4$) |
| 428 | 4-(2'-(CH$_3$—C(=NOallyl))-C$_6$H$_4$) |
| 429 | 4-(3'-(CH$_3$—C(=NCallyl))-C$_6$H$_4$) |
| 430 | 4-(4'-(CH$_3$—C(=NOallyl))-C$_6$H$_4$) |
| 431 | 2-(2'-CH$_3$O$_2$C—C$_6$H$_4$) |
| 432 | 2-(3'-CH$_3$O$_2$C—C$_6$H$_4$) |

TABLE 1-continued

| | |
|---|---|
| 433 | 2-(4'-CH$_3$O$_2$C—C$_6$H$_4$) |
| 434 | 3-(2'-CH$_3$O$_2$C—C$_6$H$_4$) |
| 435 | 3-(3'-CH$_3$O$_2$C—C$_6$H$_4$) |
| 436 | 3-(4'-CH$_3$O$_2$C—C$_6$H$_4$) |
| 437 | 4-(2'-CH$_3$O$_2$C—C$_6$H$_4$) |
| 438 | 4-(3'-CH$_3$O$_2$C—C$_6$H$_4$) |
| 439 | 4-(4'-CH$_3$O$_2$C—C$_6$H$_4$) |
| 440 | 2-(2'-CH$_3$O—C$_6$H$_4$) |
| 441 | 2-(3'-CH$_3$O—C$_6$H$_4$) |
| 442 | 2-(4'-CH$_3$O—C$_6$H$_4$) |
| 443 | 3-(2'-CH$_3$O—C$_6$H$_4$) |
| 444 | 3-(3'-CH$_3$O—C$_6$H$_4$) |
| 445 | 3-(4'-CH$_3$O—C$_6$H$_4$) |
| 446 | 4-(2'-CH$_3$O—C$_6$H$_4$) |
| 447 | 4-(3'-CH$_3$O—C$_6$H$_4$) |
| 448 | 4-(4'-CH$_3$O—C$_6$H$_4$) |
| 449 | 2-(2'-O$_2$N—C$_6$H$_4$) |
| 450 | 2-(3'-O$_2$N—C$_6$H$_4$) |
| 451 | 2-(4'-O$_2$N—C$_6$H$_4$) |
| 452 | 3-(2'-O$_2$N—C$_6$H$_4$) |
| 453 | 3-(3'-O$_2$N—C$_6$H$_4$) |
| 454 | 3-(4'-O$_2$N—C$_6$H$_4$) |
| 455 | 4-(2'-O$_2$N—C$_6$H$_4$) |
| 456 | 4-(3'-O$_2$N—C$_6$H$_4$) |
| 457 | 4-(4'-O$_2$N—C$_6$H$_4$) |
| 458 | 2-(2'-NC—C$_6$H$_4$) |
| 459 | 2-(3'-NC—C$_6$H$_4$) |
| 460 | 2-(4'-NC—C$_6$H$_4$) |
| 461 | 3-(2'-NC—C$_6$H$_4$) |
| 462 | 3-(3'-NC—C$_6$H$_4$) |
| 463 | 3-(4'-NC—C$_6$H$_4$) |
| 464 | 4-(2'-NC—C$_6$H$_4$) |
| 465 | 4-(3'-NC—C$_6$H$_4$) |
| 466 | 4-(4'-NC—C$_6$H$_4$) |
| 467 | 2-(2'-CF$_3$—C$_6$H$_4$) |
| 468 | 2-(3'-CF$_3$—C$_6$H$_4$) |
| 469 | 2-(4'-CF$_3$—C$_6$H$_4$) |
| 470 | 3-(2'-CF$_3$—C$_6$H$_4$) |
| 471 | 3-(3'-CF$_3$—C$_6$H$_4$) |
| 472 | 3-(4'-CF$_3$—C$_6$H$_4$) |
| 473 | 4-(2'-CF$_3$—C$_6$H$_4$) |
| 474 | 4-(3'-CF$_3$—C$_6$H$_4$) |
| 475 | 4-(4'-CF$_3$—C$_6$H$_4$) |
| 476 | 2-O-C$_6$H$_5$ |
| 477 | 3-O-C$_6$H$_5$ |
| 478 | 4-O-C$_6$H$_5$ |
| 479 | 2-O-(2'-F—C$_6$H$_4$) |
| 480 | 2-O-(3'-F—C$_6$H$_4$) |
| 481 | 2-O-(4'-F—C$_6$H$_4$) |
| 482 | 3-O-(2'-F—C$_6$H$_4$) |
| 483 | 3-O-(3'-F—C$_6$H$_4$) |
| 484 | 3-O-(4'-F—C$_6$H$_4$) |
| 485 | 4-O-(2'-F—C$_6$H$_4$) |
| 486 | 4-O-(3'-F—C$_6$H$_4$) |
| 487 | 4-O-(4'-F—C$_6$H$_4$) |
| 488 | 2-O-(2'-Cl—C$_6$H$_4$) |
| 489 | 2-O-(3'-Cl—C$_6$H$_4$) |
| 490 | 2-O-(4'-Cl—C$_6$H$_4$) |
| 491 | 3-O-(2'-Cl—C$_6$H$_4$) |
| 492 | 3-O-(3'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 506 | 4-O-(4'-CH$_3$—C$_6$H$_4$) |
| 507 | 2-O-(2'-CH$_3$—CO—C$_6$H$_4$) |
| 508 | 2-O-(3'-CH$_3$—CO—C$_6$H$_4$) |
| 509 | 2-O-(4'-CH$_3$—CO—C$_6$H$_4$) |
| 510 | 3-O-(2'-CH$_3$—CO—C$_6$H$_4$) |
| 511 | 3-O-(3'-CH$_3$—CO—C$_6$H$_4$) |
| 512 | 3-O-(4'-CH$_3$—CO—C$_6$H$_4$) |
| 513 | 4-O-(2'-CH$_3$—CO—C$_6$H$_4$) |
| 514 | 4-O-(3'-CH$_3$—CO—C$_6$H$_4$) |
| 515 | 4-O-(4'-CH$_3$—CO—C$_6$H$_4$) |
| 516 | 2-O-(2'-(CH$_3$—C(=NOallyl))-C$_6$H$_4$) |
| 517 | 2-O-(3'-(CH$_3$—C(=NOallyl))-C$_6$H$_4$) |
| 518 | 2-O-(4'-(CH$_3$—C(=NOallyl))-C$_6$H$_4$) |
| 519 | 3-O-(2'-(CH$_3$—C(=NOallyl))-C$_6$H$_4$) |
| 520 | 3-O-(3'-(CH$_3$—C(=NOallyl))-C$_6$H$_4$) |
| 521 | 3-O-(4'-(CH$_3$—C(=NOallyl))-C$_6$H$_4$) |
| 522 | 4-O-(2'-(CH$_3$—C(=NOallyl))-C$_6$H$_4$) |
| 523 | 4-O-(3'-(CH$_3$—C(=NOallyl))-C$_6$H$_4$) |
| 524 | 4-O-(4'-(CH$_3$—C(=NOallyl))-C$_6$H$_4$) |
| 525 | 2-O-(2'-CH$_3$O$_2$C—C$_6$H$_4$) |
| 526 | 2-O-(3'-CH$_3$O$_2$C—C$_6$H$_4$) |
| 527 | 2-O-(4'-CH$_3$O$_2$C—C$_6$H$_4$) |
| 528 | 3-O-(2'-CH$_3$O$_2$C—C$_6$H$_4$) |
| 529 | 3-O-(3'-CH$_3$O$_2$C—C$_6$H$_4$) |
| 530 | 3-O-(4'-CH$_3$O$_2$C—C$_6$H$_4$) |
| 531 | 4-O-(2'-CH$_3$O$_2$C—C$_6$H$_4$) |
| 532 | 4-O-(3'-CH$_3$O$_2$C—C$_6$H$_4$) |
| 533 | 4-O-(4'-CH$_3$O$_2$C—C$_6$H$_4$) |
| 534 | 2-O-(2'-CH$_3$O—C$_6$H$_4$) |
| 535 | 2-O-(3'-CH$_3$O—C$_6$H$_4$) |
| 536 | 2-O-(4'-CH$_3$O—C$_6$H$_4$) |
| 537 | 3-O-(2'-CH$_3$O—C$_6$H$_4$) |
| 538 | 3-O-(3'-CH$_3$O—C$_6$H$_4$) |
| 539 | 3-O-(4'-CH$_3$O—C$_6$H$_4$) |
| 540 | 4-O-(2'-CH$_3$O—C$_6$H$_4$) |
| 541 | 4-O-(3'-CH$_3$O—C$_6$H$_4$) |
| 542 | 4-O-(4'-CH$_3$O—C$_6$H$_4$) |
| 543 | 2-O-(2'-O$_2$N—C$_6$H$_4$) |
| 544 | 2-O-(3'-O$_2$N—C$_6$H$_4$) |
| 545 | 2-O-(4'-O$_2$N—C$_6$H$_4$) |
| 546 | 3-O-(2'-O$_2$N—C$_6$H$_4$) |
| 547 | 3-O-(3'-O$_2$N—C$_6$H$_4$) |
| 548 | 3-O-(4'-O$_2$N—C$_6$H$_4$) |
| 549 | 4-O-(2'-O$_2$N—C$_6$H$_4$) |
| 550 | 4-O-(3'-O$_2$N—C$_6$H$_4$) |
| 551 | 4-O-(4'-O$_2$N—C$_6$H$_4$) |
| 552 | 2-O-(2'-NC—C$_6$H$_4$) |
| 553 | 2-O-(3'-NC—C$_6$H$_4$) |
| 554 | 2-O-(4'-NC—C$_6$H$_4$) |
| 555 | 3-O-(2'-NC—C$_6$H$_4$) |
| 556 | 3-O-(3'-NC—C$_6$H$_4$) |
| 557 | 3-O-(4'-NC—C$_6$H$_4$) |
| 558 | 4-O-(2'-NC—C$_6$H$_4$) |
| 559 | 4-O-(3'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-pyridinyl-2' |
| 570 | 2-pyridinyl-3' |
| 571 | 2-pyridinyl-4' |
| 572 | 3-pyridinyl-2' |
| 573 | 3-pyridinyl-3' |
| 574 | 3-pyridinyl-4' |
| 575 | 4-pyridinyl-2' |
| 576 | 4-pyridinyl-3' |
| 577 | 4-pyridinyl-4' |
| 578 | 2-pyrimidinyl-2' |
| 579 | 2-pyrimidinyl-5' |
| 580 | 2-pyrimidinyl-4' |
| 581 | 3-pyrimidinyl-2' |
| 582 | 3-pyrimidinyl-5' |
| 583 | 3-pyrimidinyl-4' |
| 584 | 4-pyrimidinyl-2' |
| 585 | 4-pyrimidinyl-5' |
| 586 | 4-pyrimidinyl-4' |
| 587 | 2-pyrazolyl-1' |
| 588 | 2-pyrazolyl-3' |
| 589 | 2-pyrazolyl-4' |
| 590 | 3-pyrazolyl-1' |
| 591 | 3-pyrazolyl-3' |

TABLE 1-continued

| No. | |
|---|---|
| 592 | 3-pyrazolyl-4' |
| 593 | 4-pyrazolyl-1' |
| 594 | 4-pyrazolyl-3' |
| 595 | 4-pyrazolyl-4' |
| 596 | 2-isoxazolyl-3' |
| 597 | 2-isoxazolyl-4' |
| 598 | 2-isoxazolyl-5' |
| 599 | 3-isoxazolyl-3' |
| 600 | 3-isoxazolyl-4' |
| 601 | 3-isoxazolyl-5' |
| 602 | 4-isoxazolyl-3' |
| 603 | 4-isoxazolyl 4' |
| 604 | 4-isoxazolyl-5' |
| 605 | 2-isothiazolyl-3' |
| 606 | 2-isothiazolyl-4' |
| 607 | 2-isothiazolyl-5' |
| 608 | 3-isothiazolyl-3' |
| 609 | 3-isothiazolyl-4' |
| 610 | 3-isothiazolyl-5' |
| 611 | 4-isothiazolyl-3' |
| 612 | 4-isothiazolyl-4' |
| 613 | 4-isothiazolyl-5' |
| 614 | 2-imidazolyl-1' |
| 615 | 2-imidazolyl-2' |
| 616 | 2-imidazolyl-4' |
| 617 | 3-imidazolyl-1' |
| 618 | 3-imidazolyl-2' |
| 619 | 3-imidazolyl-4' |
| 620 | 4-imidazolyl-1' |
| 621 | 4-imidazolyl-2' |
| 622 | 4-imidazolyl-4' |
| 623 | 2-oxazolyl-2' |
| 624 | 2-oxazolyl-4' |
| 625 | 2-oxazolyl-5' |
| 626 | 3-oxazolyl-2' |
| 627 | 3-oxazolyl-4' |
| 628 | 3-oxazolyl-5' |
| 629 | 4-oxazolyl-2' |
| 630 | 4-oxazolyl-4' |
| 631 | 4-oxazolyl-5' |
| 632 | 2-thiazolyl-2' |
| 633 | 2-thiazolyl-4' |
| 634 | 2-thiazolyl-5' |
| 635 | 3-thiazolyl-2' |
| 636 | 3-thiazolyl-4' |
| 637 | 3-thiazolyl-5' |
| 638 | 4-thiazolyl-2' |
| 639 | 4-thiazolyl-4' |
| 640 | 4-thiazolyl-5' |

TABLE 2

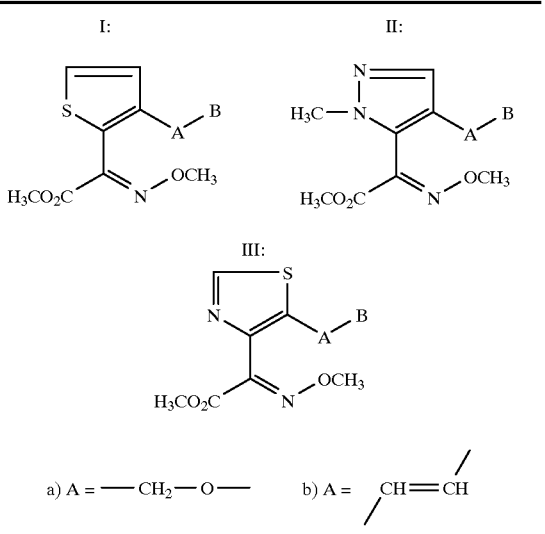

a) A = —CH₂—O—   b) A = —CH=CH—   c) A = —CH₂—O—N=C(CH₃)— 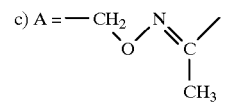

| No. | B |
|---|---|
| 1 | pyrrolyl-3 |
| 2 | N—CH₃-pyrrolyl-3 |
| 3 | N—C₆H₅-pyrrolyl-3 |
| 4 | N-(4'-CH₃—C₆H₄)-pyrrolyl-3 |
| 5 | N-(3'-CH₃—C₆H₄)-pyrrolyl-3 |
| 6 | N-(2'-CH₃—C₆H₄)-pyrrolyl-3 |
| 7 | N-(4'-CH₃O—C₆H₄)-pyrrolyl-3 |
| 8 | N-(3'-CH₃O—C₆H₄)-pyrrolyl-3 |
| 9 | N-(2'-CH₃O—C₆H₄)-pyrrolyl-3 |
| 10 | N-(4'-NO₂—C₆H₄)-pyrrolyl-3 |
| 11 | N-(3'-NO₂—C₆H₄)-pyrrolyl-3 |
| 12 | N-(2'-NO₂—C₆H₄)-pyrrolyl-3 |
| 13 | N-(4'-CN—C₆H₄)-pyrrolyl-3 |
| 14 | N-(3'-CN—C₆H₄)-pyrrolyl-3 |
| 15 | N-(2'-CN—C₆H₄)-pyrrolyl-3 |
| 16 | N-(4'-Cl—C₆H₄)-pyrrolyl-3 |
| 17 | N-(3'-Cl—C₆H₄)-pyrrolyl-3 |
| 18 | N-(2'-Cl—C₆H₄)-pyrrolyl-3 |
| 19 | pyrrolyl-2 |
| 20 | N—CH₃-pyrrolyl-2 |
| 21 | N—C₆H₅-pyrrolyl-2 |
| 22 | N-(4'-CH₃—C₆H₄)-pyrrolyl-2 |
| 23 | N-(3'-CH₃—C₆H₄)-pyrrolyl-2 |
| 24 | N-(2'-CH₃—C₆H₄)-pyrrolyl-2 |
| 25 | N-(4'-CH₃O—C₆H₄)-pyrrolyl-2 |
| 26 | N-(3'-CH₃O—C₆H₄)-pyrrolyl-2 |
| 27 | N-(2'-CH₃O—C₆H₄)-pyrrolyl-2 |
| 28 | N-(4'-NO₂—C₆H₄)-pyrrolyl-2 |
| 29 | N-(3'-NO₂—C₆H₄)-pyrrolyl-2 |
| 30 | N-(2'-NO₂—C₆H₄)-pyrrolyl-2 |
| 31 | N-(4'-CN—C₆H₄)-pyrrolyl-2 |
| 32 | N-(3'-CN—C₆H₄)-pyrrolyl-2 |
| 33 | N-(2'-CN—C₆H₄)-pyrrolyl-2 |
| 34 | N-(4'-Cl—C₆H₄)-pyrrolyl-2 |
| 35 | N-(3'-Cl—C₆H₄)-pyrrolyl-2 |
| 36 | N-(2'-Cl—C₆H₄)-pyrrolyl-2 |
| 37 | furyl-2 |
| 38 | 5-CH₃-furyl-2 |
| 39 | 5-C₆H₅-furyl-2 |
| 40 | 5-(4'-CH₃—C₆H₄)-furyl-2 |
| 41 | 5-(3'-CH₃—C₆H₄)-furyl-2 |
| 42 | 5-(2'-CH₃—C₆H₄)-furyl-2 |
| 43 | 5-(4'-CH₃O—C₆H₄)-furyl-2 |
| 44 | 5-(3'-CH₃O—C₆H₄)-furyl-2 |
| 45 | 5-(2'-CH₃O—C₆H₄)-furyl-2 |
| 46 | 5-(4'-NO₂—C₆H₄)-furyl-2 |
| 47 | 5-(3'-NO₂—C₆H₄)-furyl-2 |
| 48 | 5-(2'-NO₂—C₆H₄)-furyl-2 |
| 49 | 5-(4'-CN—C₆H₄)-furyl-2 |
| 50 | 5-(3'-CN—C₆H₄)-furyl-2 |
| 51 | 5-(2'-CN—C₆H₄)-furyl-2 |
| 52 | 5-(4'-Cl—C₆H₄)-furyl-2 |
| 53 | 5-(3'-Cl—C₆H₄)-furyl-2 |
| 54 | 5-(2'-Cl—C₆H₄)-furyl-2 |
| 55 | 4-CH₃-furyl-2 |
| 56 | 4-C₆H₅-furyl-2 |
| 57 | 4-(4'-CH₃—C₆H₄)-furyl-2 |
| 58 | 4-(3'-CH₃—C₆H₄)-furyl-2 |
| 59 | 4-(2'-CH₃—C₆H₄)-furyl-2 |
| 60 | 4-(4'-CH₃O—C₆H₄)-furyl-2 |
| 61 | 4-(3'-CH₃O—C₆H₄)-furyl-2 |
| 62 | 4-(2'-CH₃O—C₆H₄)-furyl-2 |
| 63 | 4-(4'-NO₂—C₆H₄)-furyl-2 |
| 64 | 4-(3'-NO₂—C₆H₄)-furyl-2 |
| 65 | 4-(2'-NO₂—C₆H₄)-furyl-2 |
| 66 | 4-(4'-CN—C₆H₄)-furyl-2 |
| 67 | 4-(3'-CN—C₆H₄)-furyl-2 |
| 68 | 4-(2'-CN—C₆H₄)-furyl-2 |
| 69 | 4-(4'-Cl—C₆H₄)-furyl-2 |
| 70 | 4-(3'-Cl—C₆H₄)-furyl-2 |
| 71 | 4-(2'-Cl—C₆H₄)-furyl-2 |
| 72 | thienyl-2 |
| 73 | 5-CH₃-thienyl-2 |

| # | |
|---|---|
| 74 | 5-C$_6$H$_5$-thienyl-2 |
| 75 | 5-(4'-CH$_3$—C$_6$H$_4$)-thienyl-2 |
| 76 | 5-(3'-CH$_3$—C$_6$H$_4$)-thienyl-2 |
| 77 | 5-(2'-CH$_3$—C$_6$H$_4$)-thienyl-2 |
| 78 | 5-(4'-CH$_3$O—C$_6$H$_4$)-thienyl-2 |
| 79 | 5-(3'-CH$_3$O—C$_6$H$_4$)-thienyl-2 |
| 80 | 5-(2'-CH$_3$O—C$_6$H$_4$)-thienyl-2 |
| 81 | 5-(4'-NO$_2$—C$_6$H$_4$)-thienyl-2 |
| 82 | 5-(3'-NO$_2$—C$_6$H$_4$)-thienyl-2 |
| 83 | 5-(2'-NO$_2$—C$_6$H$_4$)-thienyl-2 |
| 84 | 5-(4'-CN—C$_6$H$_4$)-thienyl-2 |
| 85 | 5-(3'-CN—C$_6$H$_4$)-thienyl-2 |
| 86 | 5-(2'-CN—C$_6$H$_4$)-thienyl-2 |
| 87 | 5-(4'-Cl—C$_6$H$_4$)-thienyl-2 |
| 88 | 5-(3'-Cl—C$_6$H$_4$)-thienyl-2 |
| 89 | 5-(2'-Cl—C$_6$H$_4$)-thienyl-2 |
| 90 | 4-CH$_3$-thienyl-2 |
| 91 | 4-C$_6$H$_5$-thienyl-2 |
| 92 | 4-(4'-CH$_3$—C$_6$H$_4$)-thienyl-2 |
| 93 | 4-(3'-CH$_3$—C$_6$H$_4$)-thienyl-2 |
| 94 | 4-(2'-CH$_3$—C$_6$H$_4$)-thienyl-2 |
| 95 | 4-(4'-CH$_3$O—C$_6$H$_4$)-thienyl-2 |
| 96 | 4-(3'-CH$_3$O—C$_6$H$_4$)-thienyl-2 |
| 97 | 4-(2'-CH$_3$O—C$_6$H$_4$)-thienyl-2 |
| 98 | 4-(4'-NO$_2$—C$_6$H$_4$)-thienyl-2 |
| 99 | 4-(3'-NO$_2$—C$_6$H$_4$)-thienyl-2 |
| 100 | 4-(2'-NO$_2$—C$_6$H$_4$)-thienyl-2 |
| 101 | 4-(4'-CN—C$_6$H$_4$)-thienyl-2 |
| 102 | 4-(3'-CN—C$_6$H$_4$)-thienyl-2 |
| 103 | 4-(2'-CN—C$_6$H$_4$)-thienyl-2 |
| 104 | 4-(4'-Cl—C$_6$H$_4$)-thienyl-2 |
| 105 | 4-(3'-Cl—C$_6$H$_4$)-thienyl-2 |
| 106 | 4-(2'-Cl—C$_6$H$_4$)-thienyl-2 |
| 107 | thienyl-3 |
| 108 | 5-CH$_3$-thienyl-3 |
| 109 | 5-C$_6$H$_5$-thienyl-3 |
| 110 | 5-(4'-CH$_3$—C$_6$H$_4$)-thienyl-3 |
| 111 | 5-(3'-CH$_3$—C$_6$H$_4$)-thienyl-3 |
| 112 | 5-(2'-CH$_3$—C$_6$H$_4$)-thienyl-3 |
| 113 | 5-(4'-CH$_3$O—C$_6$H$_4$)-thienyl-3 |
| 114 | 5-(3'-CH$_3$O—C$_6$H$_4$)-thienyl-3 |
| 115 | 5-(2'-CH$_3$O—C$_6$H$_4$)-thienyl-3 |
| 116 | 5-(4'-NO$_2$—C$_6$H$_4$)-thienyl-3 |
| 117 | 5-(3'-NO$_2$—C$_6$H$_4$)-thienyl-3 |
| 118 | 5-(2'-NO$_2$—C$_6$H$_4$)-thienyl-3 |
| 119 | 5-(4'-CN—C$_6$H$_4$)-thienyl-3 |
| 120 | 5-(3'-CN—C$_6$H$_4$)-thienyl-3 |
| 121 | 5-(2'-CN—C$_6$H$_4$)-thienyl-3 |
| 122 | 5-(4'-Cl—C$_6$H$_4$)-thienyl-3 |
| 123 | 5-(3'-Cl—C$_6$H$_4$)-thienyl-3 |
| 124 | 5-(2'-Cl—C$_6$H$_4$)-thienyl-3 |
| 125 | pyrazolyl-4 |
| 126 | N—CH$_3$-pyrazolyl-4 |
| 127 | N—C$_6$H$_5$-pyrazolyl-4 |
| 128 | N-(4'-CH$_3$—C$_6$H$_4$)-pyrazolyl-4 |
| 129 | N-(3'-CH$_3$—C$_6$H$_4$)-pyrazolyl-4 |
| 130 | N-(2'-CH$_3$—C$_6$H$_4$)-pyrazolyl-4 |
| 131 | N-(4'-CH$_3$O—C$_6$H$_4$)-pyrazolyl-4 |
| 132 | N-(3'-CH$_3$O—C$_6$H$_4$)-pyrazolyl-4 |
| 133 | N-(2'-CH$_3$O—C$_6$H$_4$)-pyrazolyl-4 |
| 134 | N-(4'-NO$_2$—C$_6$H$_4$)-pyrazolyl-4 |
| 135 | N-(3'-NO$_2$—C$_6$H$_4$)-pyrazolyl-4 |
| 136 | N-(2'-NO$_2$—C$_6$H$_4$)-pyrazolyl-4 |
| 137 | N-(4'-CN—C$_6$H$_4$)-pyrazolyl-4 |
| 138 | N-(3'-CN—C$_6$H$_4$)-pyrazolyl-4 |
| 139 | N-(2'-CN—C$_6$H$_4$)-pyrazolyl-4 |
| 140 | N-(4'-Cl—C$_6$H$_4$)-pyrazolyl-4 |
| 141 | N-(3'-Cl—C$_6$H$_4$)-pyrazolyl-4 |
| 142 | N-(2'-Cl—C$_6$H$_4$)-pyrazolyl-4 |
| 143 | 3-CH$_3$—N-methylpyrazolyl-4 |
| 144 | 3-C$_6$H$_5$—N-methylpyrazolyl-4 |
| 145 | 3-(4'-CH$_3$—C$_6$H$_4$)—N-methylpyrazolyl-4 |
| 146 | 3-(3'-CH$_3$—C$_6$H$_4$)—N-methylpyrazolyl-4 |
| 147 | 3-(2'-CH$_3$—C$_6$H$_4$)—N-methylpyrazolyl-4 |
| 148 | 3-4'-CH$_3$O—C$_6$H$_4$)—N-methylpyrazolyl-4 |
| 149 | 3-(3'-CH$_3$O—C$_6$H$_4$)—N-methylpyrazolyl-4 |
| 150 | 3-(2'-CH$_3$O—C$_6$H$_4$)—N-methylpyrazolyl-4 |
| 151 | 3-(4'-NO$_2$—C$_6$H$_4$)—N-methylpyrazolyl-4 |
| 152 | 3-(3'-NO$_2$—C$_6$H$_4$)—N-methylpyrazolyl-4 |
| 153 | 3-(2'-NO$_2$—C$_6$H$_4$)—N-methylpyrazolyl-4 |
| 154 | 3-(4'-CN—C$_6$H$_4$)—N-methylpyrazolyl-4 |
| 155 | 3-(3'-CN—C$_6$H$_4$)—N-methylpyrazolyl-4 |
| 156 | 3-(2'-CN—C$_6$H$_4$)—N-methylpyrazolyl-4 |
| 157 | 3-(4'-Cl—C$_6$H$_4$)—N-methylpyrazolyl-4 |
| 158 | 3-(3'-Cl—C$_6$H$_4$)—N-methylpyrazolyl-4 |
| 159 | 3-(2'-Cl—C$_6$H$_4$)—N-methylpyrazolyl-4 |
| 160 | isoxazolyl-5 |
| 161 | 3-CH$_3$-isoxazolyl-5 |
| 162 | 3-C$_6$H$_5$-isoxazolyl-5 |
| 163 | 3-(4'-CH$_3$—C$_6$H$_4$)-isoxazolyl-5 |
| 164 | 3-(3'-CH$_3$—C$_6$H$_4$)-isoxazolyl-5 |
| 165 | 3-(2'-CH$_3$—C$_6$H$_4$)-isoxazolyl-5 |
| 166 | 3-(4'-CH$_3$O—C$_6$H$_4$)-isoxazolyl-5 |
| 167 | 3-(3'-CH$_3$O—C$_6$H$_4$)-isoxazolyl-5 |
| 168 | 3-(2'-CH$_3$O—C$_6$H$_4$)-isoxazolyl-5 |
| 169 | 3-(4'-NO$_2$—C$_6$H$_4$)-isoxazolyl-5 |
| 170 | 3-(3'-NO$_2$—C$_6$H$_4$)-isoxazolyl-5 |
| 171 | 3-(2'-NO$_2$—C$_6$H$_4$)-isoxazolyl-5 |
| 172 | 3-(4'-CN—C$_6$H$_4$)-isoxazolyl-5 |
| 173 | 3-(3'-CN—C$_6$H$_4$)-isoxazolyl-5 |
| 174 | 3-(2'-CN—C$_6$H$_4$)-isoxazolyl-5 |
| 175 | 3-(4'-Cl—C$_6$H$_4$)-isoxazolyl-5 |
| 176 | 3-(3'-Cl—C$_6$H$_4$)-isoxazolyl-5 |
| 177 | 3-(2'-Cl—C$_6$H$_4$)-isoxazolyl-5 |
| 178 | 4-chloroisoxazolyl-5 |
| 179 | 3-CH$_3$-4-chloroisoxazolyl-5 |
| 180 | 3-C$_6$H$_5$-4-chloroisoxazolyl-5 |
| 181 | 3-(4'-CH$_3$—C$_6$H$_4$)-chloroisoxazolyl-5 |
| 182 | 3-(3'-CH$_3$—C$_6$H$_4$)-chloroisoxazolyl-5 |
| 183 | 3-(2'-CH$_3$—C$_6$H$_4$)-chloroisoxazolyl-5 |
| 184 | 3-(4'-CH$_3$O—C$_6$H$_4$)-chloroisoxazolyl-5 |
| 185 | 3-(3'-CH$_3$O—C$_6$H$_4$)-chloroisoxazolyl-5 |
| 186 | 3-(2'-CH$_3$O—C$_6$H$_4$)-chloroisoxazolyl-5 |
| 187 | 3-(4'-NO$_2$—C$_6$H$_4$)-chloroisoxazolyl-5 |
| 188 | 3-(3'-NO$_2$—C$_6$H$_4$)-chloroisoxazolyl-5 |
| 189 | 3-(2'-NO$_2$—C$_6$H$_4$)-chloroisoxazolyl-5 |
| 190 | 3-(4'-CN—C$_6$H$_4$)-chloroisoxazolyl-5 |
| 191 | 3-(3'-CN—C$_6$H$_4$)-chloroisoxazolyl-5 |
| 192 | 3-(2'-CN—C$_6$H$_4$)-chloroisoxazolyl-5 |
| 193 | 3-(4'-Cl—C$_6$H$_4$)-chloroisoxazolyl-5 |
| 194 | 3-(3'-Cl—C$_6$H$_4$)-chloroisoxazolyl-5 |
| 195 | 3-(2'-Cl—C$_6$H$_4$)-chloroisoxazolyl-5 |
| 196 | isoxazolyl-3 |
| 197 | 5-CH$_3$-isoxazolyl-3 |
| 198 | 5-C$_6$H$_5$-isoxazolyl-3 |
| 199 | 5-(4'-CH$_3$—C$_6$H$_4$)-isoxazolyl-3 |
| 200 | 5-(3'-CH$_3$—C$_6$H$_4$)-isoxazolyl-3 |
| 201 | 5-(2'-CH$_3$—C$_6$H$_4$)-isoxazolyl-3 |
| 202 | 5-(4'-CH$_3$O—C$_6$H$_4$)-isoxazolyl-3 |
| 203 | 5-(3'-CH$_3$O—C$_6$H$_4$)-isoxazolyl-3 |
| 204 | 5-(2'-CH$_3$O—C$_6$H$_4$)-isoxazolyl-3 |
| 205 | 5-(4'-NO$_2$—C$_6$H$_4$)-isoxazolyl-3 |
| 206 | 5-(3'-NO$_2$—C$_6$H$_4$)-isoxazolyl-3 |
| 207 | 5-(2'-NO$_2$—C$_6$H$_4$)-isoxazolyl-3 |
| 208 | 5-(4'-CN—C$_6$H$_4$)-isoxazolyl-3 |
| 209 | 5-(3'-CN—C$_6$H$_4$)-isoxazolyl-3 |
| 210 | 5-(2'-CN—C$_6$H$_4$)-isoxazolyl-3 |
| 211 | 5-(4'-Cl—C$_6$H$_4$)-isoxazolyl-3 |
| 212 | 5-(3'-Cl—C$_6$H$_4$)-isoxazolyl-3 |
| 213 | 5-(2'-Cl—C$_6$H$_4$)-isoxazolyl-3 |
| 214 | isothiazolyl-5 |
| 215 | 3-CH$_3$-isothiazolyl-5 |
| 216 | 3-C$_6$H$_5$-isothiazolyl-5 |
| 217 | 3-(4'-CH$_3$—C$_6$H$_4$)-isothiazolyl-5 |
| 218 | 3-(3'-CH$_3$—C$_6$H$_4$)-isothiazolyl-5 |
| 219 | 3-(2'-CH$_3$—C$_6$H$_4$)-isothiazolyl-5 |
| 220 | 3-(4'-CH$_3$O—C$_6$H$_4$)-isothiazolyl-5 |
| 221 | 3-(3'-CH$_3$O—C$_6$H$_4$)-isothiazolyl-5 |
| 222 | 3-(2'-CH$_3$O—C$_6$H$_4$)-isothiazolyl-5 |
| 223 | 3-(4'-NO$_2$—C$_6$H$_4$)-isothiazolyl-5 |
| 224 | 3-(3'-NO$_2$—C$_6$H$_4$)-isothiazolyl-5 |
| 225 | 3-(2'-NO$_2$—C$_6$H$_4$)-isothiazolyl-5 |
| 226 | 3-(4'-CN—C$_6$H$_4$)-isothiazolyl-5 |
| 227 | 3-(3'-CN—C$_6$H$_4$)-isothiazolyl-5 |
| 228 | 3-(2'-CN—C$_6$H$_4$)-isothiazolyl-5 |
| 229 | 3-(4'-Cl—C$_6$H$_4$)-isothiazolyl-5 |
| 230 | 3-(3'-Cl—C$_6$H$_4$)-isothiazolyl-5 |
| 231 | 3-(2'-Cl—C$_6$H$_4$)-isothiazolyl-5 |
| 232 | oxazolyl-4 |
| 233 | 2-CH$_3$-oxazolyl-4 |
| 234 | 2-C$_6$H$_5$-oxazolyl-4 |
| 235 | 2-(4'-CH$_3$—C$_6$H$_4$)-oxazolyl-4 |
| 236 | 2-(3'-CH$_3$—C$_6$H$_4$)-oxazolyl-4 |
| 237 | 2-(2'-CH$_3$—C$_6$H$_4$)-oxazolyl-4 |

| | | | | |
|---|---|---|---|---|
| 238 | 2-(4'-CH₃O—C₆H₄)-oxazolyl-4 | | 320 | 5-(3'-Cl—C₆H₄)-1,2,4-oxadiazolyl-3 |
| 239 | 2-(3'-CH₃O—C₆H₄)-oxazolyl-4 | | 321 | 5-(2'-Cl—C₆H₄)-1,2,4-oxadiazolyl-3 |
| 240 | 2-(2'-CH₃O—C₆H₄)-oxazolyl-4 | | 322 | 1,2,4-oxadiazolyl-5 |
| 241 | 2-(4'-NO₂—C₆H₄)-oxazolyl-4 | | 323 | 3-CH₃-1,2,4-oxadiazolyl-5 |
| 242 | 2-(3'-NO₂—C₆H₄)-oxazolyl-4 | | 324 | 3-C₆H₅-1,2,4-oxadiazolyl-5 |
| 243 | 2-(2'-NO₂—C₆H₄)-oxazolyl-4 | | 325 | 3-(4'-CH₃—C₆H₄)-1,2,4-oxadiazolyl-5 |
| 244 | 2-(4'-CN—C₆H₄)-oxazolyl-4 | | 326 | 3-(3'-CH₃—C₆H₄)-1,2,4-oxadiazolyl-5 |
| 245 | 2-(3'-CN—C₆H₄)-oxazolyl-4 | | 327 | 3-(2'-CH₃—C₆H₄)-1,2,4-oxadiazolyl-5 |
| 246 | 2-(2'-CN—C₆H₄)-oxazolyl-4 | | 328 | 3-(4'-CH₃O—C₆H₄)-1,2,4-oxadiazolyl-5 |
| 247 | 2-(4'-Cl—C₆H₄)-oxazolyl-4 | | 329 | 3-(3'-CH₃O—C₆H₄)-1,2,4-oxadiazolyl-5 |
| 248 | 2-(3'-Cl—C₆H₄)-oxazolyl-4 | | 330 | 3-(2'-CH₃O—C₆H₄)-1,2,4-oxadiazolyl-5 |
| 249 | 2-(2'-Cl—C₆H₄)-oxazolyl-4 | | 331 | 3-(4'-NO₂—C₆H₄)-1,2,4-oxadiazolyl-5 |
| 250 | thiazolyl-4 | | 332 | 3-(3'-NO₂—C₆H₄)-1,2,4-oxadiazolyl-5 |
| 251 | 2-CH₃-thiazolyl-4 | | 333 | 3-(2'-NO₂—C₆H₄)-1,2,4-oxadiazolyl-5 |
| 252 | 2-C₆H₅-thiazolyl | | 334 | 3-(4'-CN—C₆H₄)-1,2,4-oxadiazolyl-5 |
| 253 | 2-(4'-CH₃—C₆H₄)-thiazolyl-4 | | 335 | 3-(3'-CN—C₆H₄)-1,2,4-oxadiazolyl-5 |
| 254 | 2-(3'-CH₃—C₆H₄)-thiazolyl-4 | | 336 | 3-(2'-CN—C₆H₄)-1,2,4-oxadiazolyl-5 |
| 255 | 2-(2'-CH₃—C₆H₄)-thiazolyl-4 | | 337 | 3-(4'-Cl—C₆H₄)-1,2,4-oxadiazolyl-5 |
| 256 | 2-(4'-CH₃O—C₆H₄)-thiazolyl-4 | | 338 | 3-(3'-Cl—C₆H₄)-1,2,4-oxadiazolyl-5 |
| 257 | 2-(3'-CH₃O—C₆H₄)-thiazolyl-4 | | 339 | 3-(2'-Cl—C₆H₄)-1,2,4-oxadiazolyl-5 |
| 258 | 2-(2'-CH₃O—C₆H₄)-thiazolyl-4 | | 340 | 1,2,4-thiadiazolyl-3 |
| 259 | 2-(4'-NO₂—C₆H₄)-thiazolyl-4 | | 341 | 5-CH₃-1,2,4-thiadiazolyl-3 |
| 260 | 2-(3'-NO₂—C₆H₄)-thiazolyl-4 | | 342 | 5-C₆H₅-1,2,4-thiadiazolyl-3 |
| 261 | 2-(2'-NO₂—C₆H₄)-thiazolyl-4 | | 343 | 5-(4'-CH₃—C₆H₄)-1,2,4-thiadiazolyl-3 |
| 262 | 2-(4'-CN—C₆H₄)-thiazolyl-4 | | 344 | 5-(3'-CH₃—C₆H₄)-1,2,4-thiadiazolyl-3 |
| 263 | 2-(3'-CN—C₆H₄)-thiazolyl-4 | | 345 | 5-(2'-CH₃—C₆H₄)-1,2,4-thiadiazolyl-3 |
| 264 | 2-(2'-CN—C₆H₄)-thiazolyl-4 | | 346 | 5-(4'-CH₃O—C₆H₄)-1,2,4-thiadiazolyl-3 |
| 265 | 2-(4'-Cl—C₆H₄)-thiazolyl-4 | | 347 | 5-(3'-CH₃O—C₆H₄)-1,2,4-thiadiazolyl-3 |
| 266 | 2-(3'-Cl—C₆H₄)-thiazolyl-4 | | 348 | 5-(2'-CH₃O—C₆H₄)-1,2,4-thiadiazolyl-3 |
| 267 | 2-(2'-Cl—C₆H₄)-thiazolyl-4 | | 349 | 5-(4'-NO₂—C₆H₄)-1,2,4-thiadiazolyl-3 |
| 268 | N—CH₃-1,2,4-triazolyl-5 | | 350 | 5-(3'-NO₂—C₆H₄)-1,2,4-thiadiazolyl-3 |
| 269 | 3-CH₃—N—CH₃-1,2,4-triazolyl-5 | | 351 | 5-(2'-NO₂—C₆H₄)-1,2,4-thiadiazolyl-3 |
| 270 | 3-C₆H₅—N—CH₃-1,2,4-triazolyl-5 | | 352 | 5-(4'-CN—C₆H₄)-1,2,4-thiadiazolyl-3 |
| 271 | 3-(4'-CH₃—C₆H₄)—N—CH₃-1,2,4-triazolyl-5 | | 353 | 5-(3'-CN—C₆H₄)-1,2,4-thiadiazolyl-3 |
| 272 | 3-(3'-CH₃—C₆H₄)—N—CH₃-1,2,4-triazolyl-5 | | 354 | 5-(2'-CN—C₆H₄)-1,2,4-thiadiazolyl-3 |
| 273 | 3-(2'-CH₃—C₆H₄)—N—CH₃-1,2,4-triazolyl-5 | | 355 | 5-(4'-Cl—C₆H₄)-1,2,4-thiadiazolyl-3 |
| 274 | 3-(4'-CH₃O—C₆H₄)—N—CH₃-1,2,4-triazolyl-5 | | 356 | 5-(3'-Cl—C₆H₄)-1,2,4-thiadiazolyl-3 |
| 275 | 3-(3'-CH₃O—C₆H₄)—N—CH₃-1,2,4-triazolyl-5 | | 357 | 5-(2'-Cl—C₆H₄)-1,2,4-thiadiazolyl-3 |
| 276 | 3-(2'-CH₃O—C₆H₄)—N—CH₃-1,2,4-triazolyl-5 | | 358 | 1,3,4-thiadiazolyl-2 |
| 277 | 3-(4'-NO₂—C₆H₄)—N—CH₃-1,2,4-triazolyl-5 | | 359 | 5-CH₃-1,3,4-thiadiazolyl-2 |
| 278 | 3-(3'-NO₂—C₆H₄)—N—CH₃-1,2,4-triazolyl-5 | | 360 | 5-C₆H₅-1,3,4-thiadiazolyl-2 |
| 279 | 3-(2'-NO₂—C₆H₄)—N—CH₃-1,2,4-triazolyl-5 | | 361 | 5-(4'-CH₃—C₆H₄)-1,3,4-thiadiazolyl-2 |
| 280 | 3-(4'-CN—C₆H₄)—N—CH₃-1,2,4-triazolyl-5 | | 362 | 5-(3'-CH₃—C₆H₄)-1,3,4-thiadiazolyl-2 |
| 281 | 3-(3'-CN—C₆H₄)—N—CH₃-1,2,4-triazolyl-5 | | 363 | 5-(2'-CH₃—C₆H₄)-1,3,4-thiadiazolyl-2 |
| 282 | 3-(2'-CN—C₆H₄)—N—CH₃-1,2,4-triazolyl-5 | | 364 | 5-(4'-CH₃O—C₆H₄)-1,3,4-thiadiazolyl-2 |
| 283 | 3-(4'-Cl—C₆H₄)—N—CH₃-1,2,4-triazolyl-5 | | 365 | 5-(3'-CH₃O—C₆H₄)-1,3,4-thiadiazolyl-2 |
| 284 | 3-(3'-Cl—C₆H₄)—N—CH₃-1,2,4-triazolyl-5 | | 366 | 5-(2'-CH₃O—C₆H₄)-1,3,4-thiadiazolyl-2 |
| 285 | 3-(2'-Cl—C₆H₄)—N—CH₃-1,2,4-triazolyl-5 | | 367 | 5-(4'-NO₂—C₆H₄)-1,3,4-thiadiazolyl-2 |
| 286 | 1,3,4-oxadiazolyl-2 | | 368 | 5-(3'-NO₂—C₆H₄)-1,3,4-thiadiazolyl-2 |
| 287 | 5-CH₃-1,3,4-oxadiazolyl-2 | | 369 | 5-(2'-NO₂—C₆H₄)-1,3,4-thiadiazolyl-2 |
| 288 | 5-C₆H₅-1,3,4-oxadiazolyl-2 | | 370 | 5-(4'-CN—C₆H₄)-1,3,4-thiadiazolyl-2 |
| 289 | 5-(4'-CH₃—C₆H₄)-1,3,4-oxadiazolyl-2 | | 371 | 5-(3'-CN—C₆H₄)-1,3,4-thiadiazolyl-2 |
| 290 | 5-(3'-CH₃—C₆H₄)-1,3,4-oxadiazolyl-2 | | 372 | 5-(2'-CN—C₆H₄)-1,3,4-thiadiazolyl-2 |
| 291 | 5-(2'-CH₃—C₆H₄)-1,3,4-oxadiazolyl-2 | | 373 | 5-(4'-Cl—C₆H₄)-1,3,4-thiadiazolyl-2 |
| 292 | 5-(4'-CH₃O—C₆H₄)-1,3,4-oxadiazolyl-2 | | 374 | 5-(3'-Cl—C₆H₄)-1,3,4-thiadiazolyl-2 |
| 293 | 5-(3'-CH₃O—C₆H₄)-1,3,4-oxadiazolyl-2 | | 375 | 5-(2'-Cl—C₆H₄)-1,3,4-thiadiazolyl-2 |
| 294 | 5-(2'-CH₃O—C₆H₄)-1,3,4-oxadiazolyl-2 | | 376 | pyridinyl-2 |
| 295 | 5-(4'-NO₂—C₆H₄)-1,3,4-oxadiazolyl-2 | | 377 | pyridinyl-4 |
| 296 | 5-(3'-NO₂—C₆H₄)-1,3,4-oxadiazolyl-2 | | 378 | pyridazinyl-3 |
| 297 | 5-(2'-NO₂—C₆H₄)-1,3,4-oxadiazolyl-2 | | 379 | pyridazinyl-4 |
| 298 | 5-(4'-CN—C₆H₄)-1,3,4-oxadiazolyl-2 | | 380 | pyridinyl-3 |
| 299 | 5-(3'-CN—C₆H₄)-1,3,4-oxadiazolyl-2 | | 381 | pyrimidinyl-4 |
| 300 | 5-(2'-CN—C₆H₄)-1,3,4-oxadiazolyl-2 | | 382 | pyrimidinyl-5 |
| 301 | 5-(4'-Cl—C₆H₄)-1,3,4-oxadiazolyl-2 | | 383 | pyrimidinyl-2 |
| 302 | 5-(3'-Cl—C₆H₄)-1,3,4-oxadiazolyl-2 | | | |
| 303 | 5-(2'-Cl—C₆H₄)-1,3,4-oxadiazolyl-2 | | | |
| 304 | 1,2,4-oxadiazolyl-3 | | | |
| 305 | 5-CH₃-1,2,4-oxadiazolyl-3 | | | |
| 306 | 5-C₆H₅-1,2,4-oxadiazolyl-3 | | | |
| 307 | 5-(4'-CH₃—C₆H₄)-1,2,4-oxadiazolyl-3 | | | |
| 308 | 5-(3'-CH₃—C₆H₄)-1,2,4-oxadiazolyl-3 | | | |
| 309 | 5-(2'-CH₃—C₆H₄)-1,2,4-oxadiazolyl-3 | | | |
| 310 | 5-(4'-CH₃O—C₆H₄)-1,2,4-oxadiazolyl-3 | | | |
| 311 | 5-(3'-CH₃O—C₆H₄)-1,2,4-oxadiazolyl-3 | | | |
| 312 | 5-(2'-CH₃O—C₆H₄)-1,2,4-oxadiazolyl-3 | | | |
| 313 | 5-(4'-NO₂—C₆H₄)-1,2,4-oxadiazolyl-3 | | | |
| 314 | 5-(3'-NO₂—C₆H₄)-1,2,4-oxadiazolyl-3 | | | |
| 315 | 5-(2'-NO₂—C₆H₄)-1,2,4-oxadiazolyl-3 | | | |
| 316 | 5-(4'-CN—C₆H₄)-1,2,4-oxadiazolyl-3 | | | |
| 317 | 5-(3'-CN—C₆H₄)-1,2,4-oxadiazolyl-3 | | | |
| 318 | 5-(2'-CN—C₆H₄)-1,2,4-oxadiazolyl-3 | | | |
| 319 | 5-(4'-Cl—C₆H₄)-1,2,4-oxadiazolyl-3 | | | |

TABLE 3

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 1 | (structure: thiazole with CH₃-phenyl-O-CH₂ substituent and C(=N-OCH₃)CO₂CH₃ group) | | 90 |
| 2 | (structure: thiazole with CH₃-phenyl-O-CH₂ substituent and C(=N-OCH₃)CO₂CH₃ group, isomer) | | 95 |
| 3 | (structure: 2-chlorophenyl-isoxazole with C(=N-OCH₃)CO₂CH₃ group) | | 67 |
| 4 | (structure: 2-chlorophenyl-isoxazole with C(=CH-OCH₃)CO₂CH₃ group) | | 98 |
| 5 | (structure: 1-phenylpyrazole with C(=N-OCH₃)CO₂CH₃ group) | | 71 |
| 6 | (structure: 1-phenylpyrazole with C(=N-OCH₃)CO₂CH₃ group, isomer) | | 45 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 7 | (1-phenylpyrazol-4-yl)–C(CO$_2$CH$_3$)=CH–OCH$_3$ | 7.55(s, 1H); 4.0(s, 3H); 3.85(s, 3H) | |
| 8 | (1-phenylpyrazol-4-yl)–C(CO$_2$CH$_3$)=CH–OCH$_3$ (isomer) | 6.9(s, 1H); 3.95(s, 3H); 3.85(s, 3H) | |
| 9 | (1-phenylpyrazol-4-yl)–C(CO$_2$CH$_3$)=CH–CH$_3$ | trans isomer: 7.15(q, 1H, J=7Hz); 3.85(s, 3H); 3.8(s, 3H) cis isomer: 6.5(q, 1H, J=7Hz); 3.85(s, 3H); 3.8(s, 3H) | |
| 10 | (1-phenylpyrazol-4-yl)–C(=N–OCH$_3$)–C(=O)–NH–CH$_3$ | | 97 |
| 11 | 2-(4-chlorophenyl)oxazol-4-yl–C(=N–OCH$_3$)–CO$_2$CH$_3$ | | 94 |
| 12 | 2-(4-chlorophenyl)oxazol-4-yl–C(=N–OCH$_3$)–CO$_2$CH$_3$ (isomer) | | 76 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 13 | (thiophene-CH$_2$-O-CH$_3$ with C(=NOCH$_3$)CO$_2$CH$_3$) | 4.1(s, 3H); 3.9(s, 3H) | |
| 14 | (thiophene-CH$_2$-O-(2-Cl-phenyl) with C(=NOCH$_3$)CO$_2$CH$_3$) | 4.12(s, 3H); 3.86(s, 3H) | |
| 15 | (thiophene-CH$_2$-O-(2-Cl-phenyl) with C(=NOCH$_3$)CO$_2$CH$_3$) | 4.02(s, 3H); 3.90(s, 3H) | |
| 16 | (thiophene-CH$_2$-O-(3-Cl-phenyl) with C(=NOCH$_3$)CO$_2$CH$_3$) | 4.1(s, 3H); 3.79(s, 3H) | |
| 17 | (thiophene-CH$_2$-O-(3-Cl-phenyl) with C(=NOCH$_3$)CO$_2$CH$_3$) | 4.01(s, 3H); 3.86(s, 3H) | |
| 18 | (thiophene-CH$_2$-P(=O)(OCH$_3$)$_2$ with C(=NOCH$_3$)CO$_2$CH$_3$) | | 75 |
| 19 | (thiophene-CH$_2$-S-(2-Cl-phenyl) with C(=CHCH$_3$)CO$_2$CH$_3$) | 1717, 1451, 1432, 1257, 1237, 1196, 1175, 1035, 747, 730 | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 20 | (structure) | 4.03(s, 3H); 3.84(s 3H) | |
| 21 | (structure) | 3.79(s 3H); 3.87(s 3H) | |
| 22 | (structure) | 4.01(s 3H); 3.90(s 3H) | |
| 23 | (structure) | 4.12(s, 3H); 3.91(s, 3H) | |
| 24 | (structure) | 4.10(s, 3H); 3.87(s, 3H) | |
| 25 | (structure) | 3.99(s, 3H); 3.89(s, 3H) | |
| 26 | (structure) | 4.02(s, 3H); 3.92(s, 3H) | |

TABLE 3-continued

Selected physical data of some compounds
Isomer A: non-polar isomer
Isomer B: polar isomer

| No. | Compound | IR ($cm^{-1}$) or $^1$H-NMR (ppm) | mp (° C.) |
|---|---|---|---|
| 27 | (thiophene with CH2-S-(2,5-dichlorophenyl); C(=NOCH3)CO2CH3) | 4.14(s, 3H); 3.91(s, 3H) | |
| 28 | (thiophene with CH2-S-naphthalen-2-yl; C(=N-OCH3)CO2CH3) | 3.99(s, 3H); 3.88(s, 3H) | |
| 29 | (thiophene with CH2-S-naphthalen-2-yl; C(=NOCH3)CO2CH3) | 4.04(s, 3H); 3.76(s, 3H) | |
| 30 | (N-benzylpyrrole-2-yl C(=NOCH3)CO2CH3) | Isomer A: 3.88(s, 3H); 3.82(s, 3H)<br>Isomer B: 4.01(s, 3H); 3.77(s, 3H) | |
| 31 | (N-(2-methylbenzyl)pyrrole-2-yl C(=NOCH3)CO2CH3) | 1733, 1461, 1438, 1319, 1286, 1221, 1072, 1035 776, 742, | |
| 32 | (N-(3-methylbenzyl)pyrrole-2-yl C(=NOCH3)CO2CH3) | 1733, 1464, 1438, 1319, 1285, 1214, 1072, 1035, 776, 729 | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 33 | (1-(4-methylbenzyl)pyrrol-2-yl)(methoxyimino)acetic acid methyl ester | 1733, 1438, 1322, 1285, 1217, 1072, 1035, 1005, 776, 726 | |
| 34 | (1-(2-fluorobenzyl)pyrrol-2-yl)(methoxyimino)acetic acid methyl ester | 1732, 1492, 1458, 1438, 1285, 1230, 1215, 1071, 1034, 758 | |
| 35 | (1-(3-fluorobenzyl)pyrrol-2-yl)(methoxyimino)acetic acid methyl ester | 1733, 1591, 1489, 1452, 1438, 1286, 1216, 1072, 1035, 777 | |
| 36 | (1-(4-fluorobenzyl)pyrrol-2-yl)(methoxyimino)acetic acid methyl ester | 1733, 1510, 1439, 1321, 1285, 1223, 1159, 1072, 1035, 727 | |
| 37 | (1-(2-bromobenzyl)pyrrol-2-yl)(methoxyimino)acetic acid methyl ester | 1731, 1439, 1320, 1287, 1218, 1071, 1035, 776, 747, 727 | |
| 38 | (1-(3-bromobenzyl)pyrrol-2-yl)(methoxyimino)acetic acid methyl ester | 1733, 1437, 1429, 1318, 1285, 1217, 1071, 1035, 776, 727 | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 39 | (1-(4-bromobenzyl)pyrrol-2-yl methyl(methoxyimino)acetate) | 1731, 1488, 1437, 1285, 1217, 1071, 1035, 1011, 726 | |
| 40 | (1-(2-(methoxycarbonyl)benzyl)pyrrol-2-yl methyl(methoxyimino)acetate) | 1723, 1436, 1285, 1215, 1201, 1072, 1035, 736 | |
| 41 | (1-benzoylpyrrol-2-yl methyl(methoxyimino)acetate) | 4.01(s, 3H); 3.77(s, 3H) | |
| 42 | (isoxazole derivative with 4-methoxybenzoate) | Isomer A: 4.06(s, 3H); 3.96(s, 3H); 3.87(s, 3H) Isomer B: 4.17(s, 3H); 3.92(s, 3H); 3.86(s, 3H) | |
| 43 | (isoxazole derivative with 3-nitrobenzoate) | Isomer A: 4.07(s, 3H); 3.96(s, 3H) Isomer B: 4.20(s, 3H); 3.94(s, 3H) | |
| 44 | (isoxazole derivative with phthalimidoxy) | 4.17(s, 3H); 3.92(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 45 | | 4.16(s, 3H); 3.92(s, 3H) | |
| 46 | | 4.12(s, 3H); 3.91(s, 3H) | |
| 47 | | 4.21(s, 3H); 3.96(s, 3H) | |
| 48 | | Isomer A: 3.85(s, 3H); 3.65(s, 3H) Isomer B: | 49 |
| 49 | | Isomer A: 4.0(s, 3H); 3.95(s, 3H) Isomer B: | 56 |
| 50 | | | 72 |
| 51 | | Isomer A: 3.95(s, 3H); 3.95(s, 3H) Isomer B: | 58 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 52 | | Isomer A:<br>Isomer B: | 136<br>113 |
| 53 | | Isomer A:<br>Isomer B: | 150<br>112 |
| 54 | | Isomer A:<br>Isomer B: | 138<br>112 |
| 55 | | | 110 |
| 56 | | | 84 |
| 57 | | 4.05(s, 3H); 3.95(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 58 | | 4.15(s, 3H); 3.85(s, 3H) | |
| 59 | | | 106 |
| 60 | | 4.1(s, 3H); 3.9(s, 3H) | |
| 61 | | 4.1(s, 3H); 4.0(s, 3H) | |
| 62 | | 4.1(s, 3H); 3.9(s, 3H) | |
| 63 | | | 81 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 64 | | | 85 |
| 65 | | | 85 |
| 66 | | 4.1(s, 3H); 3.9(s, 3H) | |
| 67 | | | 64 |
| 68 | | 4.1(s, 3H); 3.9(s, 3H) | |
| 69 | | 4.05(s, 3H); 3.95(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 70 | | 4.1(s, 3H); 3.9(s, 3H) | |
| 71 | | 4.05(s, 3H); 3.95(s, 3H) | |
| 72 | | 4.1(s, 3H); 3.9(s, 3H) | |
| 73 | | | 61 |
| 74 | | | 74 |
| 75 | | | 65 |
| 76 | | | 73 |

TABLE 3-continued
Selected physical data of some compounds
Isomer A: non-polar isomer
Isomer B: polar isomer
| No. | Compound | IR (cm⁻¹) or ¹H-NMR (ppm) | mp (° C.) |
|---|---|---|---|
| 77 | 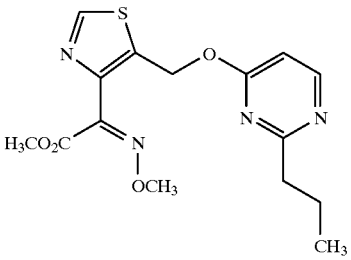 | 4.05(s, 3H); 3.95(s, 3H) | |
| 78 | 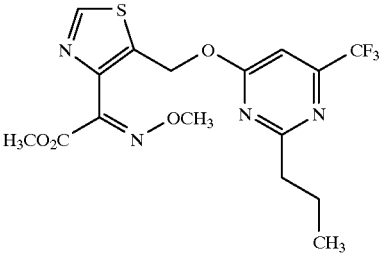 | | 59 |
| 79 | 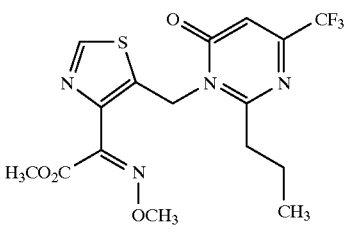 | | 107 |
| 80 | 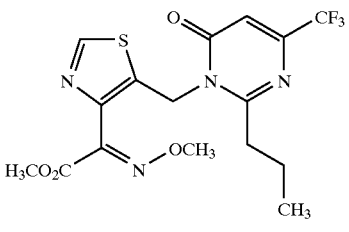 | | 94 |
| 81 | 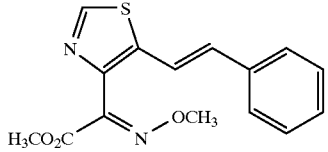 | | 108 |

TABLE 3-continued
Selected physical data of some compounds
Isomer A: non-polar isomer
Isomer B: polar isomer
| No. | Compound | IR (cm$^{-1}$) or $^1$H-NMR (ppm) | mp (° C.) |
|---|---|---|---|
| 82 | 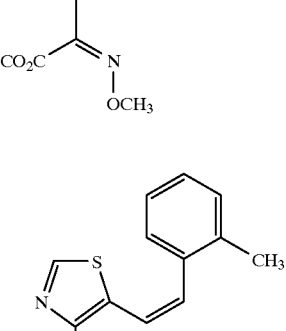 | | 67 |
| 83 | 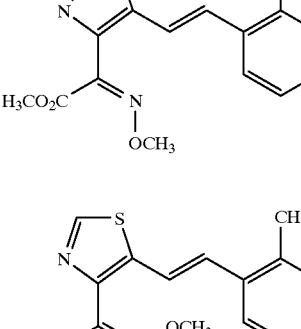 | 4.1(s, 3H); 3.9(s, 3H) | |
| 84 | 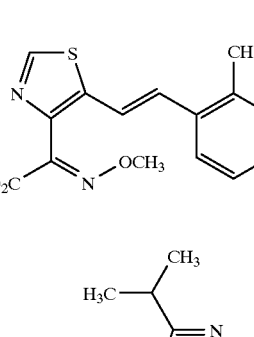 | | 86 |
| 85 | 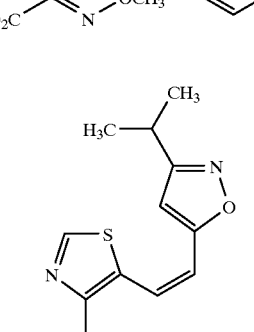 | | 94 |
| 86 | 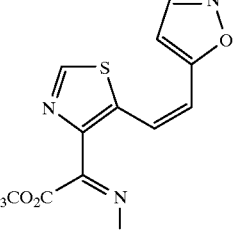 | 4.05(s, 3H); 3.95(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 87 | (structure) | 4.1(s, 3H); 3.9(s, 3H) | |
| 88 | (structure) | | 87 |
| 89 | (structure) | | 139 |
| 90 | (structure) | | 156 |
| 91 | (structure) | | 169 |
| 92 | (structure) | | 82 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 93 | | 4.1(s, 3H); 3.95(s, 3H) | |
| 94 | | 4.2(s, 3H); 3.95(s, 3H) | |
| 95 | | | 77 |
| 96 | | | 87 |
| 97 | | 4.0(s, 3H); 3.55(s, 3H) | |
| 98 | | | 98 |
| 99 | | 4.05(s, 3H); 4.0(s, 3H); 3.7(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 100 | | 4.05(s, 3H); 3.8(s, 3H); 3.75(s, 3H) | |
| 101 | | 4.05(s, 3H); 3.8(s, 3H); 3.7(s, 3H) | |
| 102 | | 4.1(s, 3H); 3.85(s, 3H); 3.75(s, 3H) | |
| 103 | | 4.05(s, 3H); 3.95(s, 3H); 3.8(s, 3H) | |
| 104 | | | 129 |
| 105 | | 4.05(s, 3H); 3.95(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 106 | | 4.1(s, 3H); 3.9(s, 3H) | |
| 107 | | | 116 |
| 108 | | | 98 |
| 109 | | | 136 |
| 110 | | | 82 |
| 111 | | | 79 |
| 112 | | 4.1(s, 3H); 3.9(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 113 | | 4.05(s, 3H); 3.9(s, 3H) | |
| 114 | | 4.1(s, 3H); 3.9(s, 3H) | |
| 115 | | | 85 |
| 116 | | 4.1(s, 3H); 3.9(s, 3H) | |
| 117 | | | 100 |
| 118 | | 4.1(s, 3H); 3.9(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 119 | | | 78 |
| 120 | | | 93 |
| 121 | | | 63 |
| 122 | | | 88 |
| 123 | | | 93 |
| 124 | | | 93 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 125 | | 4.1(s, 3H); 3.95(s, 3H) | |
| 126 | | | 58 |
| 127 | | | 74 |
| 128 | | | 72 |
| 129 | | 4.1(s, 3H); 3.95(s, 3H) | |
| 130 | | | 91 |
| 131 | | 4.15(s, 3H); 3.9(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 132 | | | 106 |
| 133 | | | 125 |
| 134 | | | 83 |
| 135 | | | 99 |
| 136 | | | 126 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 137 | | 4.1(s, 3H); 3.9(s, 3H) | |
| 138 | | 4.05(s, 3H); 3.7(s, 3H) | |
| 139 | | 3.82(s, 3H); 3.80(s, 3H) | |
| 140 | | 4.05(s, 3H); 3.75(s, 3H) | |
| 141 | | 3.82(s, 3H); 3.80(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 142 | (structure) | 4.0(s, 3H); 3.85(s, 3H) | |
| 143 | (structure) | 4.1(s, 3H); 3.85(s, 3H) | |
| 144 | (structure) | 4.15(s, 3H); 3.9(s, 3H) | |
| 145 | (structure) | | 82 |
| 146 | (structure) | 4.05(s, 3H); 3.95(s, 3H) | |
| 147 | (structure) | | 65 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 148 | (thiazole with CH$_2$Br, C(=NOCH$_3$)CO$_2$CH$_3$) | 4.1(s, 3H); 3.95(s, 3H) | |
| 149 | (thiazole with CH$_2$Br, C(=NOCH$_3$)CO$_2$CH$_3$) | 4.15(s, 3H); 3.9(s, 3H) | |
| 150 | (thiazole-CH$_2$-O-aryl with CH$_3$, C(CH$_3$)=NOCH(CH$_3$)$_2$) | | 107 |
| 151 | (thiazole-CH$_2$-O-aryl with CH$_3$, C(CH$_3$)=NOCH(CH$_3$)$_2$) | | 87 |
| 152 | (thiazole-CH$_2$-O-aryl, CH$_3$NHC(O)-C(=NOCH$_3$)-, aryl-C(CH$_3$)=NOCH(CH$_3$)$_2$) | | 147 |
| 153 | (isoxazole with CH$_3$, C(=NOCH$_3$)CO$_2$CH$_3$) | 4.1(s, 3H); 3.95(s 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 154 | (isoxazole with 4-CH$_3$, 5-C(=NOCH$_3$)CO$_2$CH$_3$) | 4.2(s, 3H); 3.9(s, 3H) | |
| 155 | (isoxazole with 4-CH$_2$Br, 5-C(=NOCH$_3$)CO$_2$CH$_3$) | 4.15(s, 3H); 4.0(s, 3H) | |
| 156 | (isoxazole with 4-Br, 5-C(=NOCH$_3$)CO$_2$CH$_3$) | | 45 |
| 157 | (isoxazole with 4-CHBr$_2$, 5-C(=NOCH$_3$)CO$_2$CH$_3$) | 4.2(s, 3H); 3.95(s, 3H) | |
| 158 | (isoxazole with 4-CHBr$_2$, 5-C(=NOCH$_3$)CO$_2$CH$_3$) | 4.25(s, 3H); 3.95(s, 3H) | |
| 159 | (isoxazole with 4-CHO, 5-C(=NOCH$_3$)CO$_2$CH$_3$) | 4.25(s, 3H); 3.95(s, 3H) | |
| 160 | (1-phenyl-pyrazole with 5-CHO, 4-C(=NOCH$_3$)CO$_2$CH$_3$) | 4.15(s, 3H); 3.9(s, 3H) | |

TABLE 3-continued
Selected physical data of some compounds
Isomer A: non-polar isomer
Isomer B: polar isomer
| No. | Compound | IR (cm$^{-1}$) or $^1$H-NMR (ppm) | mp (° C.) |
|---|---|---|---|
| 161 | 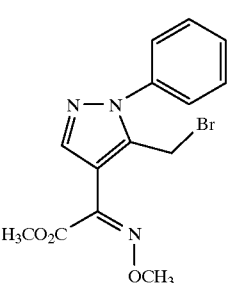 | 4.05(s, 3H); 3.95(s, 3H) | |
| 162 | 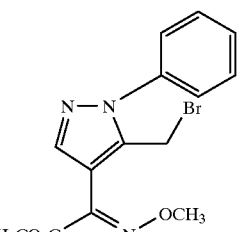 | 4.2(s, 3H); 3.95(s, 3H) | |
| 163 | 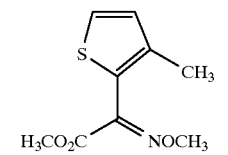 | Isomer A:<br>4.15(s, 3H); 3.9(s, 3H)<br>Isomer B:<br>4.05(s, 3H); 3.95(s, 3H) | |
| 164 | 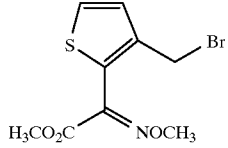 | Isomer A:<br>4.15(s, 3H); 3.9(s, 3H)<br>Isomer B:<br>4.05(s, 3H); 3.95(s, 3H) | |
| 165 | 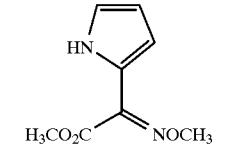 | 4.15(s, 3H); 3.9(s, 3H) | |
| 166 | 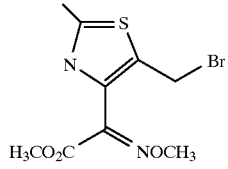 | 2 isomers:<br>4.2(s, 3H); 3.9(s, 3H)<br>and<br>4.1(s, 3H); 4.0(s, 3H) | |
| 167 | 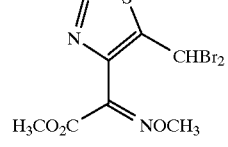 | 2 isomers:<br>4.2(s, 3H); 3.95(s, 3H)<br>and<br>4.15(s, 3H); 4.0(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 168 | (thiazole with CHO, C(=NOCH$_3$)CO$_2$CH$_3$) | 4.15(s, 3H); 4.0(s, 3H) | |
| 169 | (thiazole with CH$_2$P(=O)(OC$_2$H$_5$)$_2$, CH(N(OCH$_3$))CO$_2$CH$_3$) | 4.15(s, 3H); 3.9(s, 3H) | |
| 170 | (2-Br-4-methyl-thiazole with C(=NOCH$_3$)CO$_2$CH$_3$) | 4.15(s, 3H); 3.9(s, 3H) | |
| 171 | (isoxazole with CH$_2$P(=O)(OC$_2$H$_5$)$_2$, C(=NOCH$_3$)CO$_2$CH$_3$) | 4.1(s, 3H); 3.95(s, 3H) | |
| 172 | (isoxazole with CH$_2$OH, C(=NOCH$_3$)CO$_2$CH$_3$) | 4.1(s 3H); 4.0(s 3H) | |
| 173 | (pyrazole NH with CH$_3$, C(=NOCH$_3$)CO$_2$CH$_3$) | 2 isomers:<br>4.0(s, 3H); 3.8(s, 3H)<br>and<br>4.1(s, 3H); 3.9(s, 3H) | |
| 174 | (N-methyl pyrazole with CH$_3$, C(=NOCH$_3$)CO$_2$CH$_3$) | 2 isomers:<br>4.02(s, 3H); 3.95(s, 3H);<br>3.88(s, 3H)<br>and<br>4.15(s, 3H); 3.9(s, 3H);<br>3.7(s, 3H) | |

TABLE 3-continued
Selected physical data of some compounds
Isomer A: non-polar isomer
Isomer B: polar isomer
| No. | Compound | IR (cm$^{-1}$) or $^1$H-NMR (ppm) | mp (° C.) |
|---|---|---|---|
| 175 | 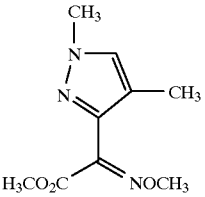 | 2 isomers:<br>3.97(s, 3H); 3.92(s, 3H);<br>3.8(s, 3H)<br>and<br>4.1(s, 3H); 3.85(s, 6H) | |
| 176 | 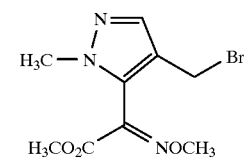 | 4.1(s, 3H); 3.95(s, 6H) | |
| 177 | 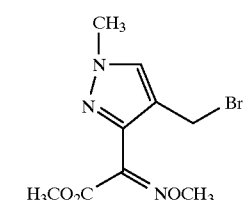 | Isomer A:<br>4.05(s, 3H), 4.95(s, 3H);<br>4.85(s, 3H)<br>Isomer B:<br>4.15(s, 3H); 3.9(s, 6H) | |
| 178 | 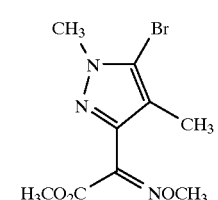 | 4.0(s, 3H); 3.95(s, 3H);<br>3.85(s, 3H) | |
| 179 | 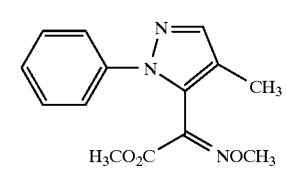 | 2 isomers:<br>4.05(s, 3H); 3.65(s, 3H)<br>and<br>4.0(s, 3H); 3.45(s, 3H) | |
| 180 | 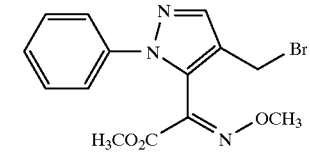 | 4.1(s, 3H); 3.65(s, 3H) | |
| 181 | 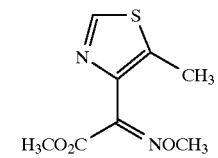 | 4.15(s, 3H); 3.95(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 182 | (2-bromo-4-methyl-thiazol-5-yl with C(=NOCH$_3$)CO$_2$CH$_3$) | 4.15(s, 3H); 3.9(s, 3H) | |
| 183 | (5-methyl-isoxazol-4-yl with C(=NOCH$_3$)CO$_2$CH$_3$) | 4.0(s, 6H) | |
| 184 | (5-bromomethyl-isoxazol-4-yl with C(=NOCH$_3$)CO$_2$CH$_3$) | 2 isomers:<br>4.1(s, 3H); 4.0(s, 3H)<br>and<br>4.05(s, 3H); 3.9(s, 3H) | |
| 185 | (5-methoxymethyl-1H-pyrazol-4-yl with C(=NOCH$_3$)CO$_2$CH$_3$) | 4.1(s, 3H); 3.9(s, 3H) | |
| 186 | (5-methoxymethyl-1-methyl-pyrazol-4-yl with C(=NOCH$_3$)CO$_2$CH$_3$) | 4.1(s, 3H); 3.9(s, 6H) | |
| 187 | (3-methoxymethyl-1-methyl-pyrazol-4-yl with C(=NOCH$_3$)CO$_2$CH$_3$) | 4.1(s, 3H); 3.9(2s, 6H) | |
| 188 | (4-methoxymethyl-1H-pyrazol-3-yl with C(=NOCH$_3$)CO$_2$CH$_3$) | 4.0(s, 3H); 3.9(s, 3H) | |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 189 | (2-methyl-thiazol-4-yl with 5-CH$_2$OCH$_3$; H$_3$CO$_2$C–C(=NOCH$_3$)–) | 4.0(s, 3H); 3.95(s, 3H) | |
| 190 | (pyrimidin-4-yl with 5-CH$_2$Br; H$_3$CO$_2$C–C(=NOCH$_3$)–) | 2 isomers:<br>4.3(s, 3H); 4.0(s, 3H)<br>and<br>4.15(S, 3H) 3.95(S, 3H) | |
| 191 | (1-methyl-pyrazol-4-yl with 5-CH$_2$Br; H$_3$CO$_2$C–C(=NOCH$_3$)–) | 2 isomers:<br>4.1(s, 2×3H); 4.05(s, 3H);<br>3.9(s, 3H); 3.35(s, 2×3H) | |
| 192 | (1H-pyrazol-4-yl with 5-CH$_2$O-(2-methylphenyl); H$_3$CO$_2$C–C(=NOCH$_3$)–) | 4.05(s, 3H) 3.7(s, 3H) | |
| 193 | (1H-pyrazol-4-yl with 5-CH$_2$O-(2-methylphenyl); H$_3$C-NH-C(=O)–C(=NOCH$_3$)–) | | 47 |
| 194 | (isoxazol-4-yl with 5-CH$_2$O-(2-methylphenyl); H$_3$CO$_2$C–C(=NOCH$_3$)–) | 4.1(s, 3H); 3.75(s, 3H) | |
| 195 | (1-methyl-pyrazol-3-yl with CH$_2$O-(2-methylphenyl); H$_3$CO$_2$C–C(=NOCH$_3$)–) | | 54 |

TABLE 3-continued

Selected physical data of some compounds
Isomer A: non-polar isomer
Isomer B: polar isomer

| No. | Compound | IR (cm$^{-1}$) or $^1$H-NMR (ppm) | mp (° C.) |
|---|---|---|---|
| 196 | 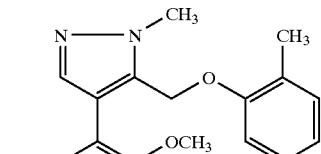 | 4.0(s, 3H); 3.95(s, 3H); 3.8(s, 3H) | |
| 197 | 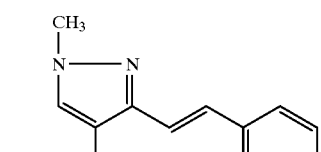 | 4.1(s, 3H); 3.9(s, 3H); 3.85(s, 3H) | |
| 198 | 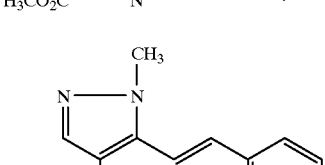 | 4.1(s, 3H); 3.9(s, 3H); 3.75(s, 3H) | |

The novel compounds are suitable as fungicides, insecticides, nematicides and for regulating the growth of plants.

The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chloroblenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanois, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethyiene octylphenol ethers, ethoxylated isooctyiphenol, ethoxylated octylphenol and ethoxylated nonylphenol, alkylphenol polyglycol ethers, tributyiphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, luryl alcohol lpolyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of compound no. 1 from Table 3 and 10 parts by weight of N-methyl-α-pyrrolidone, which is suitable for application in the form of very fine drops.

II. A mixture of 20 parts by weight of compound no. 2 from Table 3, 80 parts by weight of xylene, 10 parts by weight of the adduct of 8 to 10 moles of ethylene oxide and 1 mole of oleic azid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 3 from Table 3, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 4 from Table 3, 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil.

V. A hammer-milled mixture of 80 parts by weight of compound no. 5 from Table 3, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 6 from Table 3 and 97 parts by weight of particulate kaolin. The dust contains 3 wt % of the active ingredient.

VII. An intimate mixture of 30 parts by weight of compound no. 7 from Table 3, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 8 from Table 3, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 9 from Table 3, 2 parts by weight of the calcium salt of dodecylbenzenesulfonic acid, 8 parts by weight of a fatty alcohol polyglycol ether, 2 parts by weight of the sodium salt of a phenolsulfonlc acid-ureaformaldehyde condensate and 68 parts by weight of a paraffinic mineral oil.

The compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi or the seeds, plants, materials or the soil to be protected against fungus attack with an. effective amount of the active ingredients.

Application may be effected before or after infection of the materials, plants or seed by the fungi.

The compounds I are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
*Ustilago* species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercosrora arachidicola* in groundnuts,
*Pseudocercosporeila herpotrichoides* in wheat and barley,
*Pyricularia oryzae* in rice,
*Phytoptithora infestaris* in potatoes and tomatoes,
*Fusarium* and *Verticillium* species in various plants,
*Plasmopara viticola* in grapes,
Alternaria species in fruit and vegetables.

The novel compounds may also be used for protecting materials (timber) against, for example, Paecilomyces variotii.

Generally, the fungicidal agents contain from 0.1 to 95, and preferably from 0.5 to 90, wt % of active ingredient.

The application rates depend on the effect desired, and vary from 0.02 to 3 kg of active ingredient per hectare.

When the active ingredients are used for treating seed, rates of from 0.001 to 50, and preferably from 0.01 to 10, g per kg of seed are generally needed.

When applied as fungicides, the agents according to the invention may also be present together with other active ingredients, for example herbicides, insecticides, growth regulators, other fungicides, or fertilizers.

When admixed with other fungicides, the fungicidal spectrum of action is in many cases increased.

Use examples

The active ingredient used for comparison purposes was methyl 2-(2-methylphenyl)-3-methoxyacrylate (A) disclosed in EP 178 826.

Use Example 1

Action on Plasmopara viticola

Leaves of potted vines of the Muller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20 to 30° C. To accelerate and intensify the sporangiophore discharge, the plants were then again placed in the moist chamber for 16 hours. The extent of fungus attack was then assessed on the undersides of the leaves.

The results show that active ingredients nos. 17, 23, 24, 27, 29, 60, 62, 64, 66, 70, 91, 101, 102, 112, 113, 122, 123, 124, 126, 130 and 134 from Table 3, when applied as spray liquors containing 250 ppm (by weight) of active ingredient, have a better fungicidal action (90%) than prior art comparative agent A (0%).

Use Example 2
Action on Pyricuiaria oryzae (protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of Pyricular cycloalkyl-S(=O)—O—, cycloalkenyl-S(=O)—O—, heterocyclyl-S(=O)—O—, aryl-S(=O)—O—, hetaryl-S(=O)—O—;

unsubstituted or substituted alkyl-O—S(=O)—, alkenyl-O—S(=O)—, alkynyl-O—S(=O)—, cycloalkyl-O—S(=O)—, cycloalkenyl-O—S(=O)—, heterocyclyl-O—S(=O)—, aryl-O—S(=O)—, hetaryl-O—S(=O)—;

unsubstituted or substituted alkyl-S(=O)$_2$—, alkenyl-S(=O)$_2$—, alkynyl-S(=O)$_2$—, cycloalkyl-S(=O)$_2$—, cycloalkenyl-S(=O)$_2$—, heterocyclyl-S(=O)$_2$—, aryl-S(=O)$_2$—, hetaryl-S(=O)$_2$—;

unsubstituted or substituted alkyl-O—S(=O)$_2$—O—, alkenyl-O—S(=O)$_2$—O—, alkynyl-O—S(=O)$_2$—, alkynyl-O—S(=O)$_2$—, cycloalkyl-O—S(=O)$_2$—, cycloalkenyl-O—S(=O)$_2$—, heterocyclyl-O—S(=O)$_2$—, aryl-O—S(=O)$_2$—, hetaryl-O—S(=O)$_2$—;

unsubstituted or substituted alkyl-ON=CR$^8$—, alkenyl-ON=CR$^8$—, alkynyl-ON=CR$^8$—, cycloalkyl-ON=CR$^8$, cycloalkenyl-ON=CR$^8$—, heterocyclyl-ON=CR$^8$—, aryl-ON=CR$^8$—, hetaryl-ON=CR$^8$—;

R$^8$ is hydrogen, cyano;

unsubstituted or substituted alkyl, alkenyl, alkynyl, cycloalkyl, cycloalkenyl, cycloalkynyl, heterocyclyl, aryl, or hetaryl;

unsubstituted or substituted alkoxy, alkenyloxy, alkynyloxy, cycloalkoxy, cycloalkenyloxy, cycloalkynyloxy, heterocyclyloxy, aryloxy or hetaryloxy;

Q is oxygen or a substituted nitrogen;

and its plant-tolerated acid addition products and base addition products.

2. The heteroaromatic compound of claim 1, wherein R$^1$ is methoxy, or methylamino R$^2$ is methyl, X is hydrogen, halogen, C$_1$–C$_4$-alkyl, C$_1$–C$_4$-haloalkyl, C$_3$–C$_6$-cycloalkyl, C$_1$–C$_4$-alkoxy, C$_1$–C$_4$-haloalkoxy, or C$_1$–C$_4$-alkylthio, A is oxygen, sulfur, CH$_2$O, CH=CH, CH$_2$O—N=CR$^7$, or O—N=CR$^7$, R$^7$ is hydrogen, cyano, C$_1$–C$_4$-alkyl, C$_1$–C$_4$-haloalkyl, C$_3$–C$_6$-cycloalkyl, C$_1$–C$_4$-alkoxy, C$_1$–C$_4$-haloalkoxy, or C$_1$–C$_4$-alkylthio, B is unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocyclyl, unsubstituted or substituted aryl, or unsubstituted or substituted hetaryl.

3. The compound of claim 1, wherein R$^1$ is methoxy.

4. The compound of claim 1, wherein R$^2$ is methyl.

5. The compound of claim 1, wherein B is unsubstituted or substituted aryl.

6. The compound of claim 1, wherein A is —(CHR$^4$)$_n$O—.

7. A fungicide composition, comprising:

an inert carrier and a fungicidal amount of a heteroaromatic compound of the formula:

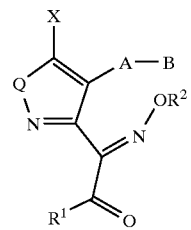

wherein R$^1$ and C$_1$–C$_6$-alkyl, C$_1$–C$_6$-alkoxy, C$_1$–C$_6$-alkylamino or di-C$_1$–C$_6$-alkylamino;

R$^2$ is C$_1$–C$_6$-alkyl;

A is a direct bond; unsubstituted or substituted alkylene, alkenylene or alkynylene;

—(CHR$^4$)$_n$—O—, —(CHR$^4$)$_n$—S—, —(CHR$^4$)$_n$—NH—, —(CHR$^4$)$_n$—NR$_5$—, —(CHR$^4$)$_n$—S(=O)—, —(CHR$^4$)$_n$—S(=O)$_2$—, —(CHR$^4$)$_n$—O—S(=O)—, —(CHR$^4$)$_n$—S(=O)—O—, —(CHR$^4$)$_n$—O—S(=O)$_2$—, —(CHR$^4$)$_n$—S(=O)$_2$—O—, —(CHR$^4$)$_n$—C(=O)—, —(CHR$^4$)$_n$—C(=O)O—, —(CHR$^4$)$_n$—O—C(=O)—, —(CHR$^4$)$_n$—CR$^5$=N—O—, —(CHR$^4$)$_n$—CR$^5$=N—N=CR$^6$—, —(CHR$^4$)$_n$—O—N=CR$^7$—, n is 0, 1, 2, 3 or 4, and the R$^4$'s are the same or different, when is greater than 1;

R$^4$, R$^5$ and R$^6$ independently of one another are each hydrogen or unsubstituted or substituted C$_1$–C$_6$-alkyl, C$_2$–C$_6$-alkenyl, C$_2$–C$_6$-alkynyl or aryl;

R$^7$ is hydrogen, cyano;

unsubstituted or substituted alkyl, alkenyl, alkynyl, cycloalkyl, cycloalkenyl, cycloalkynyl, heterocyclyl, aryl, hetaryl;

unsubstituted or substituted alkoxy, alkenyloxy, alkynyloxy, cycloalkoxy, cycloalkenyloxy, cycloalkynyloxy, heterocyclyloxy, aryloxy, hetaryloxy;

or R$^7$ and B, together with the carbon atom to which they are bonded, form an unsubstituted or substituted, saturated or partially unsaturated alicyclic or heterocylic ring system;

B is hydrogen, halogen, unsubstituted or substituted alkyl, alkenyl, alkynyl; cycloalkyl, cycloalkenyl, cycloalkynyl, heterocyclyl, aryl, hetaryl, —(CHR$^4$)$_p$-cycloalkyl, —(CHR$^4$)$_p$-cycloalkenyl, —(CHR$^4$)$_p$-cycloalkenyl, —(CHR$^4$)$_p$-heterocyclyl, —(CHR$^4$)$_p$-aryl, —(CHR$^4$)$_p$-hetaryl, —(CHR$^4$)$_p$—O-cycloalkyl, —(CHR$^4$)$_p$—O-cycloalkenyl, —(CHR$^4$)$_p$—O-cycloalkenyl, —(CHR$^4$)$_p$—O-heterocyclyl, —(CHR$^4$)$_p$—O-aryl, —(CHR$^4$)$_p$—O-hetaryl, —(CHR$^4$)$_p$—S-cycloalkyl, —(CHR$^4$)$_p$—S-cycloalkenyl, —(CHR$^4$)$_p$—S-cycloalkynyl, —(CHR$^4$)$_p$—S-heterocyclyl, —(CHR$^4$)$_p$—S-aryl, —(CHR$^4$)$_p$—S-hetaryl, —(CHR$^4$)$_p$—NH-cycloalkyl, —(CHR$^4$)$_p$—NH-cycloalkenyl, —(CHR$^4$)$_p$—NH-cycloalkynyl, —(CHR$^4$)$_p$—NH-heterocyclyl, —(CHR$^4$)$_p$—NH-aryl, —(CHR$^4$)$_p$—NH-hetaryl, —(CHR$^4$)$_p$—NR$^5$-cycloalkyl, —(CHR$^4$)$_p$—NR$^5$-cycloalkenyl, —(CHR$^4$)$_p$—NR$^5$-cycloalkynyl, —(CHR$^4$)$_p$—NR$^5$-heterocyclyl, —(CHR$^4$)$_p$—NR$^5$-aryl, —(CHR$^4$)$_p$—NR$^5$-hetarayl, wherein the above-mentioned cyclic groups may in turn carry substituents;

p is 1, 2, 3 or 4, and the R$^4$'s are the same or different when n is greater than 1;

x is hydrogen, cyano, nitro, halogen, haloalkyl, haloalkoxy, unsubstituted or substituted alkyl, alkenyl, alkynyl, cycloalkyl, cycloalkenyl, heterocyclyl, aryl, hetaryl;

unsubstituted or substituted alkoxy, alkenyloxy, alkynyloxy, cycloalkoxy, cycloalkenyloxy, heterocyclyloxy, aryloxy, hetaryloxy;

unsubstituted or substituted alkylthio, alkenylthio, alkynylthio, cycloalkylthio, cycloalkenylthio, heterocyclylthio, arythio, hetarylthio;

amino which may carry one or two of the following groups:

unsubstituted or substituted alkyl, alkenyl, alkynyl, cycloalkyl, cycloalkenyl, heterocyclyl, aryl and/or hetaryl;

unsubstituted or substituted alkylcarbonyl, alkenylcarbonyl, alkynylcarbonyl, cycloalkylcarbonyl, cycloalkenylcarbonyl, heterocyclylcarbonyl, arylcarbonyl, hetarylcarbonyl;

unsubstituted or substituted alkylcarbonyloxy, alkenylcarbonyloxy, alkynylcarbonyloxy, cycloalkylcarbonyloxy, cycloalkenylcarbonyloxy, heterocyclycarbonyloxy, arylcarbonyloxy, hetarylcarbonyloxy;

unsubstituted or substituted alkoxycarbonyl, alkenyloxycarbonyl, alkynyloxycarbonyl, cycloalkoxycarbonyl, cycloalkenyloxycarbonyl, heterocyclyloxycarbonyl, aryloxycarbonyl, hetaryloxycarbonyl;

unsubstituted or substituted alkylcarbonylamino, alkenylcarbonylamino, alkynylcarbonylamino, cyclalkylcarbonylamino, cycloalkenylcarbonylamino, heterocyclylcarbonylamino, arylcarbonylamino or hetarylcarbonylamino, where these groups optionally carry one of the following groups on the amino group:

unsubstituted or substituted alkyl, alkenyl, alkynyl, cycloalkyl, cycloalkenyl, heterocyclyl, aryl and/or hetaryl;

aminocarbonyl which may carry one or two of the following groups on the amino group:

unsubstituted or substituted alkyl, alkenyl, alkynyl, cycloalkyl, cycloalkenyl, heterocyclyl, aryl and/or hetaryl;

unsubstituted or substituted alkyl-S(=O)—, alkenyl-S(=O)—, alkynyl-S(=O)—, cycloalkyl-S(=O)—, cycloalkenyl-S(=O)—, heterocyclyl-S(=O)—, aryl-S(=O)—, hetaryl-S(=O)—;

unsubstituted or substituted alkyl-S(=O)—O—, alkenyl-S(=O)—O—, alkynyl-S(=O)—O—, cycloalkyl-S(=O)—O—, cycloalkenyl-S(=O)—O—, heterocyclyl-S(=O)—O—, aryl-S(=O)—O—, hetaryl-S(=O)—O—;

unsubstituted or substituted alkyl-O—S(=O)—, alkenyl-O—S(=O)—, alkynyl-O—S(=O)—, cycloalkyl-O—S(=O)—, cycloalkenyl-O—S(=O)—, heterocyclyl-O—S(=O)—, aryl-O—S(=O)—, hetaryl-O—S(=O)—;

unsubstituted or substituted alkyl-S(=O)$_2$—, alkenyl-S(=O)$_2$—, alkynyl-S(=O)$_2$—, cycloalkyl-S(=O)$_2$—, cycloalkenyl-S(=O)$_2$—, heterocyclyl-S(=O)$_2$—, aryl-S(=O)$_2$—, hetaryl-S(=O)$_2$—;

unsubstituted or substituted alkyl-O—S(=O)$_2$—O—, alkenyl-O—S(=O)$_2$—O—, alkynyl-O—S(=O)$_2$—, alkynyl-O—S(=O)$_2$—, cycloalkyl-O—S(=O)$_2$—, cycloalkenyl-O—S(=O)$_2$—, heterocyclyl-O—S(=O)$_2$—, aryl-O—S(=O)$_2$—, hetaryl-O—S(=O)$_2$—;

unsubstituted or substituted alkyl-ON=CR$^8$—, alkenyl-ON=CR$^8$—, alkynyl-ON=CR$^8$—, cycloalkyl-ON=CR$^8$, cycloalkenyl-ON=CR$^8$—, heterocyclyl-ON=CR$^8$—, aryl-ON=CR$^8$—, hetaryl-ON=CR$^8$—;

$R^8$ is hydrogen, cyano;

unsubstituted or substituted alkyl, alkenyl, alkynyl, cycloalkyl, cycloalkenyl, cycloalkynyl, heterocyclyl, aryl, or hetaryl;

unsubstituted or substituted alkoxy, alkenyloxy, alkynyloxy, cycloalkoxy, cycloalkenyloxy, cycloalkynyloxy, heterocyclyloxy, aryloxy or hetaryloxy;

Q is oxygen or a substituted nitrogen;

and its plant-tolerated acid addition products and base addition products.

8. The fungicide of claim 7, wherein $R^1$ is methoxy, or methylamino $R^2$ is methyl, X is hydrogen, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, or $C_1$–$C_4$-alkylthio, A is oxygen, sulfur, CH$_2$O, CH=CH, CH$_2$O—N=CR$^7$, or O—N=CR$^7$, $R^7$ is hydrogen, cyano, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, or $C_1$–$C_4$-alkylthio, B is unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocyclyl, unsubstituted or substituted aryl, or unsubstituted or substituted hetaryl.

9. A method for controlling fungi, wherein the fungi or the materials, plants or seed threatened by fungal attack or the soil is or are treated with a fungicidal amount of heteroaromatic compound of the formula:

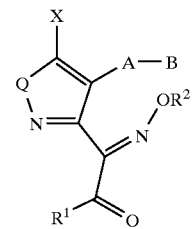

wherein $R^1$ and $C_1$–$C_6$-alkyl, $C_1$–$C_6$-alkoxy, $C_1$–$C_6$-alkylamino or di-$C_1$–$C_6$-alkylamino;

$R^2$ is $C_1$–$C_6$-alkyl;

A is a direct bond; unsubstituted or unsubstituted alkylene, alkenylene or alkynylene;

—(CHR$^4$)$_n$—O—, —(CHR$^4$)$_n$—S—, —(CHR$^4$)$_n$—NH—, —(CHR$^4$)$_n$—NR$_5$—, —(CHR$^4$)$_n$—S(=O)—, —(CHR$^4$)$_n$—S(=O)$_2$—, —(CHR$^4$)$_n$—O—S(=O)— —(CHR$^4$)$_n$—S(=O)—O—, —(CHR$^4$)$_n$—O—S(=O)$_2$—, —(CHR$^4$)$_n$—S(=O)$_2$—O—, —(CHR$^4$)$_n$—C(=O)—, —(CHR$^4$)$_n$—, —C(=O)O—, —(CHR$^4$)$_n$—O—C(=O)—, —(CHR$^4$)$_n$—CR$^5$=N—O—, —(CHR$^4$)$_n$—CR$^5$=N—N=CR$^6$—, —(CHR$^4$)$_n$—O—N=CR$^7$—, n is 0, 1, 2, 3 or 4, and the $R^4$'s are the same or different, when is greater than 1;

R⁴, R⁵ and R⁶ independently of one another are each hydrogen or unsubstituted or substituted $C_1$–$C_6$-alkyl, $C_2$–$C_6$-alkenyl, $C_2$–$C_6$-alkynyl or aryl;

R⁷ is hydrogen, cyano;
unsubstituted or substituted alkyl, alkenyl, alkynyl, cycloalkyl, cycloalkenyl, cycloalkynyl, heterocyclyl, aryl, hetaryl;
unsubstituted or substituted alkoxy, alkenyloxy, alkynyloxy, cycloalkoxy, cycloalkenyloxy, cycloalkynyloxy, heterocyclyloxy, aryloxy, hetaryloxy;
or R⁷ and B, together with the carbon atom to which they are bonded, form an unsubstituted or substituted, saturated or partially unsaturated alicyclic or heterocylic ring system;

B is hydrogen, halogen,
unsubstituted or substituted alkyl, alkenyl, alkynyl; cycloalkyl, cycloalkenyl, cycloalkynyl, heterocyclyl, aryl, hetaryl, —(CHR⁴)$_p$-cycloalkyl, —(CHR⁴)$_p$-cycloalkenyl, —(CHR⁴)$_p$-cycloalkynyl, —(CHR⁴)$_p$-heterocyclyl, —(CHR⁴)$_p$-aryl, —(CHR⁴)$_p$-hetaryl, —(CHR⁴)$_p$—O-cycloalkyl, —(CHR⁴)$_p$—O-cycloalkenyl, —(CHR⁴)$_p$—O-cycloalkynyl, —(CHR⁴)$_p$—O-heterocyclyl, —(CHR⁴)$_p$—O-aryl, —(CHR⁴)$_p$—O-hetaryl, —(CHR⁴)$_p$—S-cycloalkyl, —(CHR⁴)$_p$—S-cycloalkenyl, —(CHR⁴)$_p$—S-cycloalkynyl, —(CHR⁴)$_p$—S-heterocyclyl, —(CHR⁴)$_p$—S-aryl, —(CHR⁴)$_p$—S-hetaryl, —(CHR⁴)$_p$—NH-cycloalkyl, —(CHR⁴)$_p$—NH-cycloalkenyl, —(CHR⁴)$_p$—NH-cycloalkynyl, —(CHR⁴)$_p$—NH-heterocyclyl, —(CHR⁴)$_p$—NH-aryl, —(CHR⁴)$_p$—NH-hetaryl, —(CHR⁴)$_p$—NR⁵-cycloalkyl, —(CHR⁴)$_p$—NR⁵-cycloalkenyl, —(CHR⁴)$_p$—NR⁵-cycloalkynyl, —(CHR⁴)$_p$—NR⁵-heterocyclyl, —(CHR⁴)$_p$—NR⁵-aryl, —(CHR⁴)$_p$—NR⁵-hetarayl, wherein the above-mentioned cyclic groups may in turn carry substituents;

p is 1, 2, 3 or 4, and the R⁴'s are the same or different when n is greater than 1;

x is hydrogen, cyano, nitro, halogen, haloalkyl, haloalkoxy,
unsubstituted or substituted alkyl, alkenyl, alkynyl, cycloalkyl, cycloalkenyl, heterocyclyl, aryl, hetaryl;
unsubstituted or substituted alkoxy, alkenyloxy, alkynyloxy, cycloalkoxy, cycloalkenyloxy, heterocyclyloxy, aryloxy, hetaryloxy;
unsubstituted or substituted alkylthio, alkenylthio, alkynylthio, cycloalkylthio, cycloalkenylthio, heterocyclylthio, arythio, hetarylthio;
amino which may carry one or two of the following groups:
  unsubstituted or substituted alkyl, alkenyl, alkynyl, cycloalkyl-L, cycloalkenyl, heterocyclyl, aryl and/or hetaryl;
  unsubstituted or substituted alkylcarbonyl, alkenylcarbonyl, alkynylcarbonyl, cycloalkylcarbonyl, cycloalkenylcarbonyl, heterocyclylcarbonyl, arylcarbonyl, hetarylcarbonyl;
  unsubstituted or substituted alkylcarbonyloxy, alkenylcarbonyloxy, alkynylcarbonyloxy, cycloalkylcarbonyloxy, cycloalkenylcarbonyloxy, heterocyclycarbonyloxy, arylcarbonyloxy, hetarylcarbonyloxy;
  unsubstituted or substituted alkoxycarbonyl, alkenyloxycarbonyl, alkynyloxycarbonyl, cycloalkoxycarbonyl, cycloalkenyloxycarbonyl, heterocyclyloxycarbonyl, aryloxycarbonyl, hetaryloxycarbonyl;
  unsubstituted or substituted alkylcarbonylamino, alkenylcarbonylamino, alkynylcarbonylamino, cyclalkylcarbonylamino, cycloalkenylcarbonylamino, heterocyclylcarbonylamino, arylcarbonylamino or hetarylcarbonylamino, where these groups optionally carry one of the following groups on the amino group:
    unsubstituted or substituted alkyl, alkenyl, alkynyl, cycloalkyl, cycloalkenyl, heterocyclyl, aryl and/or hetaryl;
  aminocarbonyl which may carry one or two of the following groups on the amino group:
    unsubstituted or substituted alkyl, alkenyl, alkynyl, cycloalkyl, cycloalkenyl, heterocyclyl, aryl and/or hetaryl;
    unsubstituted or substituted alkyl-S(=O)—, alkenyl-S(=O)—, alkynyl-S(=O)—, cycloalkyl-S(=O)—, cycloalkenyl-S(=O)—, heterocyclyl-S(=O)—, aryl-S(=O)—, hetaryl-S(=O)—;
    unsubstituted or substituted alkyl-S(=O)—O—, alkenyl-S(=O)—O—, alkynyl-S(=O)—O—, cycloalkyl-S(=O)—O—, cycloalkenyl-S(=O)—O—, heterocyclyl-S(=O)—O—, aryl-S(=O)—O—, hetaryl-S(=O)—O—;
    unsubstituted or substituted alkyl-O—S(=O)—, alkenyl-O—S(=O)—, alkynyl-O—S(=O)—, cycloalkyl-O—S(=O)—, cycloalkenyl-O—S(=O)—, heterocyclyl-O—S(=O)—, aryl-O—S(=O)—, hetaryl-O—S(=O)—;
    unsubstituted or substituted alkyl-S(=O)$_2$—, alkenyl-S(=O)$_2$—, alkynyl-S(=O)$_2$—, cycloalkyl-S(=O)$_2$—, cycloalkenyl-S(=O)$_2$—, heterocyclyl-S(=O)$_2$—, aryl-S(=O)$_2$—, hetaryl-S(=O)$_2$—;
    unsubstituted or substituted alkyl-O—S(=O)$_2$—O—, alkenyl-O—S(=O)$_2$—O—, alkynyl-O—S(=O)$_2$—, alkynyl-O—S(=O)$_2$—, cycloalkyl-O—S(=O)$_2$—, cycloalkenyl-O—S(=O)$_2$—, heterocyclyl-O—S(=O)$_2$—, aryl-O—S(=O)$_2$—, hetaryl-O—S(=O)$_2$—;
    unsubstituted or substituted alkyl-ON=CR⁸—, alkenyl-ON=CR⁸—, alkynyl-ON=CR⁸—, cycloalkyl-ON=CR⁸—, cycloalkenyl-ON=CR⁸—, heterocyclyl-ON=CR⁸—, aryl-ON=CR⁸—, hetaryl-ON=CR⁸—;

R⁸ is hydrogen, cyano;
unsubstituted or substituted alkyl, alkenyl, alkynyl, cycloalkyl, cycloalkenyl, cycloalkynyl, heterocyclyl, aryl, or hetaryl;
unsubstituted or substituted alkoxy, alkenyloxy, alkynyloxy, cycloalkoxy, cycloalkenyloxy, cycloalkynyloxy, heterocyclyloxy, aryloxy or hetaryloxy;

Q is oxygen or a substituted nitrogen;

and its plant-tolerated acid addition products and base addition products.

10. The method of claim 9, wherein

R¹ is methoxy, or methylamino

R² is methyl,

X is hydrogen, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, or $C_1$–$C_4$-alkylthio, A is oxygen, sulfur, $CH_2O$, CH=CH, $CH_2O$—N=CR⁷, or O—N=CR⁷, R⁷ is hydrogen, cyano, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, or $C_1$–$C_4$-alkylthio, B is unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocyclyl, unsubstituted or substituted aryl, or unsubstituted or substituted hetaryl.

* * * * *